(12) United States Patent
Iwadate et al.

(10) Patent No.: US 7,824,900 B2
(45) Date of Patent: Nov. 2, 2010

(54) DNA ANALYZING APPARATUS, DNA SENSOR, AND ANALYZING METHOD

(75) Inventors: Akihito Iwadate, Fussa (JP); Jun Ogura, Fussa (JP)

(73) Assignee: Casio Computer Co., Ltd., Tokyo (JP)

( * ) Notice: Subject to any disclaimer, the term of this patent is extended or adjusted under 35 U.S.C. 154(b) by 424 days.

(21) Appl. No.: 11/178,703

(22) Filed: Jul. 11, 2005

(65) Prior Publication Data

US 2005/0244886 A1   Nov. 3, 2005

Related U.S. Application Data

(63) Continuation of application No. PCT/JP2004/002772, filed on Mar. 4, 2004.

(30) Foreign Application Priority Data

Mar. 10, 2003 (JP) ............................. 2003-063712
Mar. 10, 2003 (JP) ............................. 2003-063755

(51) Int. Cl.
*C12M 1/34* (2006.01)
*C12M 3/00* (2006.01)
*C12M 1/00* (2006.01)
*G01N 15/06* (2006.01)
*C07H 21/02* (2006.01)

(52) U.S. Cl. .............. 435/287.2; 435/283.1; 435/287.1; 422/68.1; 536/23.1

(58) Field of Classification Search .............. 435/283.1, 435/287.1, 287.2; 422/68.1
See application file for complete search history.

(56) References Cited

U.S. PATENT DOCUMENTS

| | | | |
|---|---|---|---|
| 5,605,662 A | 2/1997 | Heller et al. | |
| 6,027,880 A * | 2/2000 | Cronin et al. | 435/6 |
| 6,093,370 A * | 7/2000 | Yasuda et al. | 422/68.1 |
| 6,150,102 A | 11/2000 | Mills, Jr. et al. | |
| 6,197,503 B1 | 3/2001 | Vo-Dinh et al. | |
| 6,309,602 B1 | 10/2001 | Ackley et al. | |
| 6,490,533 B2 * | 12/2002 | Weiner et al. | 702/27 |
| 6,514,702 B1 | 2/2003 | Okano et al. | |
| 2002/0131899 A1 | 9/2002 | Kovacs | |
| 2003/0087239 A1* | 5/2003 | Stanton et al. | 435/6 |

FOREIGN PATENT DOCUMENTS

JP    9-505729    6/1997

(Continued)

OTHER PUBLICATIONS

Webster's II New Riverside University Dictionary. Boston, Houghton Mifflin, 1994. p. 264.*

(Continued)

*Primary Examiner*—Frank W Lu
(74) *Attorney, Agent, or Firm*—Holtz, Holtz, Goodman & Chick, PC

(57) ABSTRACT

A DNA analyzing apparatus includes a bath containing an electrophoresis medium. A plurality of probe electrodes are arranged in the bath. A plurality of spots each composed of probe DNA fragments having known base sequences are arranged on the respective probe electrodes. Temperature regulating elements are provided to adjust the temperatures of the plurality of spots via the corresponding probe electrode.

17 Claims, 28 Drawing Sheets

FOREIGN PATENT DOCUMENTS

| | | |
|---|---|---|
| JP | 11-512605 A | 11/1999 |
| WO | WO 97/12030 A1 | 4/1997 |

OTHER PUBLICATIONS

R. Sosnowski et al; Rapid Determination of Single Base Mismatch Mutations in DNA Hybrids by Direct Electric Field Control; Proc. Natl. Acad. Sci. USA; vol. 94, pp. 1119-1123, Feb. 1997.

G. Ramsay; DNA Chips: State of the Art; Nature Biotechnology vol. 16, Jan. 1998; pp. 40-44.

M. Gozlan; Les Biopuces Ala Conquete Du Marche; La Recherche 318; Mar. 1999; pp. 60-64.

M. Heller et al; Active Microelectronic Chip Devices Which Utilize Controlled Electrophoretic Fields for Multiplex DNA Hybridization and Other Genomic Applications; Electrophoresis 2000, 21, pp. 157-164.

Japanese Office Action dated Jan. 13, 2009 and English translation thereof issued in a counterpart Japanese Application No. 2003-063712.

Tsuyoshi Tanaka, et al., Oligonucleotide-Arrayed TFT Photosensor Applicable for DNA Chip Technology, Biotechnology and Bioengineering, vol. 95, No. 1, Sep. 5, 2006, pp. 22-28 (published online in Wiley InterScience (www.interscience.wiley.com) on May 26, 2006.

Japanese Office Action dated Apr. 21, 2009, and English translation thereof, issued in a counterpart Japanese Application No. 2003-063712.

* cited by examiner

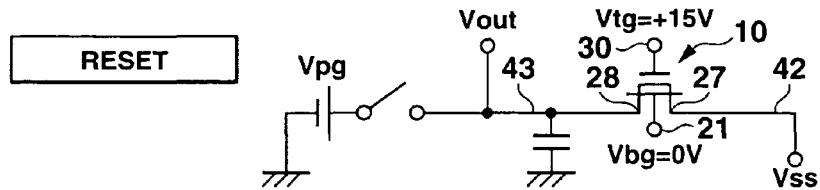
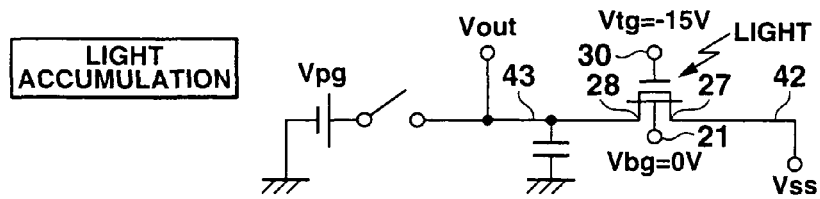
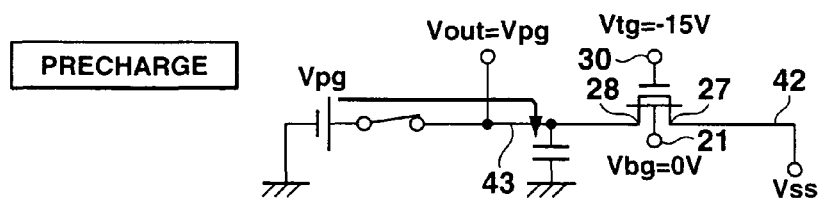
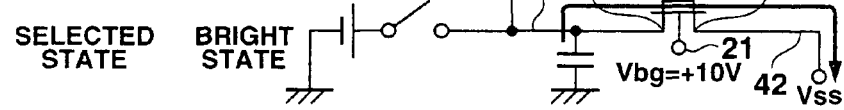
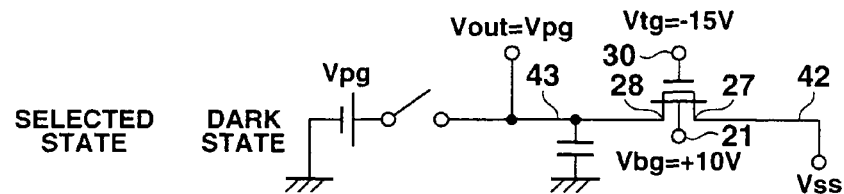
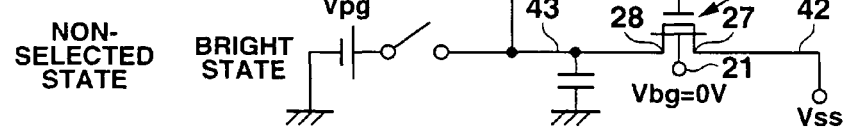
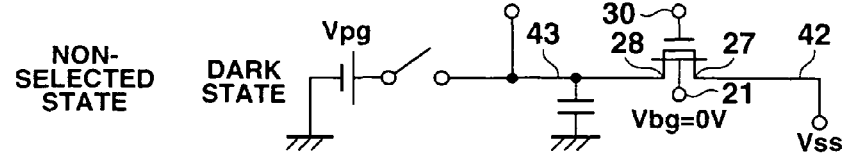

DNA ANALYZING APPARATUS, DNA SENSOR, AND ANALYZING METHOD

CROSS-REFERENCE TO RELATED APPLICATIONS

This is a Continuation Application of PCT Application No. PCT/JP2004/002772, filed Mar. 4, 2004, which was published under PCT Article 21(2) in English.

This application is based upon and claims the benefit of priority from prior Japanese Patent Applications No. 2003-063712, filed Mar. 10, 2003; and No. 2003-063755, filed Mar. 10, 2003, the entire contents of both of which are incorporated herein by reference.

BACKGROUND OF THE INVENTION

1. Field of the Invention

The present invention relates to a DNA analyzing apparatus, a DNA sensor, and an analyzing method which are used to analyze DNAs having different numbers of bases.

2. Description of the Related Art

In recent years, information on biological genes has been utilized in various fields such as medical care and agriculture. It is essential to understand the structures of DNAs in utilizing genetic information. A DNA has two spirally twisted polynucleotide chains each having a base sequence in which four types of bases (adenine: A, guanine: G, cytosine: C, thymine: T) are one-dimensionally arranged. The base of one of the nucleotide chains is bonded to the base of the other on the basis of the complementarity between adenine and thymine and between guanine and cytosine.

To understand the structure of a DNA is to identify its base sequence. DNA microarrays and their reading apparatuses have been developed in order to identify the base sequences of DNAs. In the prior art, a DNA microarray and its reading apparatus are used to identify the base sequences of sample DNAs as describe below.

First, plural types of single stranded probe DNA fragments are prepared which have known base sequences. The plural types of probe DNA fragments are fixed to a solid carrier such as slide glass, as spots so as to be aligned with one another. On the DNA microarray obtained, the plurality of spots are arranged on an array. One spot is a cluster of probe DNA fragments of one type. Different spots have respective base sequences of probe DNA fragments.

Then, a sample DNA extracted from a specimen is denatured into single stranded sample DNA fragments. A fluorescent substance or the like is bonded to each of the denatured sample DNA fragments. In general, plural types of sample DNA fragments are present.

Then, the plural types of sample DNA fragments are added to the DNA microarray. The plural types of sample DNA fragments are then hybridized to their complementary probe DNA fragments. Specifically, certain types of sample DNA fragments are hybridized to complementary ones of the plural types of probe DNA fragments. However, these types of sample DNA fragments are not hybridized to non-complementary probe DNA fragments. Each of the sample DNA fragments is marked with a fluorescent substance. Consequently, probe DNA fragments bonded to the corresponding sample DNA fragments emit fluorescence.

For example, a sample DNA fragment having the base sequence TCGGGAA is bonded to a probe DNA fragment having the base sequence AGCCCTT. Then, the spot including probe DNA fragments of this type emits fluorescence.

Then, the DNA microarray is set in a reading apparatus. The reading apparatus is used to analyze the DNA microarray. The reading apparatus measures the distribution of fluorescence intensities on the DNA microarray. The distribution of fluorescence intensities on the DNA microarray is outputted as a two-dimensional image. A spot in the outputted image which has a high fluorescence intensity indicates that it contains probe DNA fragments having a base sequence complementary to the base sequence of sample DNA fragments. Accordingly, the base sequence of the sample DNA fragments can be determined depending on which spot in the two-dimensional image has a higher fluorescence intensity.

However, with the above DNA microarray, the sample DNA fragments are simply added to the DNA microarray. Consequently, the distribution of the sample DNA fragments is not uniform. That is, the density of sample DNA fragments may be high on some spots on the DNA microarray but may be low on other spots. Therefore, if the probe DNA fragments in a spot are complementary to any of the plural types of sample DNA fragments, the emission luminance of the fluorescence may vary depending on the density of sample DNA fragments on the spot.

To solve this problem, PCT National Publication No. 11-512605 describes a DNA microarray comprising electrodes which are arranged on a substrate in a matrix and to each of which a spot including probe DNA fragments is fixed. In this microarray, a dispersion medium is applied to the entire surface of the substrate so as to cover all the electrodes and spots.

Description will be given below of an identifying method using the DNA microarray described in PCT National Publication No. 11-512605. First, sample DNA fragments are injected into a dispersion medium. A positive voltage is sequentially applied to the electrodes one by one for spot scanning. Sample DNA fragments in the dispersion medium migrate to selected ones of the plurality of electrodes to which the positive voltage has been applied. Accordingly, the density of the sample DNA fragments is high at the spots of the selected electrodes. Such spot scanning sequentially increases the density of the sample DNA fragments in the respective spots one by one. Therefore, the spots that are complementary to the sample DNA fragments have an almost equal fluorescence intensity. As described above, the technique described in PCT National Publication No. 11-512605 utilizes the electrophoresis of the sample DNA fragments through the dispersion medium.

However, with the conventional DNA microarray, if some of the plural types of sample DNA fragments have a complementary base sequence, the sample DNA fragments may be partially hybridized to one another during electrophoresis. Thus, even if the partially hybridized sample DNA fragments migrate to the complementary spot, they are not hybridized to that spot. As a result, the base sequences of the plural types of sample DNA fragments cannot be identified. Therefore, although the whole electrophoresis medium is heated to denature the sample DNA fragments into a single strand state, it is subsequently cooled to provide for hybridization. This is inefficient. Furthermore, it is impossible to hybridize only arbitrary spots.

It is thus an object of the present invention to efficiently hybridize sample DNA fragments even during electrophoresis.

BRIEF SUMMARY OF THE INVENTION

To accomplish the above-object, a DNA analyzing apparatus set forth the in claim 1 comprises:

a bath (for example, a bath 71) containing an electrophoresis medium;

a plurality of probe electrodes (for example, probe electrodes 35) arranged in the bath;

a plurality of spots (for example, spots 60) each including probe DNA fragments having known base sequences and arranged on the respective probe electrodes; and temperature regulating elements (for example, temperature regulating elements 72) which adjust the temperatures of the plurality of spots via the corresponding probe electrodes, as shown in, for example, FIGS. 1 and 2.

In the present invention, sample DNA fragments in the electrophoresis medium in the bath can be attracted to the probe electrodes by electrophoresis. On this occasion, the sample DNA fragments maintain a denatured state in which they are not hybridized to probe DNA fragments. Accordingly, spots, that is, the probe DNA fragments, and the surrounding electrophoresis medium are relatively hot. Consequently, the sample DNA fragments cannot be hybridized to the corresponding probe DNA fragments if this temperature remains. However, since the temperature regulating elements regulate the temperatures of the plurality of spots via the corresponding probe electrodes, the vicinities of the spots in which hybridization occurs can be locally and efficiently cooled. This makes it possible to easily hybridize the complementary sample and probe DNA fragments to each other.

In the present DNA analyzing apparatus, the temperature regulating elements may abut against the respective probe electrodes to selectively regulate the temperatures of some of the plurality of spots via the some of the plurality of probe electrodes.

That is, the temperature regulating elements selectively transmit heat to arbitrary probe electrodes to enable only arbitrary spots to be hybridized. Specifically, if the probe DNA fragments in the respective spots on predetermined probe electrodes are preferably hybridized, while the probe DNA fragments in the respective spots on the probe electrodes other than the predetermined ones are preferably not hybridized (for example, if at step S19, probe DNA fragments 61 on probe electrodes 35 in the seventh to ninth columns are preferably hybridized, while probe DNA fragments 61 on probe electrodes 35 in the fourth to sixth columns are preferably not hybridized), then the temperature is reduced so as to hybridize the probe DNA fragments in the respective spots on the predetermined probe electrodes and is increased so as not to hybridize the probe DNA fragments in the respective spots on the probe electrodes other than the predetermined ones. This makes it possible to selectively form spots that are easily dispersed during agitation and spots that are not easily dispersed during agitation.

Furthermore, in the DNA analyzing apparatus:

if a first electrode (for example, a first electrode 74) and a second electrode (for example, a second electrode 75) are provided which are arranged in the bath opposite each other in a width direction of the bath as shown in, for example, FIGS. 1 and 2, then the sample DNA fragments can be efficiently electrically migrated by applying voltages between the first and second electrodes.

The probe electrode may be divided into plural sets of electrodes each composed of one probe electrode or a number of adjacent probe electrodes, the spots arranged in predetermined ones of the plural sets of electrodes may have different base sequences of the probe DNA fragments and the same number of bases in one probe DNA fragment or the numbers of bases in one probe DNA fragment for these spots may be more similar to one another than those for the spots arranged on the probe electrodes other than the predetermined ones, and each of the probe DNA fragments located on the second electrode side may have a smaller number of bases than each of the probe DNA fragments located on the first electrode side.

The DNA fragment has a higher electrophoresis mobility as the number of bases in it decreases. Thus, when plural types of sample DNA fragments having different numbers of bases are injected into the first electrode side of the electrophoresis medium, sample DNA fragments having smaller numbers of bases are likely to migrate to the second electrode, whereas sample DNA fragments having larger numbers of bases are unlikely to migrate to the second electrode. In this case, according to the invention set forth in claim 4, for the plurality of spots, the number of bases in the probe DNA fragment decreases as the electrode set is closer to the second electrode. Accordingly, each sample DNA fragment migrates onto an electrode set with a corresponding probe DNA fragment having almost the same number of bases owing to the voltage between the first electrode and the second electrode. The plurality of probe electrodes and the plurality of spots are arranged deeper than the first and second electrodes. Accordingly, while the sample DNA fragments are migrating from the first electrode to the second electrode, they do not reach any spots. However, if the probe electrode is subjected to a voltage which is higher than that of the first electrode and which is high enough to attract the corresponding sample DNA fragments, the sample DNA fragments also migrate in a depth direction.

Consequently, each sample DNA fragment migrates to the corresponding probe DNA fragment having almost the same number of bases. Thus, the sample DNA fragment can be hybridized only to the complementary probe DNA fragment having the same number of bases. It is thus possible to efficiently analyze the base sequence of each of the plural types of sample DNA fragments having different electrophoresis moving speeds because of different numbers of bases.

The present invention may comprise:

a voltage control circuit (for example, a voltage control circuit 73) which repeats a voltage applying step (step S1, step S6, and step S11) a number of times equal to the number of sets of electrodes, the step applying voltages for a predetermined time so that the potential of the second electrode is higher than the potential of the first electrode as shown in FIGS. 5, and 10 to 12.

That is, when the a voltage applying step is repeated to apply the voltage for the predetermined time so that the potential of the second electrode is higher than the potential of the first electrode, the sample DNA fragments migrate from the first electrode to the second electrode. This enables the movable sample DNA fragments to be appropriately moved.

The present invention may comprise a temperature control circuit which causes the temperature regulating elements to perform a heating operation while the voltage control circuit is repeating the voltage applying step and which causes the temperature regulating elements to stop the heating operation when the voltage control circuit stops repeating the voltage applying step.

In the present invention, the temperature control circuit causes the temperature regulating elements to perform the heating operation. Accordingly, the lack of hybridization allows the sample DNA fragments in the electrophoresis medium to migrate easily. Subsequently, the temperature control circuit ends the heating operation of the heating elements. This reduces the temperature of the electrophoresis medium to allow the sample DNA fragments to be easily hybridized.

In the DNA analyzing apparatus according to the present invention, the voltage control circuit may sequentially select, after each voltage applying step, one of the plurality of electrode sets which is closer to the second electrode, starting with one closest to the second electrode, and apply voltages so that the potentials of one or more probe electrodes in the selected electrode set are higher than the potential of at least one of the first and second electrodes.

In the voltage applying step, the sample DNA fragments migrate from the first electrode to the second electrode. The distance each sample DNA fragment migrates increases with decreasing number of bases in the sample DNA fragment. For example, a sample DNA fragment with a smaller number of bases migrates closest to the electrode set closest to the second electrode during the first voltage applying step. When an electrode set is subsequently selected, the sample DNA fragment with the smaller number of bases migrates in the depth direction toward the selected electrode set because the potentials of probe electrodes in this electrode set are higher than the potential of at least one of the first and second electrodes.

In this manner, the voltage applying step is repeated and one of the plurality of electrode sets is sequentially selected between the voltage applying steps, starting with the one closest to the second electrode. Then, the sample DNA fragments are assigned to the respective electrode sets so that the number of bases in the sample DNA fragment decreases as the corresponding electrode set is closer to the second electrode.

Subsequently, the temperature regulating circuit ends the heating operation of the temperature regulating elements. Accordingly, the temperature of the electrophoresis medium decreases to allow each sample DNA fragment to be easily hybridized to the complementary probe DNA having the same number of bases.

In the DNA analyzing apparatus according to the present invention, the voltage control circuit may apply voltages so that after all the electrode sets have been selected, the potential of at least one of the first and second electrodes is higher than the potentials of the plurality of probe electrodes.

When the voltages are applied so that after all the electrode sets have been selected, the potential of at least one of the first and second electrodes is higher than the potentials of the plurality of probe electrodes, non-hybridized sample DNA fragments leave the spots and migrate to at least one of the first and second electrodes. However, the sample DNA fragments hybridized to the complementary probe DNA fragments do not leave the spots.

Consequently, the sample DNA fragments are distributed only at the spots of the complementary probe DNA fragments. Therefore, only the hybridized spots can be accurately sensed.

The DNA analyzing apparatus according to the present invention may have a plurality of photo sensor elements provided in association with the plurality of spots arranged on the respective probe electrodes. Each of the photo sensor elements can sense the presence of hybridization at the corresponding spot. Therefore, the plurality of spots can be simultaneously sensed.

An analyzing method according to the present invention includes:

an electrophoresis step of applying voltages to a plurality of probe electrodes provided in a bath containing an electrophoresis medium to attract sample DNA fragments in the electrophoresis medium to probe DNA fragments provided on the probe electrodes, and a temperature regulating step of regulating the temperatures of the probe DNA fragments and surrounding electrophoresis medium via the probe electrodes.

According to the present analyzing method, the temperatures of the probe DNA fragments and surrounding electrophoresis medium can be regulated via the probe electrodes as required. This enables arbitrary probe DNA fragments to be selectively hybridized while allowing the sample DNA fragments located close to the probe DNA fragments other than the arbitrary ones to remain denatured. Therefore, quick electrophoresis can be achieved.

As shown in, for example, FIGS. 1 and 2, another DNA analyzing apparatus according to the present invention comprises:

a bath (for example, a bath 71) containing an electrophoresis medium;

a first electrode (for example, a first electrode 74) and a second electrode (for example, a second electrode 75) arranged in the bath opposite each other in a width direction of the bath;

a light sensing device (for example, a light sensing device 2) located in the bath at a height different from those of the first and second electrodes as viewed in the width direction of the bath and between the first electrode and the second electrode as viewed in a height direction of the bath;

a plurality of probe electrodes (for example, probe electrodes 35) arranged on a surface of the light sensing device and in the width direction of the bath; and a plurality of spots (for example, spots 60) each including probe DNA fragments having known base sequences and arranged on the plurality of probe electrodes.

The plurality of probe electrodes are divided into plural sets of electrodes each composed of one probe electrode or a number of adjacent probe electrodes. Each of the probe DNA fragments positioned on the second electrode side has a smaller number of bases than each of the probe DNA fragments positioned on the first electrode side.

According to the present invention, there is provided a DNA sensor including:

a light sensing device (for example, a light sensing device 2) having an electrophoresis medium disposed on its front surface;

a plurality of probe electrodes (for example, probe electrodes 35) arranged on the front surface of the light sensing device in a plurality of rows; and a plurality of spots (for example, spots 60) each including probe DNA fragments having known base sequences and arranged on the respective probe electrodes, and wherein the plurality of probe electrodes are divided into plural sets of electrodes each composed of one probe electrode or a number of adjacent probe electrodes, and those of the plurality of spots which are arranged in a common electrode set have different base sequences of the probe DNA fragments and the same number of bases in one probe DNA fragment or the numbers of bases in one probe DNA fragment for these spots are more similar to one another than those for the spots arranged on the probe electrodes other than the predetermined ones, as shown in, for example, FIGS. 1 and 2.

As the number of bases in the DNA fragment decreases, its volume and thus its fluid resistance decrease to increase its electrophoresis mobility. Thus, when plural types of sample DNA fragments having different numbers of bases are injected into the first electrode side of the electrophoresis medium, the sample DNA fragments having smaller numbers of bases are likely to migrate to the second electrode side. The sample DNA fragments having larger numbers of bases are unlikely to migrate to the second electrode side. In this case, for the plurality of spots, the number of bases in the probe DNA fragment decreases as the electrode set is closer to the second electrode. Accordingly, each sample DNA fragment migrates onto an electrode set with a corresponding probe DNA fragment having almost the same number of bases. The plurality of probe electrodes and the plurality of spots are arranged deeper than the first and second electrodes. Accordingly, while the sample DNA fragments are migrating from the first electrode to the second electrode, they do not reach any spots. However, if voltages are applied to the probe electrodes, the sample DNA fragments also migrate in a depth direction.

Consequently, each sample DNA fragment migrates to the corresponding probe DNA fragment having the same or a similar number of bases. It is thus possible to easily extract a sample DNA fragment having the same number of bases as that in the corresponding probe DNA fragment. Accordingly, complementary sample and probe DNA fragments can be quickly hybridized to each other. This makes it possible to promptly analyze the base sequence of each of the plural types of sample DNA fragments having different numbers of bases. Furthermore, the use of the light sensing device enables the almost simultaneous analysis of the base sequences of the plural types of sample DNA fragments having different numbers of bases.

In the DNA analyzing apparatus according to the present invention, the voltage control circuit sequentially selects, after each voltage applying step, one of the plurality of electrode sets which is closer to the second electrode, starting with one closest to the second electrode, and applies voltages so that the potentials of one or more probe electrodes in the selected electrode set are higher than the potential of the first and second electrodes or so that the potentials of one or more probe electrodes in the selected electrode set are equivalent to the higher of the potentials of the first and second electrodes (for example, steps S4, S9, and S14 such as those shown in FIGS. 10 and 11).

According to the present invention, at the voltage applying step, the sample DNA fragments migrate from the first electrode to the second electrode. The distance each sample DNA fragment migrates increases with decreasing number of bases in the sample DNA fragment. For example, a sample DNA fragment with a smaller number of bases migrates closest to the electrode set closest to the second electrode during the first voltage applying step. When an electrode set is subsequently selected, the sample DNA fragment with the smaller number of bases migrates in the depth direction toward the selected electrode set because the potentials of probe electrodes in this electrode set are higher than the potentials of the first and second electrodes or equivalent to the higher of the potentials of the first and second electrodes.

In this manner, the voltage applying step is repeated and one of the plurality of electrode sets is sequentially selected between the voltage applying steps, starting with the one closest to the second electrode. Then, the sample DNA fragments are assigned to the respective electrode sets so that the number of bases in the sample DNA fragment decreases as the corresponding electrode set is closer to the second electrode.

Consequently, each sample DNA fragment migrates to the corresponding probe DNA fragment having the same number of bases. Thus, the sample DNA fragment can be hybridized only to the complementary probe DNA fragment having the same number of bases. It is thus possible to almost simultaneously analyze the base sequences of the plural types of sample DNA fragments having different numbers of bases.

In the DNA analyzing apparatus according to the present invention, the voltage control circuit applies voltages so that after all the electrode sets have been selected, the potential of at least one of the first and second electrodes is higher than the potentials of the plurality of probe electrodes (for example, step S26 such as the one shown in FIG. 12).

In the present invention, the voltage is applied so that after all the electrode sets have been selected, the potential of at least one of the first and second electrodes is higher than the potentials of the plurality of probe electrodes. Non-hybridized sample DNA fragments leave the spots and migrate to the first and second electrodes. However, the sample DNA fragments hybridized to the complementary probe DNA fragments do not leave the spots.

Consequently, the sample DNA fragments are distributed only at the spots of the complementary probe DNA fragments.

As shown in, for example, FIG. 5, the DNA analyzing apparatus according to the present invention comprises a driver circuit (for example, a driver circuit 76) which drives the light sensing device after the voltage control circuit has applied voltages so that the potential of at least one of the first and second electrodes is higher than the potentials of the plurality of probe electrodes.

According to the present invention, the sample DNA fragments are distributed only at the spots of the complementary probe DNA fragments. Furthermore, the driver circuit drives the light sensing device so that the light sensing device can detect the distribution of fluorescence intensities to determine the distribution of the sample DNA fragments. As a result, the base sequences of the sample DNA fragments can be determined.

The analyzing method according to the present invention has:

a sample DNA fragment dispersing step of applying voltages between a first electrode (for example, a first electrode 74) and a second electrode (for example, a second electrode 75) arranged in bath (for example, a bath 71) opposite each other, the bath containing an electrophoresis medium, to move those (for example, a single stranded sample DNA fragment 151) of a plurality of sample DNA fragments provided in the electrophoresis medium between the first electrode and the second electrode which sample DNA fragments have a smaller number of bases, to a vicinity of probe electrodes on the second electrode side provided with those of plural types of probe DNA fragments (for example, single stranded probe DNA fragments 61) provided at respective spots on a plurality of probe electrodes (for example, probe electrodes 35) which probe DNA fragments have smaller numbers of bases, while moving move those (for example, a single stranded sample DNA fragment 153) of the plurality of sample DNA fragments which have a larger number of bases, to a vicinity of probe electrodes on the first electrode side provided with those of the plural types of probe DNA fragments provided at the respective spots on the plurality of probe electrodes which probe DNA fragments have a larger number of bases, as shown in, for example, FIG. 1.

According to the present invention, when the sample DNA fragments migrate electrically under the effect of an electric field between the first electrode and the second electrode, their speeds are reduced by their fluid resistance, which increases consistently with the number of bases in the sample DNA fragments. Accordingly, the positions of the sample DNA fragments can be varied depending on the number of bases. Thus, by arranging the voltages applied between the first and second electrodes and the probe DNA fragments in accordance with the number of bases, it is possible to promptly extract a sample DNA fragment having almost the same number of bases as that in the corresponding probe DNA fragment. Therefore, the complementary sample and probe DNA fragments can be quickly hybridized to each other.

BRIEF DESCRIPTION OF THE SEVERAL VIEWS OF THE DRAWING

FIGS. 8A to 8G are conceptual views showing operations in respective states of the photo sensor element.

DETAILED DESCRIPTION OF THE INVENTION

A specific embodiment of the present invention will be described below with reference to the drawings. However, the scope of the present invention is not limited to the illustrated examples.

Figure 1:
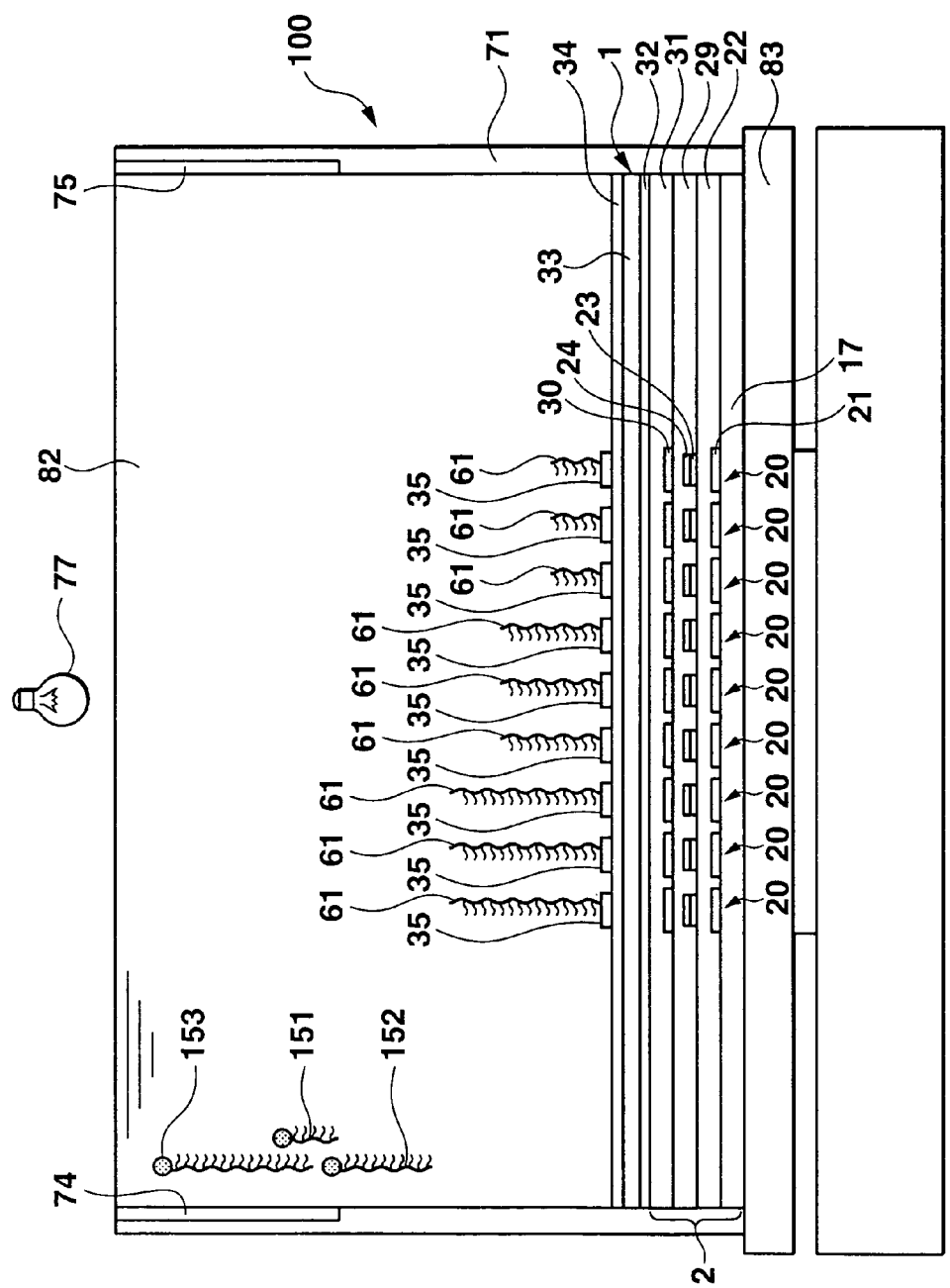
FIG. 1 is a partly exploded side view showing a DNA identifying apparatus to which the present invention is applied.
Figure 2:
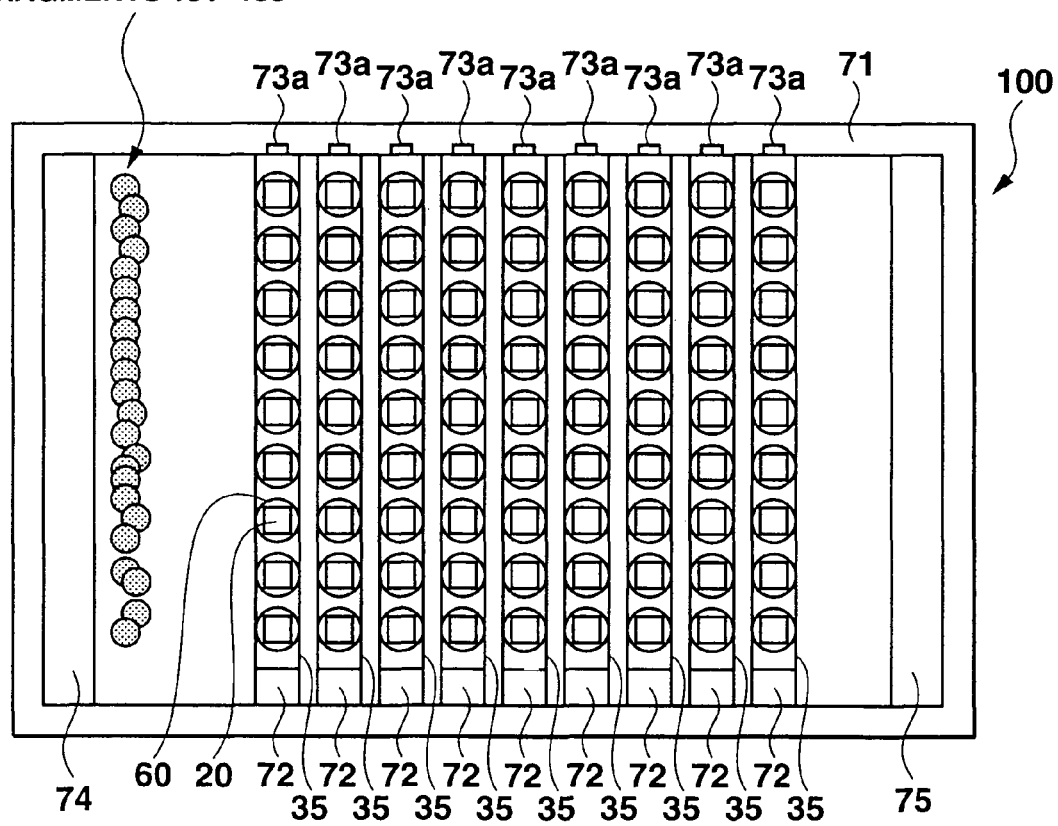
FIG. 2 is top plan view showing the DNA identifying apparatus.

FIG. 1 is an exploded front view showing a DNA identifying apparatus 100 that analyzes DNAs. FIG. 2 is a top plan view of the DNA identifying apparatus 100.

The DNA identifying apparatus 100 comprises a bath 71, an ultraviolet irradiator 77 located above the bath 71, first and second electrodes 74, 75 arranged on the upper parts of inside of the bath 71 and horizontally opposite each other in a width direction of the bath 71, and a DNA sensor 1 that can be installed at and removed from the bottom of the bath 71.

Figure 3:
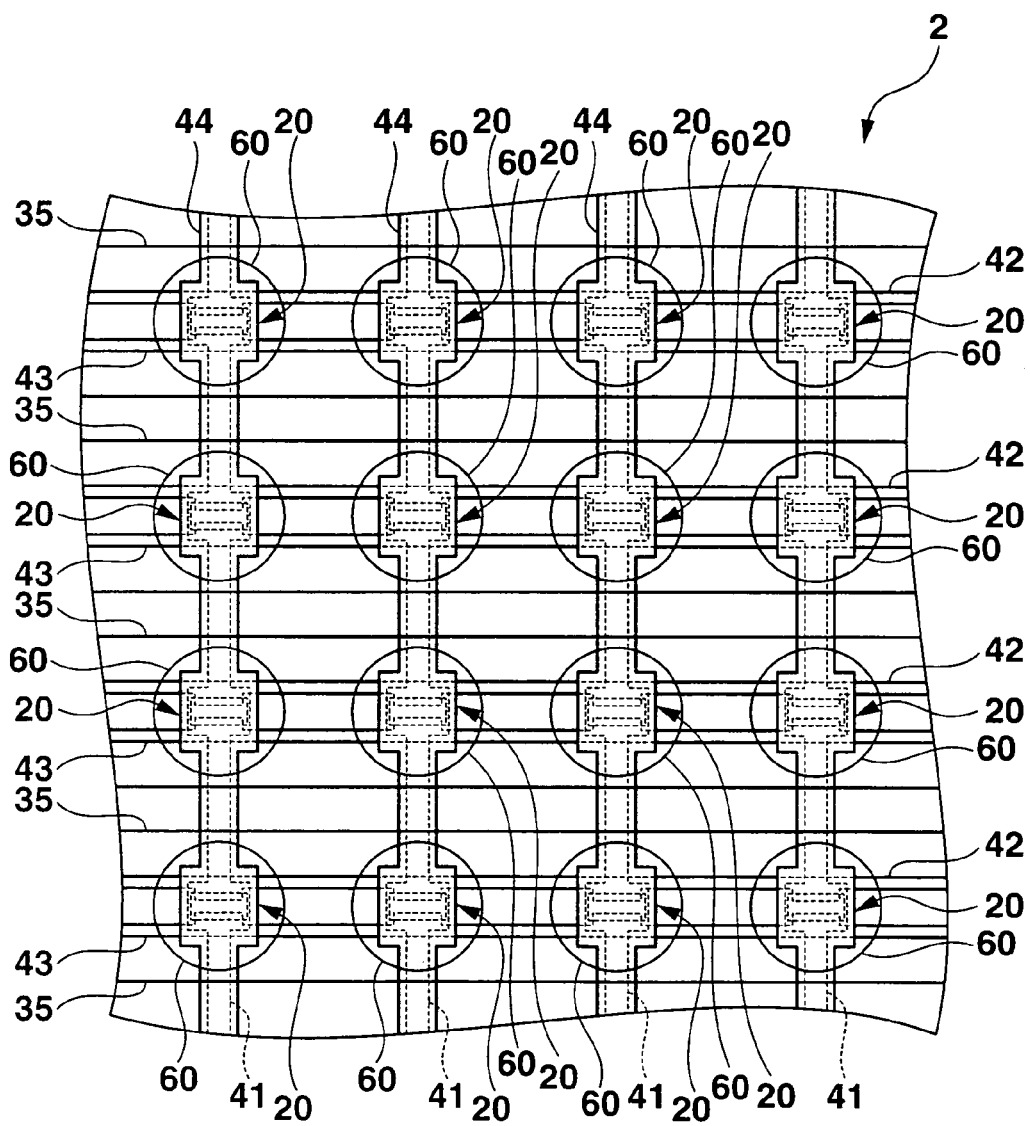
FIG. 3 is a plan view showing some pixels of a light sensing device provided in the DNA identifying apparatus.
Figure 4A:
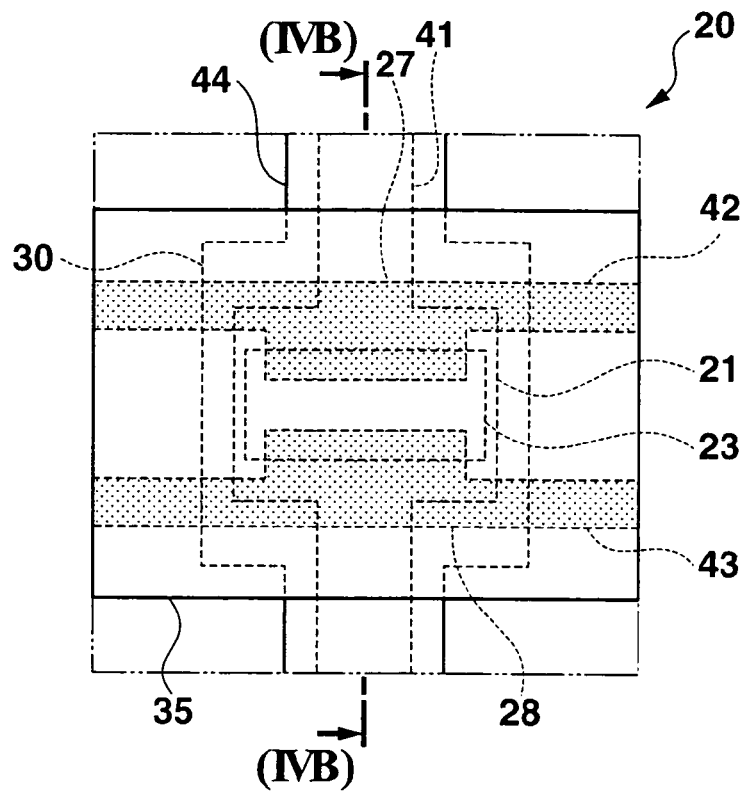
FIG. 4A is a plan view showing one pixel of the light sensing device.
Figure 4B:
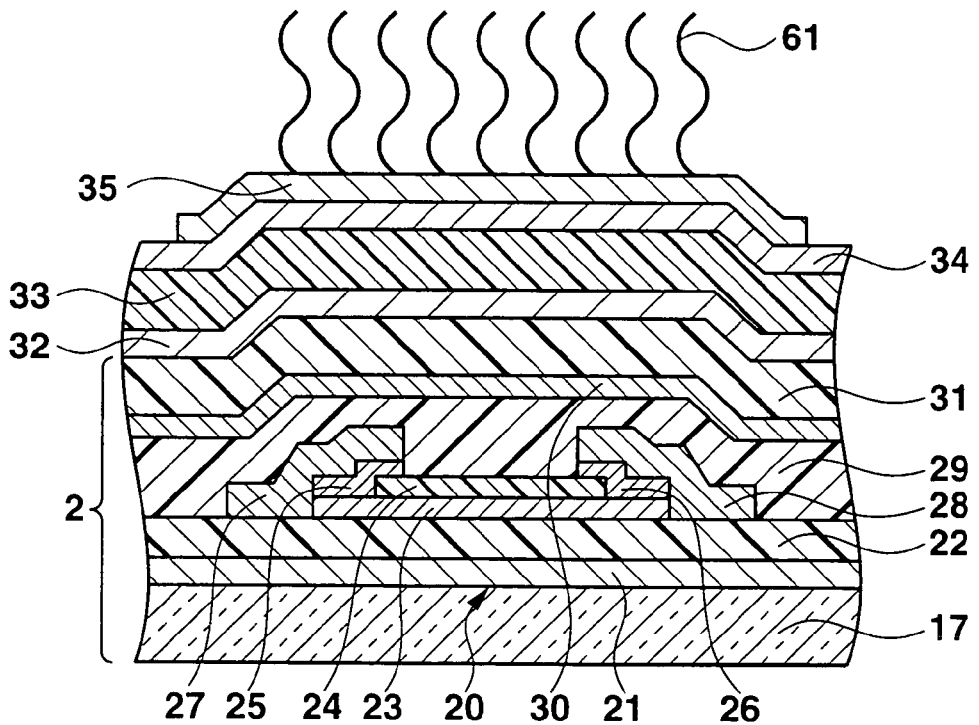
FIG. 4B is a sectional view taken along line (IVB)-(IVB) in FIG. 4A.

The DNA sensor 1 will be described with reference to FIGS. 3, 4A, and 4B. FIG. 3 is a plan view of the DNA sensor 1. FIG. 4A is a plan view showing one pixel of the DNA sensor 1. FIG. 4B is an exploded sectional view taken along line (IVB)-(IVB) in FIG. 4A.

The DNA sensor 1 includes a light sensing device 2 that is a image pickup device, an electromagnetic shield layer 32 formed all over a surface of the light sensing device 2, an overcoat layer 33 formed on the electromagnetic shield layer 32, an ultraviolet blocking layer 34 formed on the overcoat layer 33, a plurality of probe electrodes 35 arranged on a surface of the ultraviolet blocking layer 34, and a plurality of spots 60 each including a cluster of single stranded probe DNA fragments 61 and fixedly arranged on the probe electrode 35.

The light sensing device 2 includes a generally planar transparent substrate 17 and photo sensor elements 20 including a plurality of double gate type field effect transistors arranged on a surface of the transparent substrate 17 in an n×m (m and n are both integers equal to or larger than 2) matrix. In the specification, the term "row" refers to a line of the m photo sensor elements 20 arranged horizontally in a line along a source line 42 and a drain line 43, described later. The term "column" refers to a line of the n photo sensor elements 20 arranged vertically in a line along a top gate line 44 and a bottom gate line 41, described later.

The transparent substrate 17 allows light to pass through (this nature will hereinafter simply be referred to as translucence) and is made of glass such as quartz glass or plastic such as polycarbonate. A back surface of the transparent substrate 17 constitutes a back surface of the light sensing device 2. A shading substrate may be used in place of the translucent transparent substrate 17.

These photo sensor elements 20 are photoelectric converting elements constituting pixels. Each photo sensor element 20 comprises a bottom gate electrode 21 formed on the transparent substrate 17, a bottom gate insulating film 22 formed on the bottom gate electrode 21, a semiconductor film 23 which sandwiches the bottom gate insulating film 22 between the bottom gate electrode 21 and the semiconductor film 23 and which is located opposite the bottom gate electrode 21, a channel protecting film 24 formed on a central portion of the semiconductor film 23, impurities doped semiconductor films 25 and 26 formed at opposite ends of the semiconductor film 23 so as to be spaced from each other, a source electrode 27 formed on one 25 of the impurities doped semiconductor films, a drain electrode 28 form on the other 26 of the impurities doped semiconductor films, a top gate insulating film 29 formed on the source electrode 27 and drain electrode 28, and a top gate electrode 30 which sandwiches the top gate insulating film 23 and channel protecting film 24 between the semiconductor film 23 and the top gate electrode 30 and which is located opposite the semiconductor film 23.

The bottom gate electrode 21 is formed on the transparent substrate 17 for each photo sensor element 20. The m bottom gate lines 41 are formed on the transparent substrate 17 so as to extend in the vertical direction so that each of the bottom gate lines 41 corresponds to one column. Each bottom gate line 41 is formed integrally with the bottom gate electrode 21 of one of the vertically arranged photo sensor elements 20 which is located in the same column as that of this bottom gate line 41. The bottom gate electrode 21 and the bottom gate line 41 are conductive, have a shading property, and consist of, for example, chromium, a chromium alloy, aluminum, an aluminum alloy, or their alloy.

The bottom gate insulating film 22, which is common to all the photo sensor elements 20, is formed on the bottom gate electrode 21 and bottom gate line 41. The bottom gate insulating film 22 has an insulating property, is translucent, and consists of, for example, silicon nitride (SiN) or silicon oxide (SiO2).

The semiconductor film 23 is formed on the bottom gate insulating film 22 for each photo sensor element 20. The semiconductor film 23 is a layer which is generally rectangular in a plan view and which is formed of amorphous silicon or polysilicon. The channel protecting film 24 is formed on the semiconductor film 23. The channel protecting film 24 has a function of protecting the interface of the semiconductor film 23 from an etchant used for patterning. The channel protecting film 24 has an insulating property, is translucent, and is made of, for example, silicon nitride or silicon oxide. The semiconductor film 23 is sensitive to light so that when light is incident on the semiconductor film 23, an amount of electron-hole pairs are generated around the interface between the channel protecting film 24 and the semiconductor film 23 in accordance with the amount of incident light. In this case, holes are generated in the semiconductor film 23 as carriers. Electrons are generated in the channel protecting film 24.

The impurities doped semiconductor film 25 is formed at one end of the semiconductor film 23 so as to partly-cover the channel protecting film 24. The impurities doped semiconductor film 26 is formed at the other end of the semiconductor film 23 so as to partly cover the channel protecting film 24. The semiconductor films 25 and 26 are pattered for each photo sensor element 20. The impurities doped semiconductor films 25 and 26 consist of amorphous silicon (n$^+$ silicon) containing n-type impurity ions.

The source electrode 27, patterned for each photo sensor element 20, is formed on the impurities doped semiconductor film 25. The drain electrode 28, patterned for each photo sensor element 20, is formed on the impurities doped semiconductor film 26. The m source lines 42, extending in the horizontal direction, are formed on the bottom gate insulating film 22 so that each of the source lines 42 corresponds to one row. The m drain lines 43, extending in the horizontal direction, are formed on the bottom gate insulating film 22 so that each of the drain lines 43 corresponds to one row. Each source line 42 is formed integrally with the source electrode 27 of one of the horizontally arranged photo sensor elements 20 which is located in the same row as that of this source line 42. Each drain line 43 is formed integrally with the drain electrode 28 of one of the horizontally arranged photo sensor elements 20 which is located in the same row as that of this drain line 43. The source electrode 27, the drain electrode 28, the source line 42, and the drain line 43 are conductive, have a shading property, and consist of, for example, chromium, a chromium alloy, aluminum, an aluminum alloy, or their alloy.

The top gate insulating film 29, which is common to all the photo sensor elements 20, is formed on the channel protecting film 24, source electrode 27, drain electrode 28, source line 42, and drain line 43. The top gate insulating film 29 has an insulating property, is translucent, and consists of, for example, silicon nitride or silicon oxide.

The top gate electrode 30 patterned for each photo sensor element 20 is formed on the top gate insulating film 29. The n top gate lines 44 extending in the vertical direction, are formed on the top gate insulating film 29 so that each of the top gate lines 44 corresponds to one column. Each top gate line 44 is formed integrally with the top gate electrode 30 of one of the vertically arranged photo sensor elements 20 which is located in the same column as that of this top gate line 44. The top gate electrode 30 and the top gate line 44 are conductive and translucent and consist of, for example, indium oxide, zinc oxide, or tin oxide, or a mixture (for example, a tin doped indium oxide or a zinc doped indium oxide) containing at least one of these elements.

The photo sensor elements 20 configured as described above are photoelectric converting elements each using the semiconductor film 23 as a light receiving section. The photo sensor elements 20 are collectively coated with a common protective insulating film 31. The protective insulating film 31 is formed on the top gate electrode 30 and top gate line 44.

The protective insulating film 31 has an insulating property, is translucent, and consists of, for example, silicon nitride or silicon oxide.

The electromagnetic shield layer 32 is formed all over the protective insulating film 31 so as to be common to all the photo sensor elements 20. The electromagnetic shield layer 32 is conductive and translucent and is formed of, for example, indium oxide, zinc oxide, or tin oxide, or a mixture containing at least one of these elements.

The overcoat layer 33 is formed all over the electromagnetic shield layer 32 so as to be common to all the photo sensor elements 20. The overcoat layer 33 is conductive and translucent and is formed of, for example, silicon nitride or silicon oxide.

The ultraviolet shielding layer 34 is formed all over the overcoat layer 33 so as to be common to all the photo sensor elements 20. The ultraviolet shielding layer 34 has a property to block ultraviolet rays that excite a fluorescent substance, described later, while allowing the passage of fluorescence (mainly visible rays) emitted by the fluorescent substance excited by ultraviolet rays. The ultraviolet shielding layer 34 includes a layer consisting of anatase or rutile type titanium oxide. The ultraviolet shielding layer 34 also includes a dielectric multilayer layer in which dielectric H layers with a large refractive index and dielectric L layers with a small refractive index are alternately stacked so as to have an optical film thickness one-fourth of an ultraviolet wavelength.

The m probe electrodes 35 extending in the vertical direction, are formed on the ultraviolet shielding layer 34 so that each of the probe electrodes 35 corresponds to one column. These probe electrodes 35 are arranged parallel with one another in a longitudinal direction. Each probe electrode 35 collectively coats the n photo sensor elements 20 in the same column.

N types of spots 60 are fixed to each probe electrode 35 in a line. A total of (m×n) types of spots 60 are arranged in a matrix. One type of spot 60 is located on one photo sensor element 20 so as to be superimposed on it in a plan view. One spot 60 is a cluster of a large number of single stranded probe DNA fragments 61. The large number of probe DNA fragments 61 contained in one spot 60 have the same base sequence (nucleotide sequence). The different spots 60 have respective base sequences of the single stranded probe DNA fragments 61. All the spots 60 have known base sequences.

Moreover, the n types of spots 60 in the same column have single stranded probe DNA fragments 61 having different base sequences but almost the same number of bases. That is, the single stranded DNA fragments in the n types of spots 60 in the same column have almost the same number of bases. The number of bases in each of the single stranded probe DNA fragments 61 in the spot 60 may vary significantly with the columns. However, the single stranded DNA fragments in adjacent ones of the m columns may have almost the same number of bases. Furthermore, a column set composed of one of the m columns of the spots 60 or a number of adjacent columns include single stranded DNA fragments 61 having almost the same number of bases. A number of column sets include single stranded DNA fragments 61 having almost the same number of bases. The spots 60 are arranged so that for the column sets each including single stranded DNA fragments 61 having almost the same number of bases, the column sets closer to the left end of the matrix have larger numbers of bases, whereas the column sets closer to the right end of the matrix have smaller numbers of bases.

Accordingly, the plurality of probe electrodes 35 are classified in accordance with the number of bases in each probe DNA fragment 61. Specifically, the plurality of probe electrodes 35 are classified into electrode sets composed of one probe electrode 35 or a number of adjacent probe electrodes 35. The spots 60 arranged in the same electrode set include single stranded probe DNA fragments 61 having almost the same number of bases but different base sequences. The expression "almost the same" as used herein means that for the number of bases in one probe DNA fragment, the plurality of spots arranged in a predetermined one of the plurality of electrode sets have the same number or the numbers for these spots are more similar to one another than those for the spots arranged on the probe electrodes other than the predetermined electrode set.

In the description below, for simplification of description, it is assumed that 81 photo sensor elements 20 are arranged in a 9×9 matrix, that nine columns of the probe electrodes 35 are formed parallel with one another, and that nine types of spots 60 are arranged on each probe electrode 35. Furthermore, the spots 60 formed on the electrode set composed of the three columns of the probe electrodes 35 from the left end of the matrix have different base sequences of the probe DNA fragments 61 but almost the same number of bases in each probe DNA fragment 61. The spots 60 formed on the electrode set composed of the central three columns of the probe electrodes 35 have different base sequences of the probe DNA fragments 61 but almost the same number of bases in each probe DNA fragment 61. The spots 60 formed on the electrode set composed of the three columns of the probe electrodes 35 from the right end of the matrix have different base sequences of the probe DNA fragments 61 but almost the same number of bases in each probe DNA fragment 61. Furthermore, the spots 60 formed on the electrode set composed of the three columns of the probe electrodes 35 from the left end of the matrix have a larger number of bases in each of the probe DNA fragments 61 than the spots 60 formed on the electrode set composed of the central three columns of the probe electrodes 35. The spots 60 formed on the electrode set composed of the central three columns of the probe electrodes 35 have a larger number of bases in each of the probe DNA fragments 61 than the spots 60 formed on the electrode set composed of the three columns of the probe electrodes 35 from the right end of the matrix. Furthermore, the probe electrode 35 in the leftmost column is defined as a first column. The probe electrode 35 in the rightmost column is defined as a ninth column. The order of each probe electrode 35 is counted from the left end of the matrix. Specifically, the first to third columns constitute the same electrode set. The fourth to sixth columns constitute the same electrode set. The seventh to ninth columns constitute the same electrode set. Within each electrode set, the single stranded probe. DNA fragments 61 have the same number of bases or the numbers of bases in one probe DNA fragment are more similar to one another than those for the spots arranged on the electrode sets other than this one.

An applicable method of fixing the spot 60 to the probe electrode 35 is to use a dispensing apparatus to spot-deposit prepared probe DNA fragments on the probe electrode 35 the surface of which has been treated using poly positive ions (poly-L-lysine, polyethyleneimine, or the like) and utilizes the charge on the DNA to electrostatically bind the DNA to the surface of the light sensing device 2.

Another fixing method uses a silane coupling agent having an amino base, an aldehyde base, or an epoxy base. In this case, the amino base, the aldehyde base, or the like is introduced onto the surface of the probe electrode 35 using a covalent bond. Accordingly, the amino base, the aldehyde base, or the like is more stably present on the probe electrode 35 than the poly positive ions.

Another fixing method introduces a labile base to synthesize oligonucleotide and spot-deposits the oligonucleotide on the surface-treated probe electrode 35 for a covalent bond.

The above DNA sensor 1 can be freely installed at and removed from the bottom of the bath 71 of the DNA reading apparatus of identifying apparatus 100 so that the spot 60 faces upward. The depth direction of the bath 71 is orthogonal to the horizontal direction.

The top of the bath 71 is open so that an electrophoresis medium 82 having a predetermined viscosity can be injected into the bath 71. The electrophoresis medium 82 is a colloid solution (gel) in which particles are dispersed in a dispersion medium, an electrolyte containing a gel, or other electrolytes.

The bath 71 is placed on a shaker 83. The shaker 83 shakes the bath 71 to agitate the electrophoresis medium 82. The shaker 83 may shake the bath 71 ultrasonically or in a rotary or reciprocative manner.

If the DNA sensor 1 is installed at the bottom of the bath 71, when the bath 71 is viewed from above, the plurality of probe electrodes 35 are arranged between the first electrode 74 and the second electrode 75. The probe electrode 35 at the left end is located closest to the first electrode 74 arranged on a left wall of the bath 71. The probe electrode 35 at the right end is located closest to the second electrode 75 provided on a right wall of the bath 71.

Temperature regulating elements 72 capable of regulating temperature are provided inside the bath on its front wall surface so that each of the temperature regulating elements 72 corresponds to one of the probe electrodes 35. Each of the temperature regulating elements 72 is provided so as to abut against an end of the corresponding probe electrode 35 if the DNA sensor 1 is installed at the bottom of the bath 71. Each temperature regulating element regulates the temperature of each of the spots 60 via the corresponding probe electrode 35. Examples of the temperature regulating element 72 include a Peltier element capable of heating and cooling or a combination of a heater capable of heating and a heat sink capable of cooling. However, the temperature regulating element 72 may be any element that can regulate the temperature of the probe electrode 35 and its vicinity by generating heat to selectively heat the probe electrode 35, while absorbing heat to selectively cool the probe electrode 35. The temperature regulating element 72 may be a heating resistor or another heating element that is only capable of heating.

A plurality of terminals 73a of a voltage control circuit 73 (shown in FIG. 5) for voltage control are disposed inside the bath 71 on its rear wall surface. Each of the terminals 73a is provided so as to contact with the corresponding probe electrode 35 if the DNA sensor 1 is installed at the bottom of the bath 71. The voltage control circuit 73 individually applies voltages to the probe electrodes 35.

Figure 5:
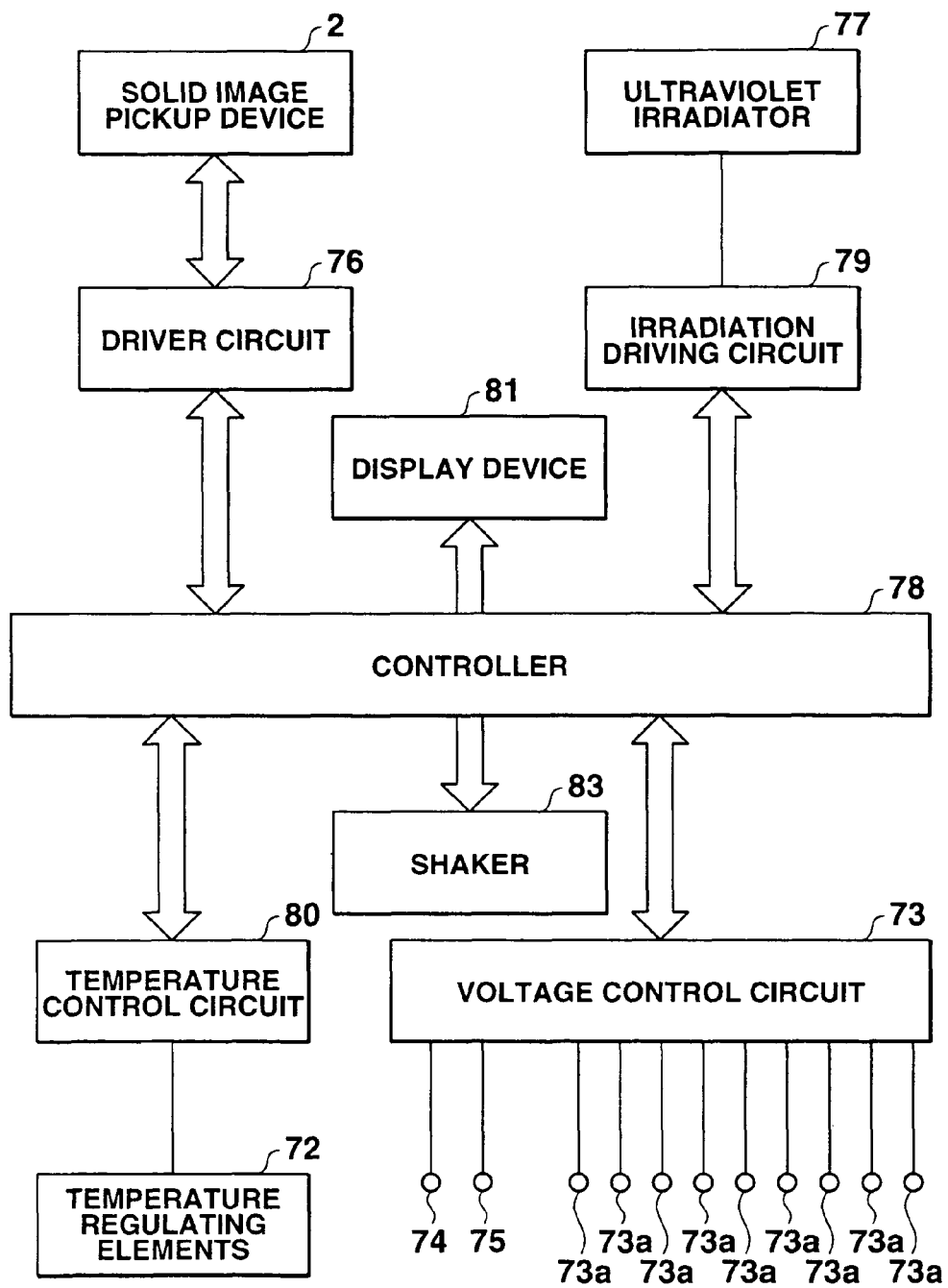
FIG. 5 is a block diagram showing a control arrangement of the DNA identifying apparatus.
Figure 6:
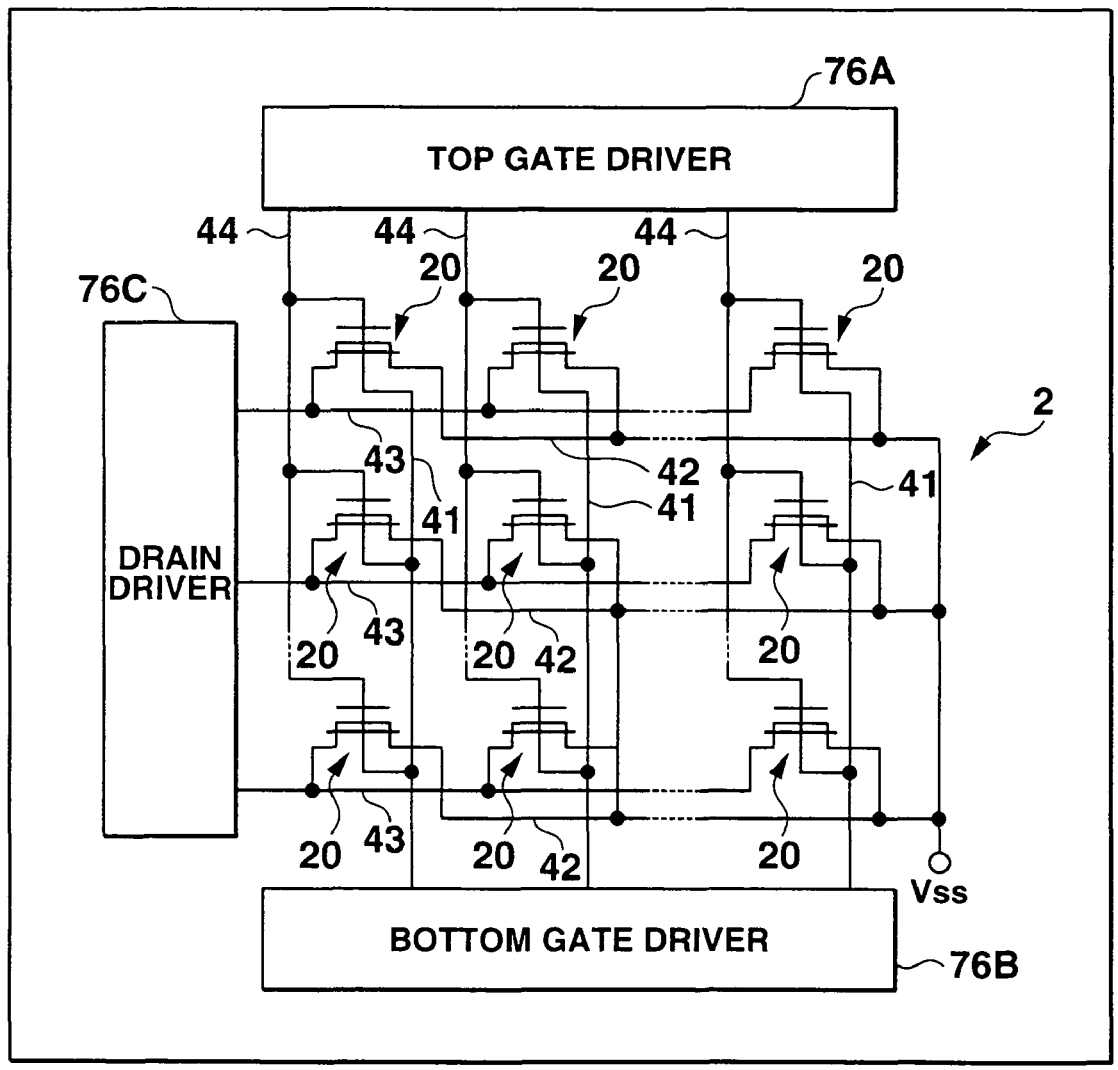
FIG. 6 is a circuit diagram showing a light sensing device and a driver circuit in the DNA identifying apparatus.

Terminals of the driver circuit 76 (shown in FIG. 5) are also disposed inside the bath 71 to drive the light sensing device 2. As shown in FIG. 6, the driver circuit 76 is including a top gate driver 76A, a bottom gate driver 76B, and a drain driver 76C. The driver circuit 76 is provided so that if the DNA sensor 1 is installed at the bottom of the bath 71, terminals of the top gate driver 76A, bottom gate driver 76B, and drain driver 76C are connected to the top gate lines 44, bottom gate lines 41, and drain lines 43, respectively. The driver circuit 76 properly applies voltages to the top gate lines 44, the bottom gate lines 41, and the drain lines 43. The source lines 42 are all maintained at a potential Vss. If the DNA sensor 1 is installed at the bottom of the bath 71, the potential Vss of the source lines 42 and electromagnetic shield layer 32 may be a ground potential.

The driver circuit 76 applies appropriate voltages to the top gate lines 44, bottom gate lines 41, and drain lines 43 at predetermined points to drive the light sensing device 2. When the light sensing device 2 is driven, the quantity of light incident on each photo sensor element 20 is converted into an electric signal. The electric signal is sensed by the driver circuit 76 to pick up an image.

Figure 7:
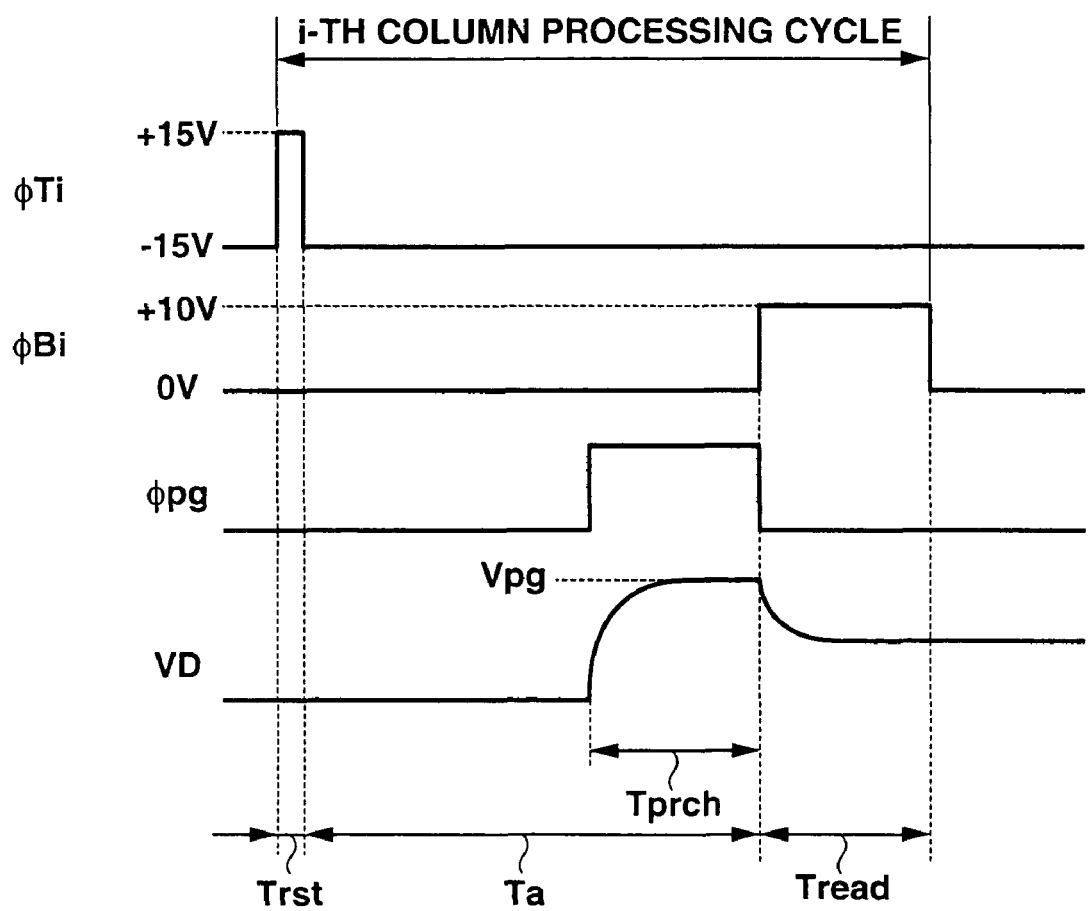
FIG. 7 is a timing chart showing an example of a basic method of drivingly controlling photo sensor elements.
Figure 9A:
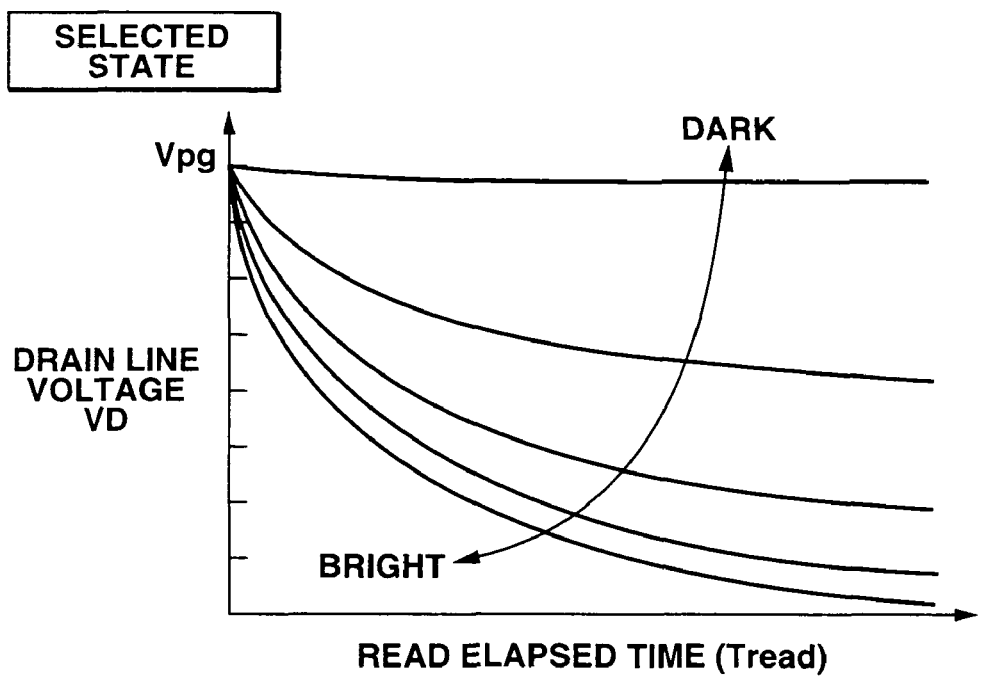
FIGS. 9A and 9B are graphs showing an optical response characteristic of an output voltage from the photo sensor element observed when the element is selected and when it is not selected, respectively.
Figure 9B:
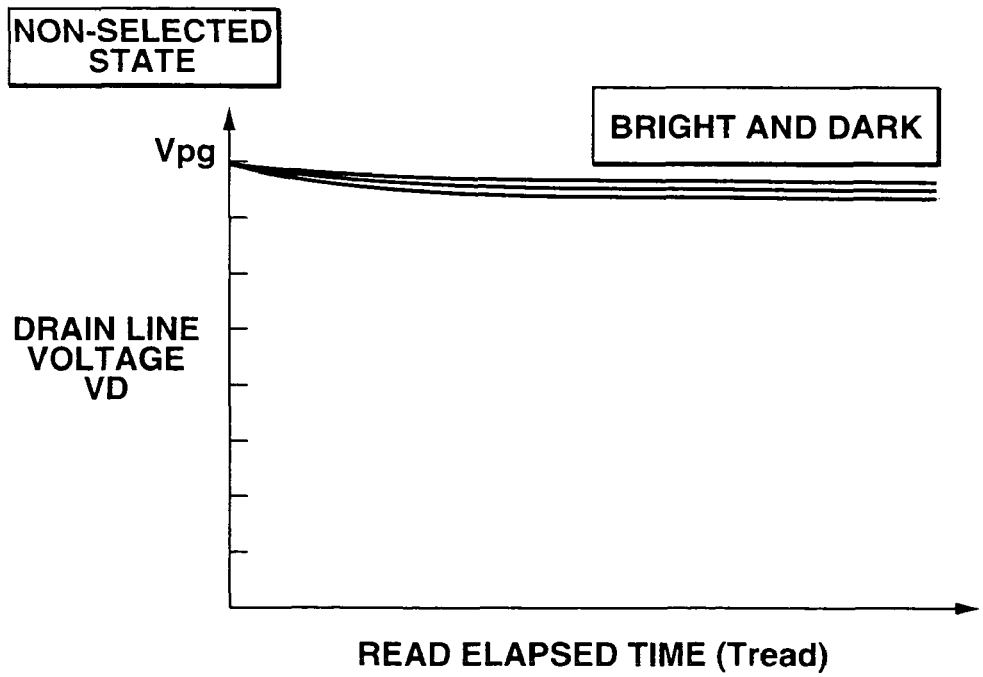

With reference to the drawings, description will be given of a method of drivingly control the above described photo sensor elements 20. FIG. 7 is a timing chart showing an example of a basic method of drivingly controlling the photo sensor elements 20. FIG. 8 is a conceptual drawing of operations of the photo sensor element 20. FIGS. 9A and 9B are graphs showing an optical response characteristic of an output voltage from the photo sensor element. Here, description will be given with reference properly to the configuration (FIGS. 1, 4A, and 4B) of the above described photo sensor element 20.

First, for a reset operation (an initializing operation), as shown in FIGS. 7 and 8A, a controller 78 provides such control as applies a pulse voltage (hereinafter referred to as a "reset pulse"; for example, a high level of Vtg=+15 V) $\phi$Ti to the top gate electrode 30 of the photo sensor element 20 in the i-th column via the top gate line 44 in an arbitrary i-th column ($1 \leq i \leq m$) to emit carriers (in this case, holes) accumulated in the semiconductor layer 23 and near the interface between the channel protecting film 24 and the semiconductor layer 23 (a reset period Trst).

Then, in a light accumulating operation (charge accumulating operation), as shown in FIGS. 7 and 8B, a low-level (for example, Vtg=-15 V) bias voltage $\phi$Ti is applied to the top gate electrode 30 of the photo sensor element 20 in the i-th row via the top gate line 44 in the i-th column to end the reset operation to start a light accumulation period Ta based on a carrier accumulating operation. During the light accumulation period Ta, electron-hole pairs are generated in an incident effective area of the semiconductor layer 23, that is, in a carrier generation area in accordance with the quantity of light incident from the top gate electrode 30. Then, the holes of the electron-hole pairs are accumulated in the semiconductor layer 23 and near the interface between the channel protecting film 24 and the semiconductor layer 23, that is, around the periphery of a channel area.

Then, in a precharge operation, concurrently with the light accumulation period Ta, each drain line 43 is caused to hold charges in order to apply a predetermined voltage (precharge voltage) Vpg to the drain electrode 28 of the photo sensor element 20 in the i-th column on the basis of a precharge signal $\phi$pg as shown in FIGS. 7 and 8C. Then, in a read operation, as shown in FIGS. 7 and 8D, after a precharge period Tprch has passed, a high-level (for example, Vbg=+10 V) bias voltage (a read selection signal; hereinafter referred to as a "read pulse") $\phi$Bi is applied to the bottom gate electrode 21 (a selection state) to turn on the photo sensor element 20 (a read period Tread).

In this case, during the read period Tread, the carriers (holes) accumulated in the channel area of the photo sensor element 20 on which light has been incident serve to reduce the Vtg (-15 V) applied to the top gate electrode 30, having an opposite polarity. Accordingly, the Vbg (+15 V) of the bottom gate electrode causes an n channel to be formed. The voltage (drain voltage) VD of the drain electrode 28 and drain line 43 tends to decrease gradually from the precharge voltage Vpg as the time elapses, as shown in FIG. 9A.

Specifically, if the light accumulation during the light accumulation period Ta is in a bright state, then as shown in FIG. 8D, an amount of carriers (holes) are captured in the channel area in accordance with the quantity of incident light to cancel the negative bias of the top gate electrode 30, so that the positive bias of the bottom gate electrode corresponding to the cancellation turns on the photo sensor element 20. Then, the drain voltage VD decreases in accordance with on resistance dependent on the quantity of incident light, as shown in FIG. 9A.

On the other hand, if the light accumulation is in a dark state and no carriers (holes) are accumulated in the channel area, then as shown in FIG. 8E, the negative bias of the top gate electrode 30 cancels the positive bias of the bottom gate electrode 21 to turn of the photo sensor element 20. As shown in FIG. 9A, the drain voltage VD is held almost as it is.

Accordingly, as shown in FIG. 9A, the tendency to vary the drain voltage VD is closely associated with the quantity of light received during the time (light accumulation time Ta) from the end of a reset operation based on the application of the reset pulse φTi to the top gate electrode 30 to the application of the read pulse φBi to the bottom gate electrode 21. If a large amount of carriers are accumulated (bright state), the drain voltage VD tends to decrease rapidly. On the other hand, if only a small amount of carriers are accumulated (dark state), the drain voltage VD tends to decrease slowly. Thus, the quantity of light (emitted light) incident on the photo sensor element 20 is converted by detecting the drain voltage VD (=Vrd) a predetermined time after the read period Tread has started or detecting the time required to reach a predetermined threshold voltage set as a reference.

In the timing chart shown in FIG. 7, after the precharge period Tprech has passed, as shown in the low level (for example, Vbg=0 V) continues to be applied to the bottom gate electrode 21 to keep the photo sensor element 20 on as shown in FIGS. 8F and 8G. Thus, as shown in FIG. 9B, the drain voltage VD is maintained at a value similar to the precharge voltage Vpg. In this manner, the application of the voltage to the bottom gate voltage 21 achieves a selecting function of switching the read state of the photo sensor element 20 so that the photo sensor element 20 is selected to be read or is not selected to be read.

The first electrode 74 is provided inside the bath 71 on the upper part of the left wall surface. The second electrode 75 is provided inside the bath 71 on the upper part of the right wall surface. The electrodes 74 and 75 are exposed inside the bath 71. The electrodes 74 and 75 are also located above the probe electrodes 35, positioned at the bottom of the bath 71. The voltage control circuit 73 individually applies voltages to the electrodes 74 and 75.

If the DNA sensor 1 is installed at the bottom of the bath 71, when the bath 71 is viewed from above (in a height direction of the bath 71), the light sensing device 2 is located between the first electrode 74 and the second electrode 75. If the DNA sensor 1 is installed at the bottom of the bath 71, when the bath 71 is viewed from the right or left (in a width direction of the bath 71), the light sensing device 2 is located below the first electrode 74 and second electrode 75.

The ultraviolet irradiator 77 is provided above the bath 71 to emit light downward. Light emitted by the ultraviolet irradiator 77 has an ultraviolet wave range and almost none of a fluorescent wave range.

Now, a control arrangement of the DNA identifying apparatus 100 will be described with reference to FIG. 5.

The DNA identifying apparatus 100 includes a display device 81, the controller 78 responsible for general control, an irradiation driving circuit 79 that drives the ultraviolet irradiator 77, and a temperature control circuit 80 that drives the temperature regulating elements 72.

The controller 78 is an exclusive logic circuit or an arithmetic processing device having a CPU (Central Processing Unit) or the like. The controller 78 operates the voltage control circuit 73, the driver circuit 76, the irradiation driving circuit 79, the temperature control circuit 80, the display device 81, and the shaker 83.

As described with reference to FIGS. 6, 9A, and 9B, in response to an instruction from the controller 78, the driver circuit 76 drives the light sensing device 2 to cause the light sensing device 2 to perform an image pickup operation. An image picked up by the light sensing device 2 is subjected by the driver circuit 76 to an A/D conversion. The driver circuit 76 then outputs the converted image to the controller 78.

In response to an instruction from the controller 78, the irradiation driving circuit 79 drives the ultraviolet irradiator 77 to cause the ultraviolet irradiator 77 to perform a light emitting operation.

In response to an instruction from the controller 78, the temperature control circuit 80 drives the temperature regulating elements 72 to cause the temperature regulating elements 72 to perform a heating or cooling operation.

In response to an instruction from the controller 78, the voltage control circuit 73 individually applies voltages to the first electrode 74 and second electrode 75.

In response to an instruction from the controller 78, the display device 81 displays an image picked up by the light sensing device 2.

Figure 10:
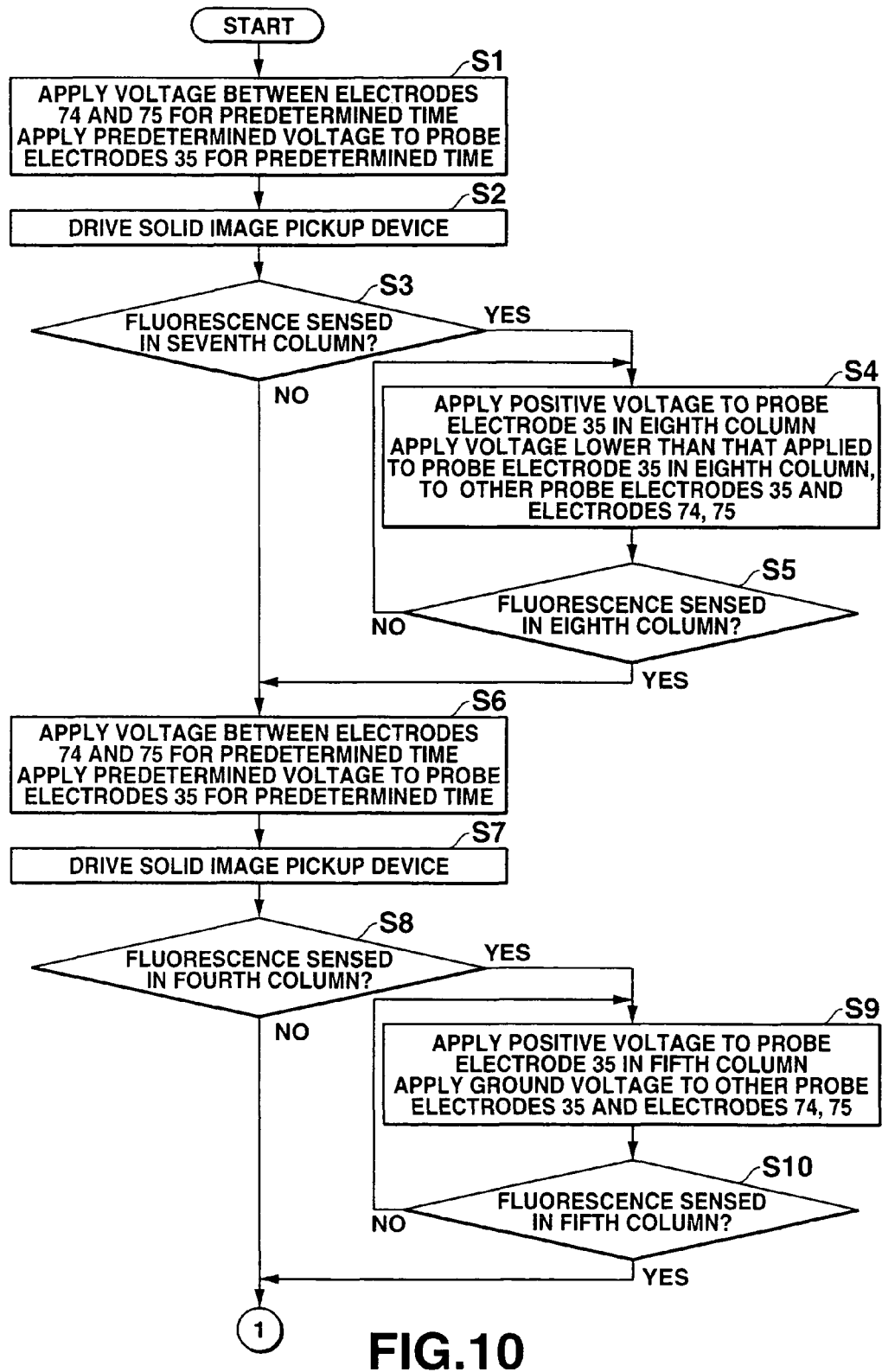
FIG. 10 is a flow chart showing operations of the DNA identifying apparatus.
Figure 11:
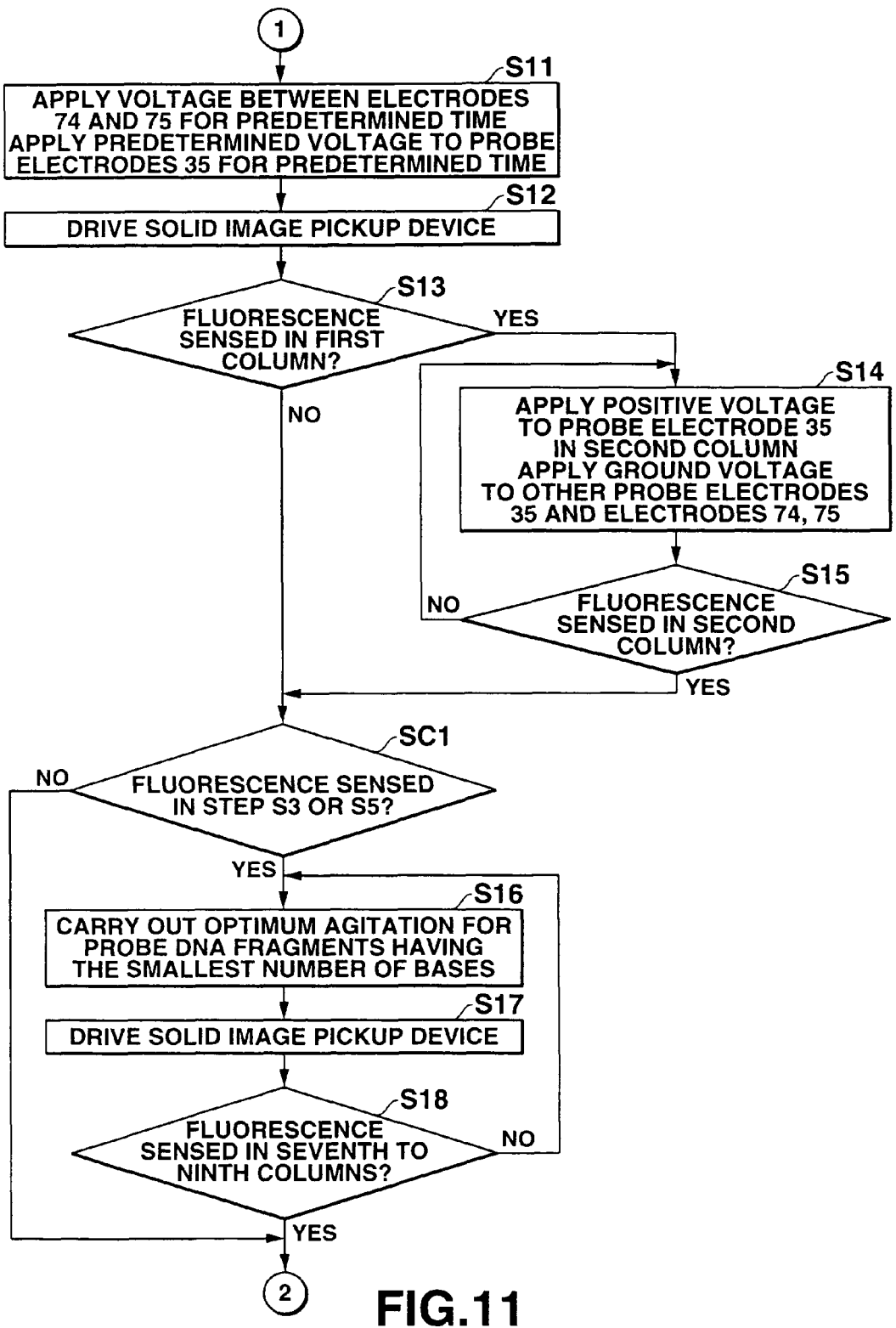
FIG. 11 is a flow chart showing a continued part of FIG. 10.
Figure 12:
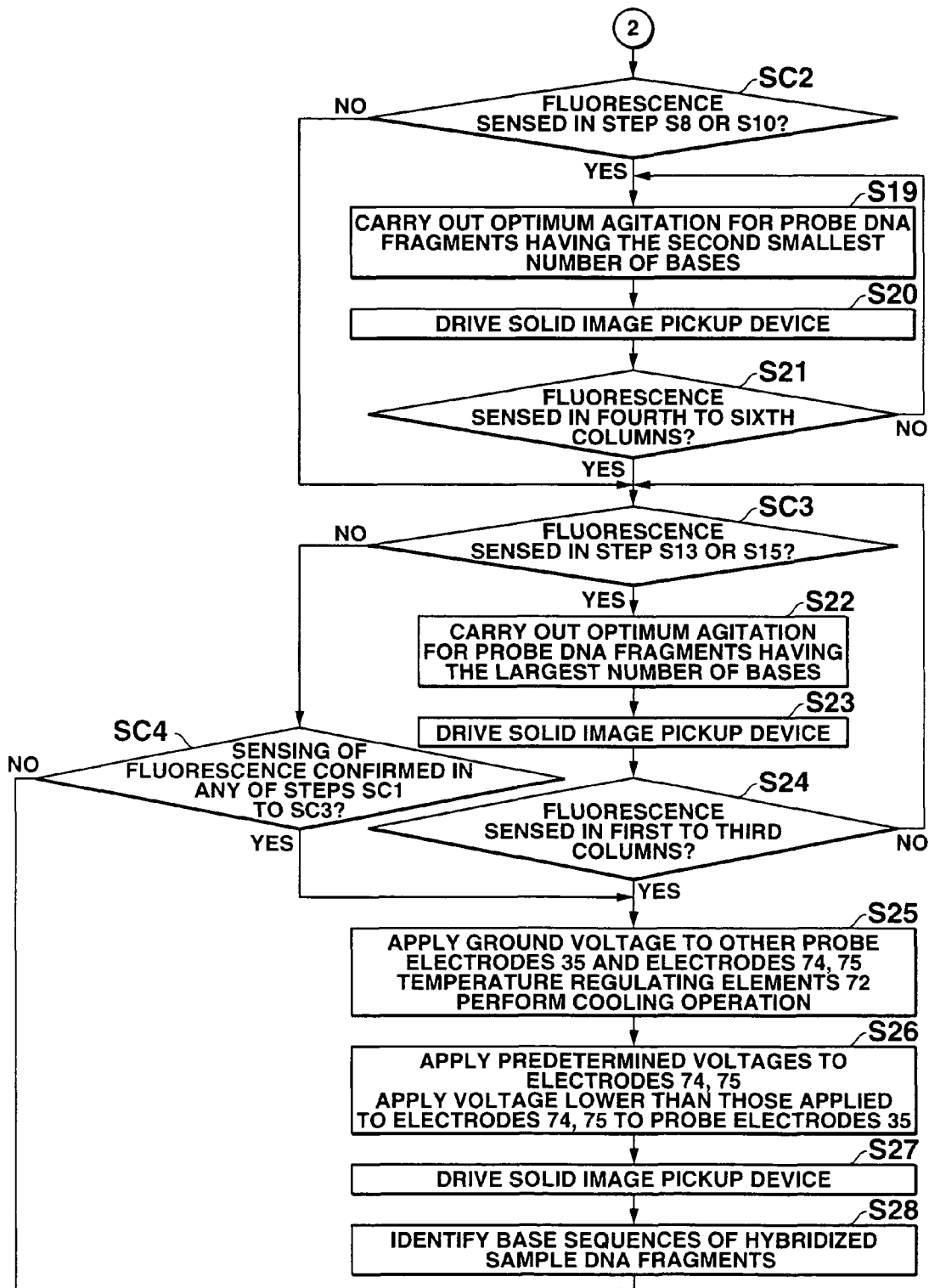
FIG. 12 is a flow chart showing a continued part of FIG. 11.

Now, operations of the DNA identifying apparatus 100 will be described with reference to FIGS. 10 to 12. FIGS. 10 to 12 are flow charts showing the flow of operations of the DNA identifying apparatus 100.

First, DNAs are extracted from a specimen and denatured to obtain plural types of single stranded DNA fragments having different numbers of bases. These DNA fragments may include plural types of single stranded DNA fragments having the same number of bases and different base sequences. A fluorescent substance is bonded to each of the single stranded DNA fragments so that the single stranded DNA fragment is labeled with the fluorescent substance. The single stranded DNA fragments obtained are called sample DNA fragments. The fluorescent substance with which the sample DNA fragment is labeled may be, for example, Cy2 or Cy3 of CyDye (manufactured by Amersham Biosciences). The fluorescent substance is selected to be excited at the wavelength of ultraviolet rays emitted by the ultraviolet irradiator 77 of the DNA identifying apparatus 100. The fluorescent substance emits fluorescence when excited by ultraviolet rays. The wavelength of the fluorescence is such that carriers is preferably generated in the semiconductor film 23 of the photo sensor element 20 and is larger than that of ultraviolet rays.

Then, the DNA sensor 1 is installed at the bottom of the bath 71, and the electrophoresis medium 82 is injected into the bath 71.

Then, the DNA identifying apparatus 100 is powered on and thus activated.

The controller 78 of the DNA identifying apparatus controls the temperature control circuit 80. In accordance with the instruction from the controller 78, the temperature control circuit 80 drives the temperature regulating elements 72 to perform a heating operation. Thus, the temperature regulating elements 72 generate heat to transmit the heat from the temperature regulating elements 72 to the corresponding probe electrodes 35. As the temperature regulating elements 72 heat the probe electrodes 35, the electrophoresis medium 82 in the bath 71 is also heated to 95° C. or higher. The temperature control circuit 80 subsequently controls the temperature regulating elements 72 in accordance with an instruction from the controller 78 to maintain the electrophoresis medium 82 at 95° C. or higher. Heating the electrophoresis medium 82 at 95° C. or higher prevents some of the probe DNA fragments 61 in one spot 60 from being hybridized.

The temperature at which the electrophoresis medium 82 is maintained is not limited to 95° C. or higher but has only to be such that the single stranded DNA fragments maintain single strands without being complementarily bonded together. Alternatively, a temperature detector may be provided inside the bath 71 to detect the temperature of the electrophoresis medium 82. The temperature detected by the temperature detector may be fed back to the controller 78, which then controls the temperature control circuit 80 in accordance with the detected temperature. Then, the temperature control circuit 80 may control the temperature regulating elements 72 so that the electrophoresis medium 82 is maintained at 95° C. or higher.

The plural types of single stranded DNA fragments thus obtained are poured into the bath 71 from its top. However, the sample DNA fragments are not dispersed all over the interior of the bath 71 but are poured into an area of the interior of the bath 71 which is closer to the first electrode 74 and in which no probe electrodes 35 are present in a plan view (see FIGS. 1 and 2). In particular, the sample DNA fragments are gently poured so as not to disperse to areas located away from the first electrode 74. At this time, the single stranded DNA fragments may be injected into the bath 71 together with a solution partly containing a reagent used for PCR amplification. Of the plural types of single stranded DNA fragments, FIG. 1 shows a single stranded DNA fragment 151 having the smallest number of bases, a single stranded DNA fragment 153 having the largest number of bases, and a single stranded DNA fragment 152 having more bases than the single stranded DNA fragment 151 and less bases than the single stranded DNA fragment 153.

Since the temperature regulating elements 72 have generated heat to heat the electrophoresis medium 82 to 95° C. or higher, the sample DNA fragments are prevented from being partially hybridized and bonded together even if some of them have a complementary base sequence. Consequently, the sample DNA fragments are completely fragmented before migrating through the electrophoresis medium 82.

Then, as shown in step S1 (a first voltage applying step) in FIG. 10, the controller 78 controls the voltage control circuit 73. Accordingly, in accordance with an instruction from the controller 78, the voltage control circuit 73 applies a voltage between the first electrode 74 and the second electrode 75 so that the potential of the first electrode 74 is lower than that of the second electrode 75. At the same time, in accordance with an instruction from the controller 78, the voltage control circuit 73 applies voltages to the probe electrodes 35 so that the potentials of all the probe electrodes 35 are equal to or lower than that of the second electrode 75 and preferably than that of the first electrode 74. Thus, the first electrode 74 forms a cathode, while the second electrode 75 forms an anode. All the probe electrodes 35 have a negative or equal voltage with respect to the second electrode 75. In this case, the first electrode 74 desirably has a ground potential. The probe electrodes 35 desirably have an equal or negative voltage with respect to the first electrode 74. The voltage of each probe electrode 35 with respect to the first electrode 74 is equal to or higher than a voltage required to separate a sample DNA fragment mis-hybridized to a probe DNA fragment from this probe DNA fragment and is equal to or lower than a voltage at which a sample DNA fragment completely hybridized to the corresponding probe DNA fragment is not separated from this probe DNA fragment. The term "mis-hybridization" as used herein means partial hybridization in which if a part of the base sequence of one of a sample DNA fragment and a probe DNA fragment is complementary to a part or the whole of the base sequence of the other, the sample DNA fragment and the probe DNA fragment are partly bonded together. The complete hybridization means that all the bases of a sample DNA fragment are complementarily bonded to all the bases of the corresponding probe DNA fragment.

Figure 13:
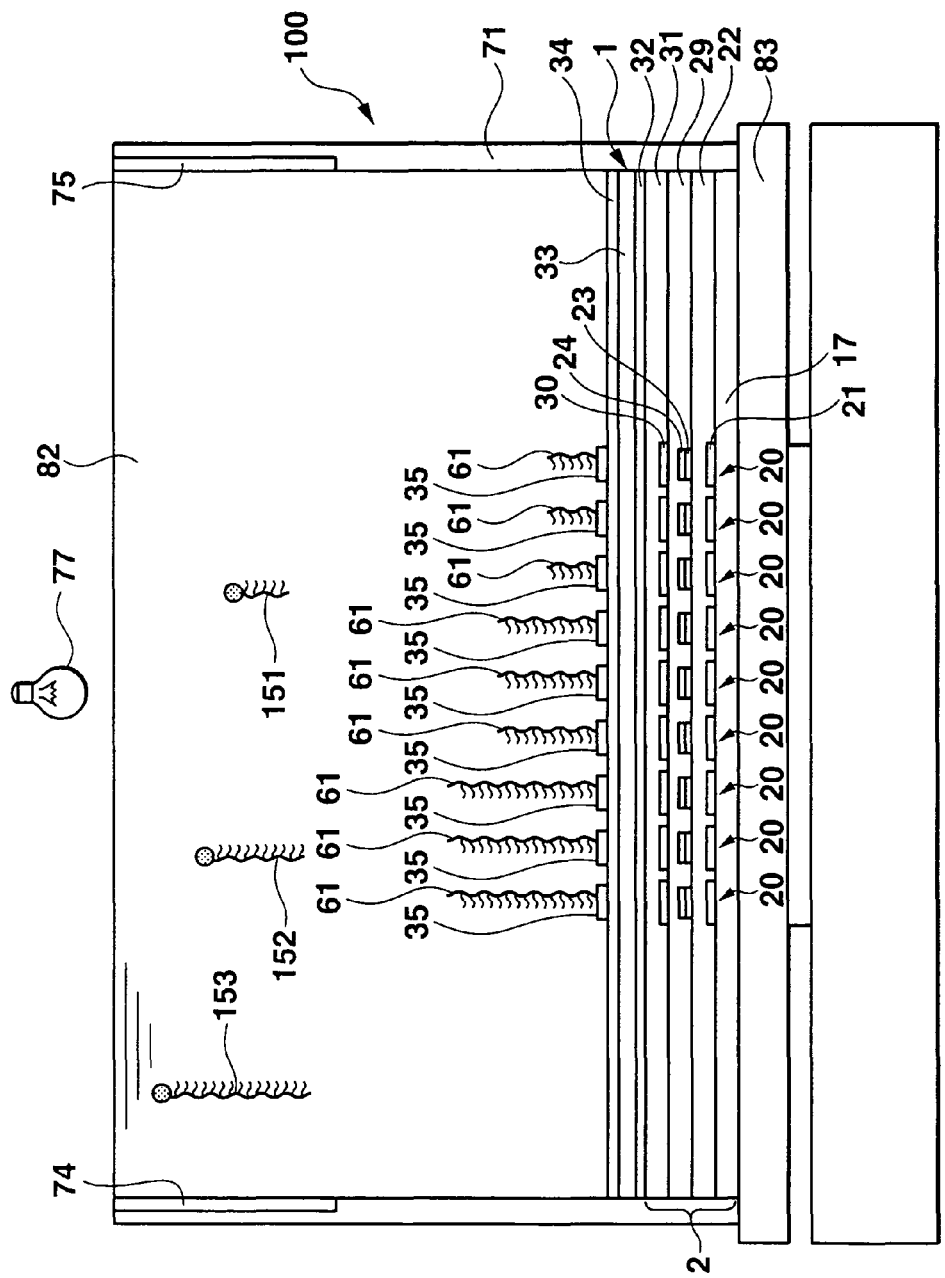
FIG. 13 is a diagram showing the distribution of sample DNA fragments in a bath during the operation of the DNA identifying apparatus, together with the DNA identifying apparatus.

Thus, the plural types of sample DNA fragments migrate through the electrophoresis medium 82, notably through a surface layer of the electrophoresis medium 82 toward the second electrode 75. In this case, the voltage control circuit 73 maintains the above voltage state for a predetermined time. An application time and the applied voltage are such that a sample DNA fragment with a relatively small volume which is comparable to that of the probe DNA fragments 61 in the seventh to ninth columns owing to almost the same number of bases as that in each of these probe DNA fragments migrates onto the probe electrode 35 in the seventh column. Accordingly, as shown in FIG. 13, if the sample DNA fragment 151 with the smallest number of bases has almost the same number of bases as that in each of the probe DNA fragments 61 in the seventh to ninth columns, the sample DNA fragment 151 migrates onto the probe DNA fragment 35 in the seventh column. However, since the sample DNA fragments 152 and 153 have larger volumes than the sample DNA fragment 151, they offer higher fluid resistances than the sample DNA fragment 151 during electrophoresis and thus do not migrate onto the probe DNA fragment in the seventh column.

In this case, even if voltages are applied to the probe electrodes 35, electric fields from the probe electrodes 35 do not affect the operations of the photo sensor elements 20 because the grounded electromagnetic shield layer 32 is provided between the probe electrodes 35 and the photo sensor elements 20.

After a predetermined time within which a sample DNA fragment having the same number of bases as that in each of the probe DNA fragments 61 in the seventh to ninth columns is expected to reach a part of the electrophoresis medium 82 located above the probe DNA fragment 61 in the seventh column, the voltage control circuit 73 clears the voltage application state to set the first electrode 74, second electrode 75, and all probe electrodes 35 to have an equal voltage. Then, the controller 78 controls the driver circuit 76 and the irradiation driving circuit 79. In accordance with an instruction from the controller 78, the driver circuit 76 drives the light sensing device 2 according to the above described method of drivingly controlling the photo sensor elements 20. Furthermore, the irradiation driving circuit 79 drives the ultraviolet irradiator 77 in accordance with an instruction from the controller 78 (step S2).

Thus, the ultraviolet irradiator 77 emits light, and the ultraviolet rays emitted by the ultraviolet irradiator 77 are applied all over the surface of the electrophoresis medium 82. Thus, the ultraviolet rays are incident on the fluorescent substance attached to the sample DNA fragments suspended in the electrophoresis medium 82 above the probe DNA fragments 61 in the seventh to ninth columns. The fluorescent substance thus emits fluorescence, which passes through the ultraviolet blocking layer 34, overcoat layer 33, the electromagnetic shield layer 32, the protective insulating film 31, the top gate electrode 30, the top gat insulating film 29, and the channel protecting film 24 to enter the semiconductor film 23. Each of the photo sensor elements 20 photoelectrically converts the fluorescence incident on its semiconductor film 23 into an electric signal in accordance with the intensity of the fluorescence or the quality of light. The light sensing device 2 then uses each photo sensor element 20 to sense the intensity of the fluorescence or the quantity of light to obtain the two-dimensional distribution of fluorescence intensities in the form of a two-dimensional image. The image acquired by the light sensing device 2 is subjected by the driver circuit 76 to an A/D conversion and is then outputted by the driver circuit 76 to the controller 78 as image data.

In this case, the provision of the ultraviolet blocking layer 34 prevents the ultraviolet rays emitted by the ultraviolet irradiator 77 from entering the photo sensor elements 20. The photo sensor elements 20 do not substantially photoelectrically convert the ultraviolet rays.

On the basis of the image data inputted by the driver circuit 76 in the above step S2, the controller 78 determines whether or not the photo sensor element 20 in the seventh column senses the fluorescence (step S3).

If any of the plural types of sample DNA fragments has almost the same number of bases as that in each of the probe DNA fragments 61 in the seventh to ninth columns, the sample DNA fragment 151 having almost the same number of bases and the relatively small volume migrates onto the probe electrode 35 in the seventh column in the above step S1 as shown in FIG. 13. Accordingly, if any of the plural types of sample DNA fragments has almost the same number of bases as that in each of the probe DNA fragments 61 in the seventh to ninth columns, the fluorescence emitted by this sample DNA fragment is incident on the semiconductor film 23 of the photo sensor element 20 in the seventh column with a high intensity. Thus, in the above step S3, the controller 78 determines that the photo sensor element 20 in the seventh column has sensed the fluorescence (step S3: Yes), the processing by the controller 78 shifts to step S4. On the other hand, if none of the plural types of sample DNA fragments have almost the same number of bases as that in each of the probe DNA fragments 61 in the seventh to ninth columns, almost none of the sample DNA fragments have almost the same number of bases and thus the relatively small volume. Accordingly, fluorescence of a low intensity or almost no fluorescence is incident on the semiconductor film 23 of the photo sensor element 20 in the seventh row. Consequently, the photo sensor element 20 in the seventh column does not sense the fluorescence in the above step S3. The controller 78 thus determines that no sample DNA fragments have almost the same number of bases as that in each of the probe DNA fragments 61 in the seventh to ninth columns (step S3: No). The processing by the controller 78 shifts to step S6.

Figure 14:
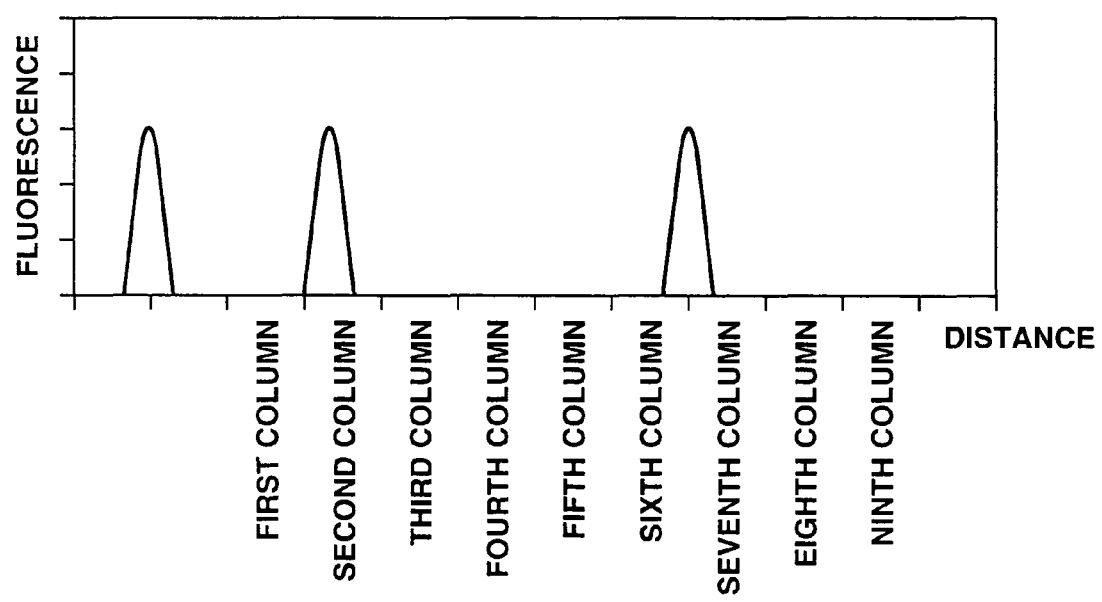
FIG. 14 is a graph showing the distribution of fluorescence intensities based on the distribution of the sample DNA fragments in FIG. 13.

FIG. 13 is a view showing a position through which the sample DNA fragment 151 with the relatively small volume migrates in the above step S1 if the sample DNA fragment 151 has almost the same number of bases as that in each of the probe DNA fragments 61 in the seventh to ninth columns. FIG. 14 is a graph representing the distribution of fluorescence intensities in an image acquired by the light sensing device 2 when the sample DNA fragment 151 having the relatively small volume and almost the same number of bases as that in each of the probe DNA fragments 61 in the seventh to ninth columns electrically migrates to the vicinity of the seventh column of the probe DNA fragments 61.

In step S4, the controller 78 controls the voltage control circuit 73. Thus, in accordance with an instruction from the controller 78, the voltage control circuit 73 applies voltages so that the potential of the probe electrode 35 in the eighth column is higher than those of the other probe electrodes 35 and first electrode 74. In this case, the probe electrodes 35 other than the one in the eighth column and the first electrode 74 have a ground potential. The probe electrode 35 in the eighth column has a positive voltage. The probe electrode 35 in the eighth column has a positive voltage with respect to the potentials of the probe electrodes 35 other than the one in the eighth column and of the first electrode 74. Such a high voltage causes the selection of the electrode set composed of the probe electrodes 35 in the seventh to ninth columns. Thus, in spite of the voltage between the first electrode 74 and the second electrode 75, the sample DNA fragment 151 having almost the same number of bases as that in each of the probe DNA fragments 61 in the seventh to ninth columns and thus having the relatively small volume can be held close to the probe electrode 35 in the eighth column, that is, close to the probe DNA fragments 61 in the seventh to ninth columns. In step S4 and step S5, described later, the potential of the second electrode 75 is preferably also equal to that of the first electrode 74 because this prevents the sample DNA fragments from moving from the first electrode 74 to the second electrode 75.

Then, the controller 78 controls the driver circuit 76. Thus, the driver circuit 76 drives the light sensing device 2 so that the light sensing device 2 acquires an image representing the distribution of fluorescence intensities while the ultraviolet irradiator 77 is emitting light. The driver circuit 76 then outputs the image data to the controller 78. Then, on the basis of the image data, the controller 78 determines whether or not the photo sensor element 20 in the eighth column has sensed the fluorescence (step S5).

Figure 15:
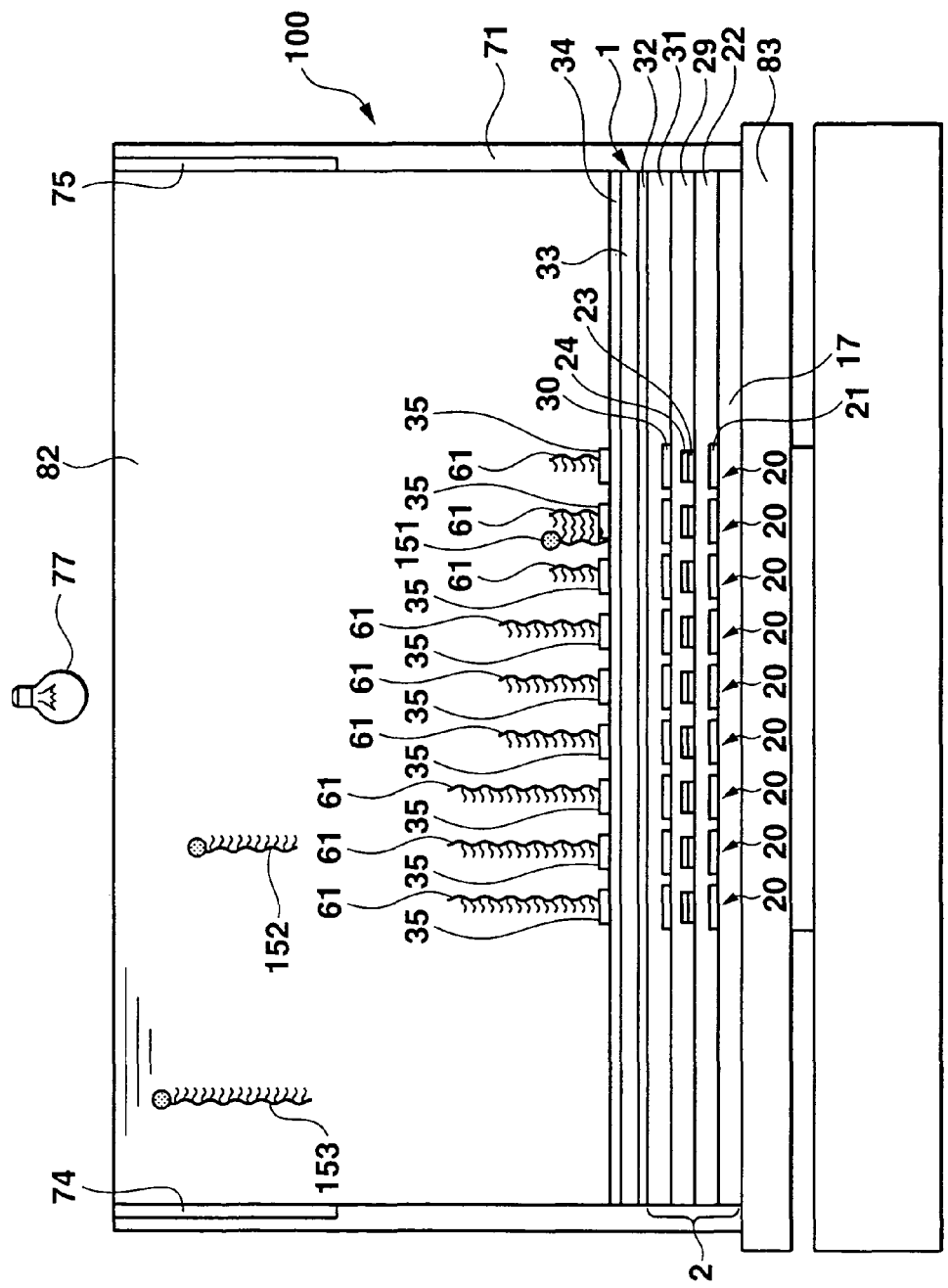
FIG. 15 is a diagram showing the distribution of the sample DNA fragments in the bath during the operation of the DNA identifying apparatus, together with the DNA identifying apparatus.

In this case, if in the above step S4, a voltage higher than that of the first electrode 74 is applied to the probe electrode 35 in the eighth column, a sample DNA fragment having almost the same number of bases in the probe DNA fragments 61 in the seventh to ninth columns migrates so as to sink from the top of the probe electrode 35 in the seventh column toward the probe electrode 35 in the eighth column. Accordingly, once the sample DNA fragment 151 having almost the same number of bases as that in each of the probe DNA fragments 61 in the seventh to ninth columns and thus having the relatively small volume migrates to the vicinity of the probe electrode 35 in the eighth column, the fluorescence emitted by this sample DNA fragment is incident on the semiconductor film 23 of the photo sensor element 20 in the eighth column with a high intensity as shown in FIG. 15. Thus, in the above step S5, the controller 78 determines that the photo sensor element 20 in the eighth column has sensed the fluorescence (step S5: Yes), the processing by the controller 78 shifts to step S6. Step S4 is intended to hold, close to the probe electrode 35 in the eighth column, the sample DNA fragment 151 having almost the same number of bases as that in each of the probe DNA fragments 61 in the seventh to ninth columns and thus having the relatively small volume. At this stage, the probe DNA fragments 61 in the seventh to ninth columns need not necessarily be hybridized to the sample DNA fragment 151 with the relatively small volume. On the other hand, if the sample DNA fragment having almost the same number of bases as that in each of the probe DNA fragments 61 in the seventh to ninth columns has not migrated to the vicinity of the probe electrode 35 in the eighth column, then the controller 78 determines in step S5 that the photo sensor element 20 in the eighth column has not sensed the fluorescence (step S5: No). Then, the processing by the controller 78 shifts to step S4. The processing by the controller 78 is repeated in order of step S5: No and step S4 to continuously apply a voltage higher than that of the first electrode 74 to the probe electrode 35 in the eighth column until the sample DNA fragment 151 with the relatively small volume migrates to the vicinity of the probe electrode 35 in the eighth column.

Figure 16:
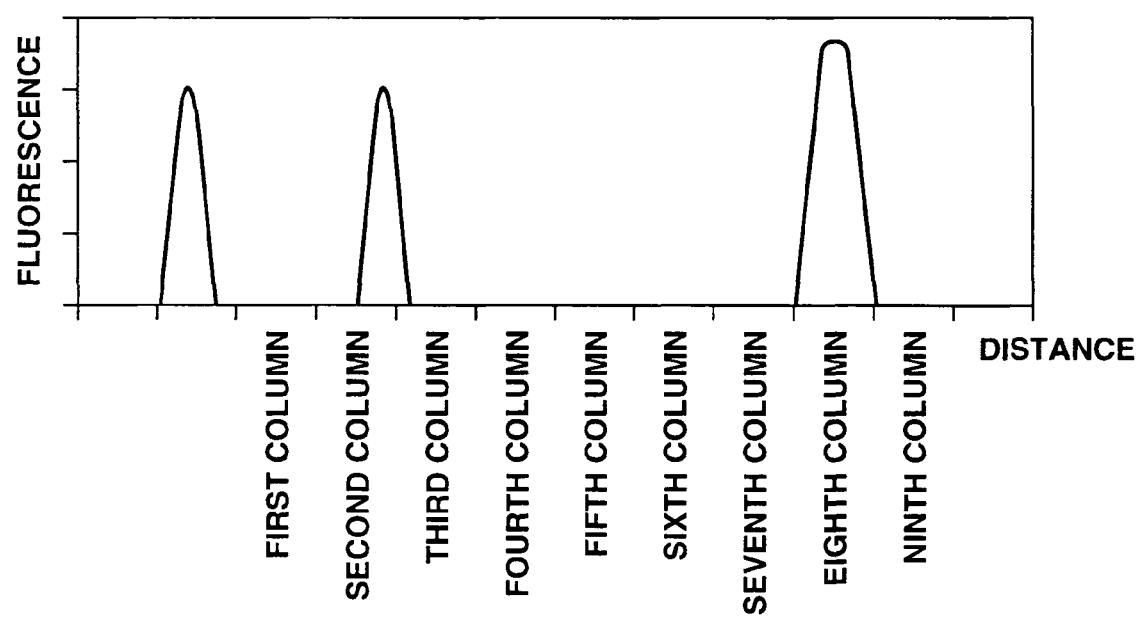
FIG. 16 is a graph showing the distribution of fluorescence intensities based on the distribution of the sample DNA fragments in FIG. 15.

FIG. 15 is a view showing a position through which the sample DNA fragment 151 having almost the same number of bases as that in each of the probe DNA fragments 61 in the seventh to ninth columns and thus having the relatively small volume migrates in the above step S4. FIG. 16 is a graph representing the distribution of fluorescence intensities in an image acquired by the light sensing device 2 if the sample DNA fragment 151 has almost the same number of bases as that in each of the probe DNA fragments 61 in the seventh to ninth columns.

In step S6 (second voltage applying step), in accordance with an instruction from the controller 78, the voltage control circuit 73 applies a voltage between the first electrode 74 and the second electrode 75 so that the potential of the first electrode 74 is lower than that of the second electrode 75. At the same time, in accordance with an instruction from the controller 78, the voltage control circuit 73 applies voltages to the probe electrodes 35 so that the potentials of the probe electrodes 35 other than the one in the eighth column remain equal to or lower than that of the second electrode 75, desirably equal to or lower than that of the first electrode 74 until immediately before step S16. The voltage control circuit 73 also keeps the potential of the probe electrode 35 in the eighth column equal to or higher than the voltage applied to the first electrode 74 and equal to or lower than the voltage applied to the second electrode 75 until immediately before step S16. However, the potential of the probe electrode 35 in the eighth column is desirably equal to that of the second electrode 75 in order to hold the sample DNA fragment 151.

Figure 17:
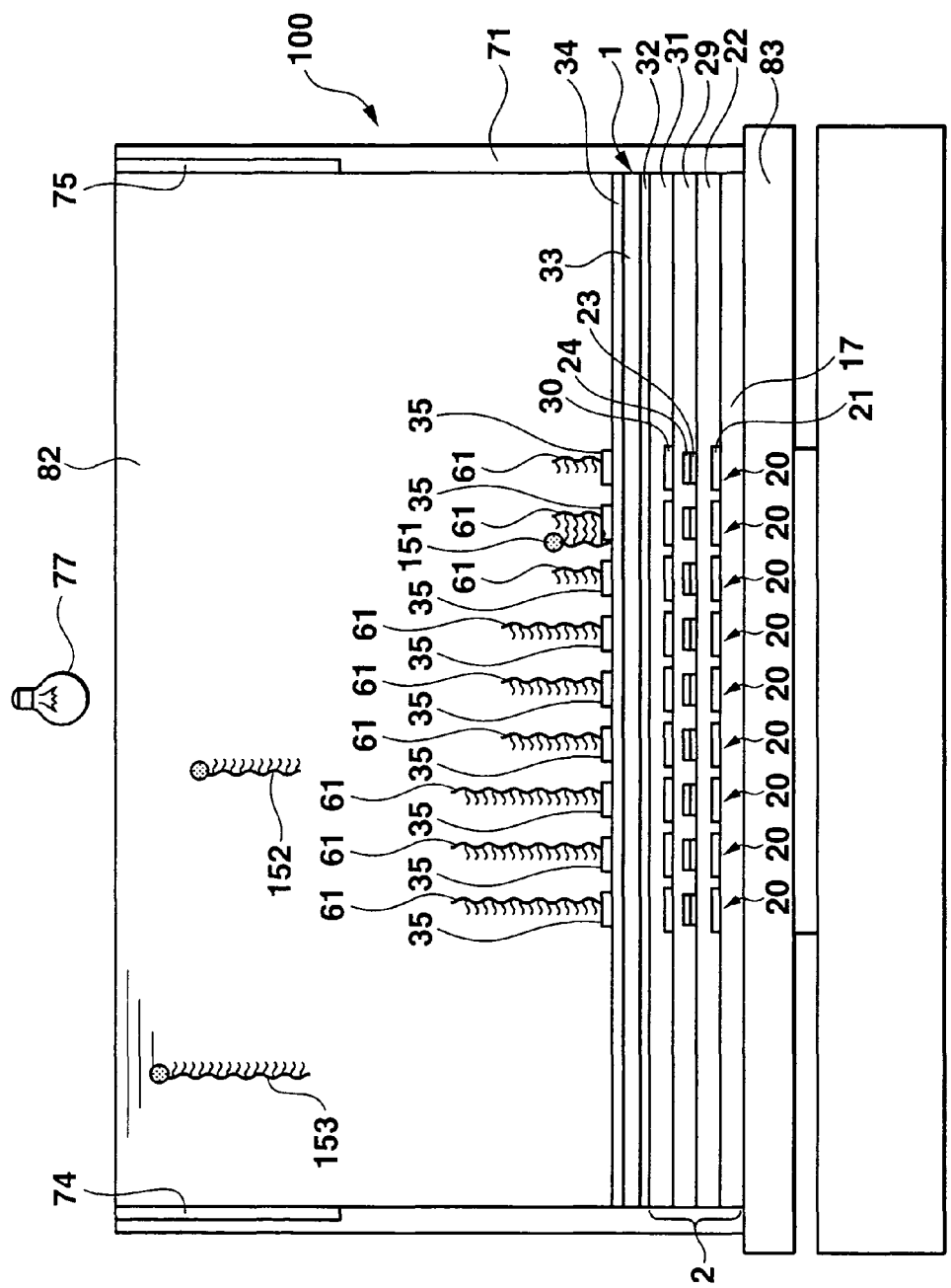
FIG. 17 is a diagram showing the distribution of the sample DNA fragments in the bath during the operation of the DNA identifying apparatus, together with the DNA identifying apparatus.

Thus, the sample DNA 152 having a relatively medium volume and the sample DNA fragment 153 having a relatively large volume migrate through the electrophoresis medium 82 toward the second electrode 75; both sample DNA fragments are present in the surface layer of the electrophoresis medium 82. However, the sample DNA 152 having the relatively medium volume offers a relatively lower fluid resistance than the sample DNA fragment 153 having the relatively large volume. Consequently, the sample DNA 152 having the relatively medium volume migrates at a higher speed than the sample DNA fragment 153 having the relatively large volume. In this case, the voltage control circuit 73 maintains the above voltage state for a predetermined time. The application time and the applied voltage are such that the sample DNA fragment 152 having the relatively medium volume migrates onto the probe electrode 35 in the fourth column. On this occasion, the sample DNA fragment 153 having the relatively large volume has not arrived on the probe electrode 35 in the fourth column. Accordingly, as shown in FIG. 17, if the sample DNA fragment 152 has almost the same number of bases as that in each of the probe DNA fragments 61 in the fourth to sixth columns, the sample DNA fragment 152 migrates onto the fourth column. Furthermore, the sample DNA fragment 151 having the relatively small volume has been held, since the previous step S4, close to the probe electrode 35 in the eighth column by electric fields from this probe electrode 35, so as to sink to the bottom of the bath 71. Consequently, the sample DNA fragment 151 is not substantially migrated in step S6. If the above step S6 shifts to step S6, the voltage control circuit 73 keeps on applying a voltage higher than that of the first electrode 74 from step S6 till step S15 in order to hold the sample DNA fragment 151.

After a predetermined time within which the sample DNA fragment having the relatively medium volume is expected to reach a part of the electrophoresis medium 82 located above the probe DNA fragment 61 in the fourth column, the voltage control circuit 73 clears, in accordance with an instruction from the controller 78, the voltage application state to set the first electrode 74, second electrode 75, and probe electrodes 35 (other than the probe electrode 35 in the eighth column if the above step S5 shifts to step S6) to have an equal voltage. Then, the controller 78 controls the driver circuit 76 and the irradiation driving circuit 79. In accordance with an instruction from the controller 78, the driver circuit 76 drives the light sensing device 2. Furthermore, the irradiation driving circuit 79 drives the ultraviolet irradiator 77 in accordance with an instruction from the controller 78 (step S7). Thus, the driver circuit 76 drives the light sensing device 2 so that the light sensing device 2 acquires an image representing the distribution of fluorescence intensities while the ultraviolet irradiator 77 is emitting light. The driver circuit 76 then outputs the image data to the controller 78.

On the basis of the image data, the controller 78 determines whether or not the photo sensor element 20 in the fourth column has sensed the fluorescence from the sample DNA fragment 152 having the relatively medium volume (step S8).

In this case, if the sample DNA fragment 152 having the relatively medium volume and almost the same number of bases as that in each of the probe DNA fragments 61 in the fourth to sixth columns is present in the surface layer of the electrophoresis medium 82, the sample DNA fragment with the same number of bases migrates onto the probe electrode 35 in the fourth column in the above step S6 as shown in FIG. 17. Accordingly, if the plural types of sample DNA fragments include the sample DNA fragment 152 having the relatively medium volume and almost the same number of bases as that in each of the probe DNA fragments 61 in the fourth to sixth columns, the fluorescence emitted by this sample DNA fragment is incident on the semiconductor film 23 of the photo sensor element 20 in the fourth column with a high intensity. Thus, in the above step S8, the controller 78 determines that the photo sensor element 20 in the fourth column has sensed the fluorescence (step S8: Yes), the processing by the controller 78 shifts to step S9. On the other hand, if the plural types of sample DNA fragments do not include the sample DNA fragment 152 having the relatively medium volume and almost the same number of bases as that in each of the probe DNA fragments 61 in the fourth to sixth columns, fluorescence of a low intensity or almost no fluorescence is incident on the semiconductor film 23 of the photo sensor element 20 in the fourth row. The controller 78 thus determines in the above step S8 that the photo sensor element 20 in the fourth column has not sensed the fluorescence (step S8: No). The processing by the controller 78 shifts to step S11.

Figure 18:
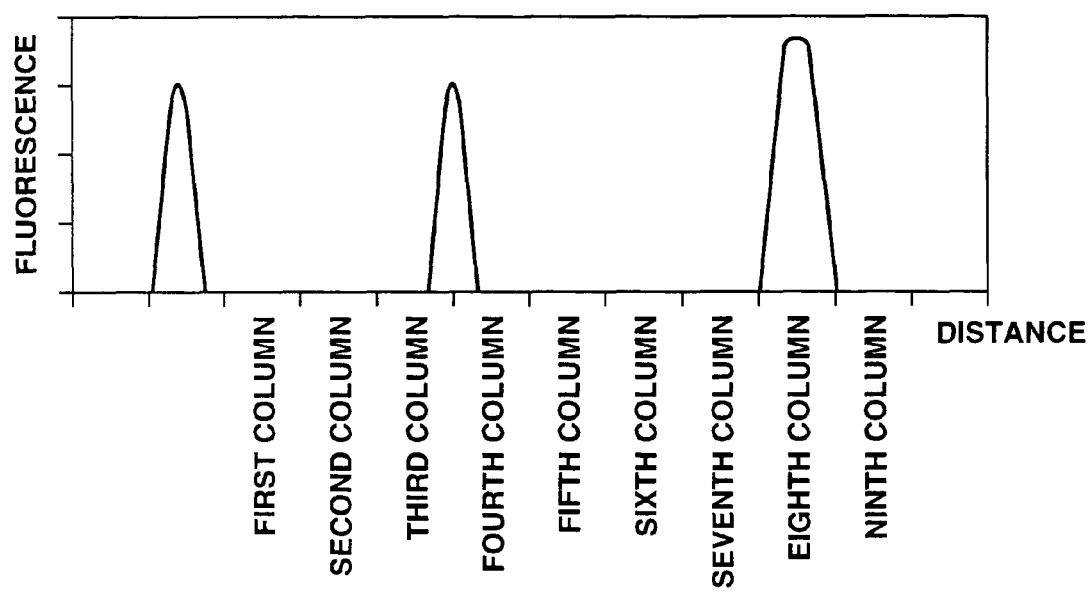
FIG. 18 is a graph showing the distribution of fluorescence intensities based on the distribution of the sample DNA fragments in FIG. 17.

FIG. 17 is a view showing a position through which the sample DNA fragment 152 migrates in the above step S6 if the sample DNA fragment 152 has almost the same number of bases as that in each of the probe DNA fragments 61 in the fourth to sixth columns. FIG. 18 is a graph representing the distribution of fluorescence intensities in an image acquired by the light sensing device 2 if the sample DNA fragment 152 has almost the same number of bases as that in each of the probe DNA fragments 61 in the fourth to sixth columns. In FIGS. 17 and 18, the sample DNA fragments 151 having the smallest number of bases and thus the relatively small volume has almost the same number of bases as that in each of the probe DNA fragments 61 in the seventh to ninth columns.

In step S9, in accordance with an instruction from the controller 78, the voltage control circuit 73 applies voltage so that the potential of the probe electrode 35 in the fifth column is higher than those of the other probe electrodes 35 (if the above step S5 shifts to step S6, then in step S9 and step S10, described later, the potentials of the probe electrodes 35 in the fifth and eighth columns are equal to each other and different from that of the probe electrode 35 in the fifth column) and first electrode 74. In this case, the probe electrodes 35 other than the one in the fifth column (however, the probe electrode 35 in the eighth column is excluded if the above step S5 shifts to step S6) and the first electrode 74 have a ground potential. The probe electrode 35 in the fifth column has a high voltage with respect to the ground voltage. In this case, the potential of the second electrode 75 is desirably equal to that of the first electrode 74 but may be higher than it. Thus, the electrode set composed of the probe electrodes 35 in the fourth to sixth columns is selected. Accordingly, in spite of the voltage between the first electrode 74 and the second electrode 75, the sample DNA fragment 151 having almost the same number of bases as that in each of the probe DNA fragments 61 in the seventh to ninth columns and having the relatively medium volume can be held close to the probe electrode 35 in the fifth column, that is, close to the probe DNA fragments 61 in the fourth to sixth columns. In step S9 and step S10, described later, the potential of the second electrode 75 is preferably also equal to that of the first electrode 74 because this prevents the sample DNA fragments from moving from the first electrode 74 to the second electrode 75.

Then, in accordance with an instruction from the controller 78, the driver circuit 76 drives the light sensing device 2 so that the light sensing device 2 acquires an image representing the distribution of fluorescence intensities while the ultraviolet irradiator 77 is emitting light. The driver circuit 76 then outputs the image data to the controller 78. Then, on the basis of the image data, the controller 78 determines whether or not the photo sensor element 20 in the fifth column has sensed the fluorescence (step S10).

Figure 20:
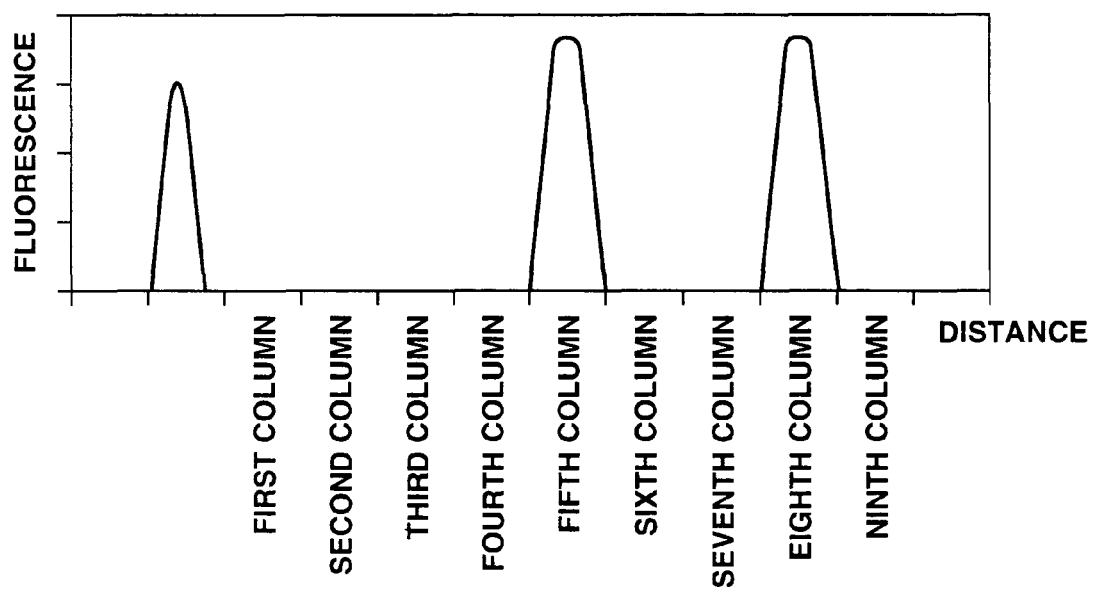
FIG. 20 is a graph showing the distribution of fluorescence intensities based on the distribution of the sample DNA fragments in FIG. 19.

In this case, if in the above step S9, a voltage higher than that of the first electrode 75 is applied to the probe electrode 35 in the fifth column, a sample DNA fragment having almost the same number of bases in the probe DNA fragments 61 in the fourth to sixth columns migrates so as to sink from the top of the probe electrode 35 in the fourth column toward the probe electrode 35 in the fifth column. Once the sample DNA fragment having almost the same number of bases as that in each of the probe DNA fragments 61 in the fourth to sixth columns migrates to the vicinity of the probe electrode 35 in the fifth column and is held on this probe electrode 35, the fluorescence emitted by this sample DNA fragment is incident on the semiconductor film 23 of the photo sensor element 20 in the fifth column with a high intensity as shown in FIG. 20. Thus, in the above step S10, the controller 78 determines that the photo sensor element 20 in the fifth column has sensed the fluorescence (step S10: Yes), the processing by the controller 78 shifts to step S11. On the other hand, if the sample DNA fragment having almost the same number of bases as that in each of the probe DNA fragments 61 in the fourth to sixth columns has not migrated to the vicinity of the probe electrode 35 in the fifth column, then the controller 78 determines in step S10 that the photo sensor element 20 in the fifth column has not sensed the fluorescence (step S10: No). Then, the processing by the controller 78 shifts to step S9. The processing by the controller 78 is repeated in order of step S9: No and step S10 to continuously apply a voltage higher than that of the first electrode 74 to the probe electrode 35 in the fifth column until the sample DNA fragment 152 with the relatively medium volume migrates to the vicinity of the probe electrode 35 in the fifth column.

Figure 19:
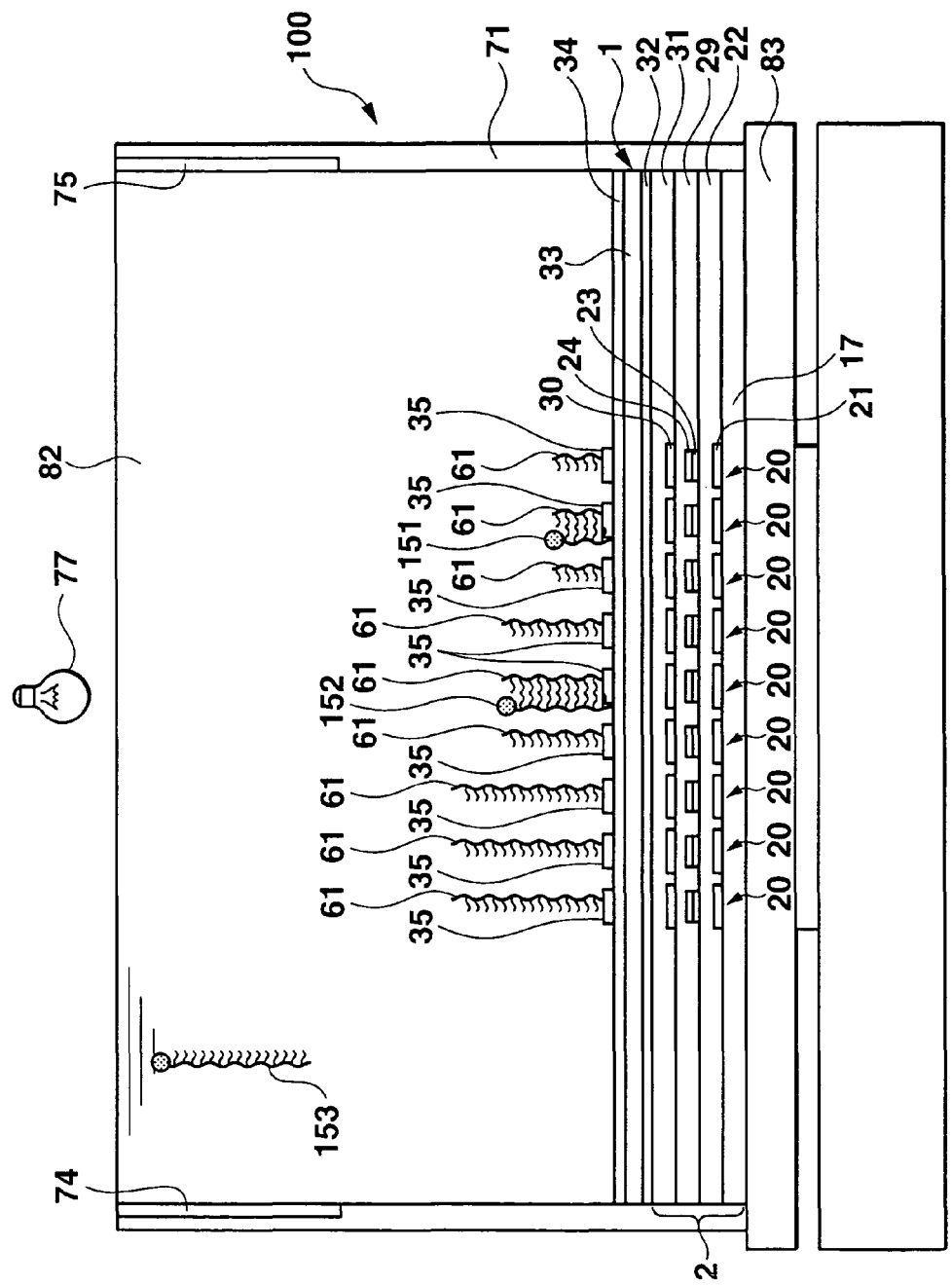
FIG. 19 is a diagram showing the distribution of the sample DNA fragments in the bath during the operation of the DNA identifying apparatus, together with the DNA identifying apparatus.

FIG. 19 is a view showing a position through which the sample DNA fragment 152 migrates in the above step S9 if the sample DNA fragment 152 has almost the same number of bases as that in each of the probe DNA fragments 61 in the fourth to sixth columns. FIG. 20 is a graph representing the distribution of fluorescence intensities in an image acquired by the light sensing device 2 if the sample DNA fragment 152 has almost the same number of bases as that in each of the probe DNA fragments 61 in the fourth to sixth columns.

In step S11 (third voltage applying step), in accordance with an instruction from the controller 78, the voltage control circuit 73 applies a voltage between the first electrode 74 and the second electrode 75 so that the potential of the first electrode 74 is lower than that of the second electrode 75. At the same time, in accordance with an instruction from the controller 78, the voltage control circuit 73 applies voltages to the probe electrodes 35 so that the probe electrodes 35 in the fifth to eight columns are maintained at potentials that enable the sample DNA fragment to be held, while the potentials of the probe electrodes 35 in the other columns remain equal to or lower than that of the second electrode 75, desirably equal to or lower than that of the first electrode 74. The potentials of the probe electrodes 35 in the fifth to eighth columns are set to be equal to or higher than the voltage applied to the first electrode 74 and equal to and lower than the voltage applied to the second electrode 75. However, the potentials of the probe electrodes 35 in the fifth to eighth columns are desirably equal to that of the second electrode 75 in order to hold the sample DNA fragment 151.

Figure 21:
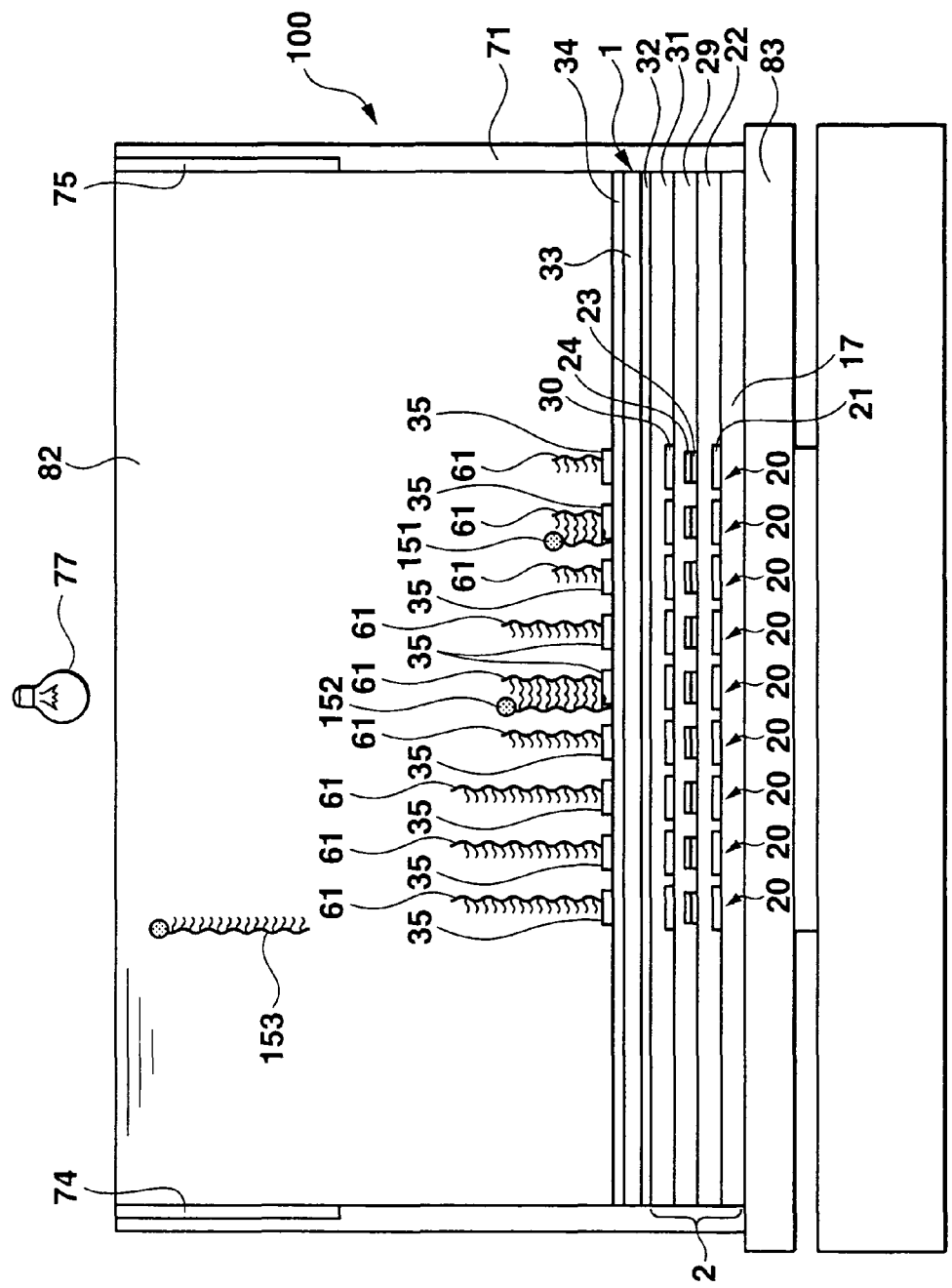
FIG. 21 is a diagram showing the distribution of the sample DNA fragments in the bath during the operation of the DNA identifying apparatus, together with the DNA identifying apparatus.

Thus, the sample DNA 153 having the relatively large volume, which is present in the surface layer of the electrophoresis medium and remains in it without being held, migrates through the electrophoresis medium 82 toward the second electrode 75. In this case, the voltage control circuit 73 maintains the above voltage state for a predetermined time. The application time and the applied voltage are such that the sample DNA fragment 152 having almost the same number of based as that in each of the probe DNA fragments 61 in the first to third columns and the relatively large volume migrates onto the probe electrode 35 in the first column. Accordingly, as shown in FIG. 21, if the sample DNA fragment 153 has almost the same number of bases as that in each of the probe DNA fragments 61 in the first to third columns, the sample DNA fragment 153 migrates onto the first column. However, the sample DNA fragments 151 and 152 have been held since the previous steps S4 and S9, respectively so as to sink to the bottom of the bath 71 because the voltage required to hold the sample DNA fragment was applied to the corresponding probe electrodes 35. Consequently, the sample DNA fragments 151 and 152 are not affected by the electric field between the first and second electrodes 74 and 75, located relatively above, and are not substantially migrated in step S11. If the above step S10 shifts to step S11, the voltage control circuit 73 keeps on applying a voltage relatively higher than that of the first electrode 74, to the probe electrode 35 in the fifth column from step S11 till step S15.

After a predetermined time within which the sample DNA fragment having the relatively large volume is expected to reach a part of the electrophoresis medium 82 located above the probe DNA fragment 61 in the first column, the voltage control circuit 73 clears, in accordance with an instruction from the controller 78, the voltage application state to set the first electrode 74 and probe electrodes 35 (other than the probe electrode 35 in the eighth column if the above step S5 shifts to step S6 or other than the probe electrode 35 in the fifth column if the above step S10 shifts to step S11) to have an equal voltage. The potential of the second electrode 75 is also desirably equal to that of the first electrode 74. Then, the controller 78 controls the driver circuit 76 and the irradiation driving circuit 79. In accordance with an instruction from the controller 78, the driver circuit 76 drives the light sensing device 2. Furthermore, the irradiation driving circuit 79 drives the ultraviolet irradiator 77 in accordance with an instruction from the controller 78 (step S12). Thus, the driver circuit 76 drives the light sensing device 2 so that the light sensing device 2 acquires an image representing the distribution of fluorescence intensities while the ultraviolet irradiator 77 is emitting light. The driver circuit 76 then outputs the image data to the controller 78.

Then, on the basis of the image data, the controller 78 determines whether or not the photo sensor element 20 in the fourth column has sensed the fluorescence (step S13).

In this case, if a sample DNA fragment having almost the same number of bases as that in each of the probe DNA fragments 61 in the first to third columns is present in the surface layer of the electrophoresis medium 82, the sample DNA fragment with the same number of bases migrates onto the probe electrode 35 in the first column in the above step S11 as shown in FIG. 21. Accordingly, if the plural types of sample DNA fragments include the sample DNA fragment having almost the same number of bases as that in each of the probe DNA fragments 61 in the first to third columns, the fluorescence emitted by this sample DNA fragment is incident on the semiconductor film 23 of the photo sensor element 20 in the first column with a high intensity. Thus, in the above step S13, the controller 78 determines that the photo sensor element 20 in the first column has sensed the fluorescence (step S13: Yes), the processing by the controller 78 shifts to step S14. On the other hand, if the plural types of sample DNA fragments do not include the sample DNA fragment 152 having the relatively medium volume and almost the same number of bases as that in each of the probe DNA fragments 61 in the first to third columns, fluorescence of a low intensity or almost no fluorescence is incident on the semiconductor film 23 of the photo sensor element 20 in the first row. The controller 78 thus determines in the above step S13 that the photo sensor element 20 in the first column has not sensed the fluorescence (step S13: No). The processing by the controller 78 shifts to a check step SC1.

Figure 22:
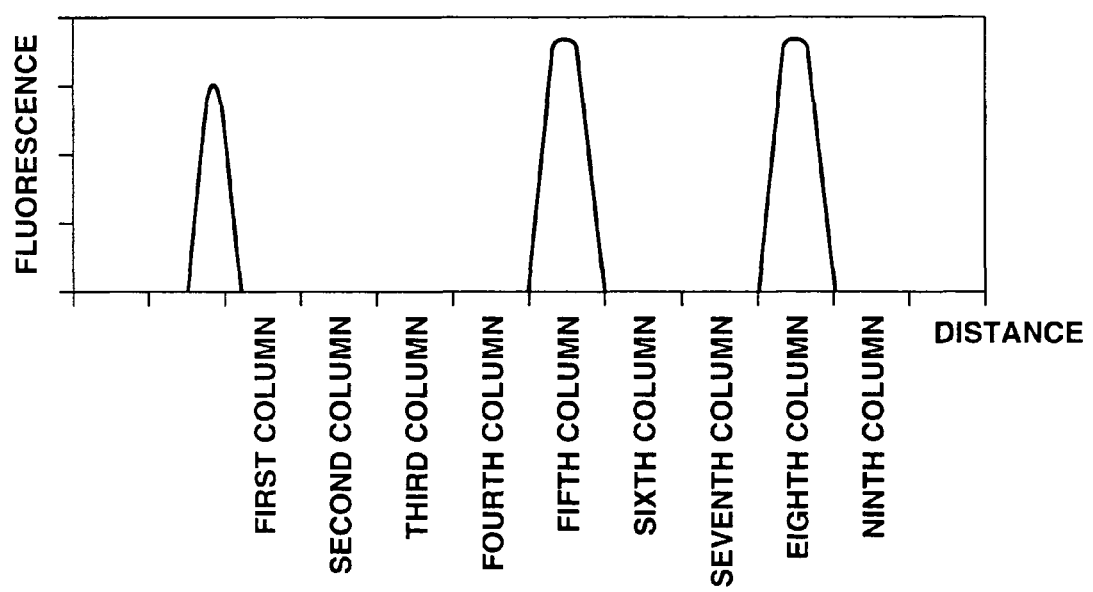
FIG. 22 is a graph showing the distribution of fluorescence intensities based on the distribution of the sample DNA fragments in FIG. 21.

FIG. 21 is a drawing showing a position through which the sample DNA fragment 152 migrates in the above step S11 if the sample DNA fragment 153 has almost the same number of bases as that in each of the probe DNA fragments 61 in the first to third columns. FIG. 22 is a graph representing the distribution of fluorescence intensities in an image acquired by the light sensing device 2 if the sample DNA fragment 153 has almost the same number of bases as that in each of the probe DNA fragments 61 in the first to third columns. In FIGS. 21 and 22, the sample DNA fragments 151 has almost the same number of bases as that in each of the probe DNA fragments 61 in the seventh to ninth columns. The sample DNA fragment 152 has almost the same number of bases as that in each of the probe DNA fragments 61 in the fourth to sixth columns.

In step S9, in accordance with an instruction from the controller 78, the voltage control circuit 73 applies voltage so that the potential of the probe electrode 35 in the second column is higher than those of the other probe electrodes 35 (the probe electrode 35 in the eighth column is excluded if the above step S5 shifts to step S6 or the probe electrode 35 in the fifth column is excluded if the above step S10 shifts to step S11) and first electrode 74. In this case, the probe electrodes 35 other than the one in the second and the first electrode 74 have a ground potential. The probe electrode 35 in the fifth column has a high voltage with respect to the ground voltage. Thus, the electrode set composed of the probe electrodes 35 in the first to third columns is selected. Accordingly, in spite of the voltage between the first electrode 74 and the second electrode 75, the sample DNA fragment 153 having almost the same number of bases as that in each of the probe DNA fragments 61 in the first to third columns and having the relatively large volume can be held close to the probe electrode 35 in the second column, that is, close to the probe DNA fragments 61 in the first to third columns. In step S14 and step S15, described later, the potential of the second electrode 75 is preferably also equal to that of the first electrode 74 because this prevents the sample DNA fragments from moving from the first electrode 74 to the second electrode 75.

Then, in accordance with an instruction from the controller 78, the driver circuit 76 drives the light sensing device 2 so that the light sensing device 2 acquires an image representing the distribution of fluorescence intensities while the ultraviolet irradiator 77 is emitting light. The driver circuit 76 then outputs the image data to the controller 78. Then, on the basis of the image data, the controller 78 determines whether or not the photo sensor element 20 in the second column has sensed the fluorescence (step S15).

Figure 24:
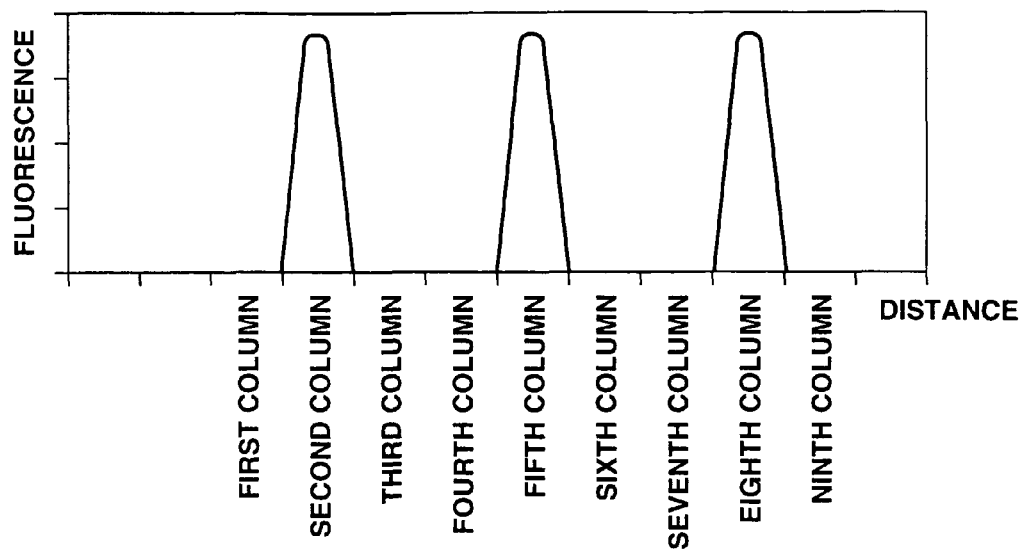
FIG. 24 is a graph showing the distribution of fluorescence intensities based on the distribution of the sample DNA fragments in FIG. 23.

In this case, if in the above step S14, a voltage higher than that of the first electrode 74 is applied to the probe electrode 35 in the second column, a sample DNA fragment having almost the same number of bases in the probe DNA fragments 61 in the first to third columns migrates so as to sink from the top of the probe electrode 35 in the first column toward the probe electrode 35 in the second column. Once the sample DNA fragment having almost the same number of bases as that in each of the probe DNA fragments 61 in the first to third columns is held on the probe electrode 35 in the second column, the fluorescence emitted by this sample DNA fragment is incident on the semiconductor film 23 of the photo sensor element 20 in the first column with a high intensity as shown in FIG. 24. Thus, in the above step S15, the controller 78 determines that the photo sensor element 20 in the fifth column has sensed the fluorescence (step S15: Yes), the processing by the controller 78 shifts to the check step SC1. On the other hand, if the sample DNA fragment having almost the same number of bases as that in each of the probe DNA fragments 61 in the first to third columns has not migrated to the probe electrode 35 in the second column, then the controller 78 determines in step S15 that the photo sensor element 20 in the second column has not sensed the fluorescence (step S15: No). Then, the processing by the controller 78 shifts to step S14. The processing by the controller 78 is repeated in order of step S15: No and step S14 to continuously apply a positive voltage to the probe electrode 35 in the second column until the sample DNA fragment migrates to the probe electrode 35 in the second column.

Figure 23:
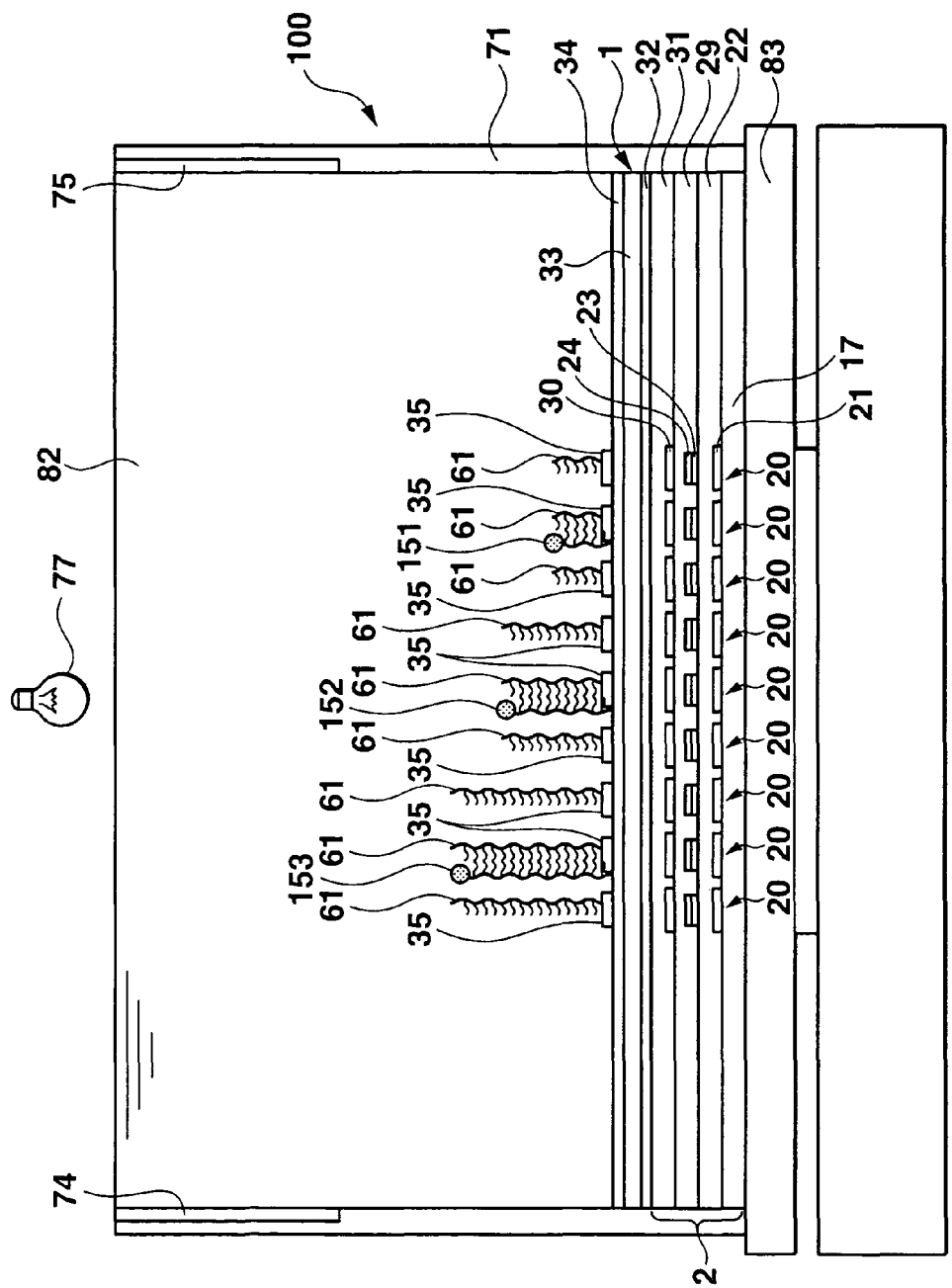
FIG. 23 is a diagram showing the distribution of the sample DNA fragments in the bath during the operation of the DNA identifying apparatus, together with the DNA identifying apparatus.

FIG. 23 is a view showing a position through which the sample DNA fragment 153 with the relatively large volume migrates in the above step S14 if the sample DNA fragment 153 has almost the same number of bases as that in each of the probe DNA fragments 61 in the first to third columns. FIG. 24 is a graph representing the distribution of fluorescence intensities in an image acquired by the light sensing device 2 if the sample DNA fragment 153 has almost the same number of bases as that in each of the probe DNA fragments 61 in the first to third columns.

In the check step SC1, the controller 78 checks whether the fluorescence has been sensed close to the probe electrode 35 in the seventh column in step S3 or to the probe electrode 35 in the eighth column in step S5. If the fluorescence is confirmed to have been sensed, the process shifts to step S16. If the fluorescence is confirmed not to have been sensed, the process shifts to a check step SC2.

In step S16, the controller 78 activates the shaker 83. The shaker 83 thus agitates the electrophoresis medium 82 in the bath 71 with an optimum intensity for the sample DNA fragment having almost the same number of bases as that in each of the probe DNA fragments 61 in the seventh to ninth columns. On this occasion, in accordance with an instruction from the controller 78, the voltage control circuit 73 sets the voltages of all the probe electrodes 35, first electrode 74, and second electrode 75. These electrodes may be set to have an equal voltage. However, if the agitation causes the sample DNA fragment to be dispersed more widely than required, the voltages of the probe electrodes 35 in the seventh to ninth columns may be higher than that of the first electrode 74.

Then, in accordance with an instruction from the controller 78, the driver circuit 76 drives the light sensing device 2 so that the light sensing device 2 acquires an image representing the distribution of fluorescence intensities while the ultraviolet irradiator 77 is emitting light. The driver circuit 76 then outputs the image data to the controller 78 (step S17). Then, on the basis of the image data, the controller 78 determines whether or not the photo sensor elements 20 in the seventh to ninth columns have sensed the fluorescence (step S18).

Figure 25:
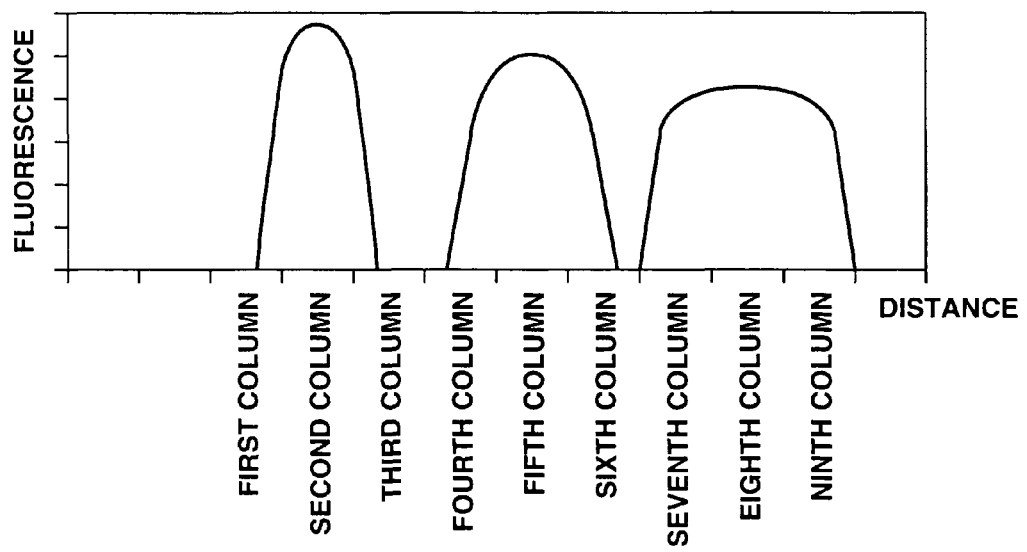
FIG. 25 is a graph showing the distribution of fluorescence intensities based on the distribution of the sample DNA fragments after a first agitation.

In this case, if the electrophoresis medium 82 is agitated in the above step S16, the sample DNA fragments migrated to the probe electrodes 35 in the eighth column spread to the probe electrodes 35 in the seventh and ninth columns. When the sample DNA fragments spread to the probe electrodes 35 in the seventh and ninth columns, the fluorescence emitted by these sample DNA fragments is incident on the semiconductor films 23 of the photo sensor elements 20 in the seventh to ninth columns with a high intensity as shown in FIG. 25. Thus, in the above step S18, the controller 78 determines that the photo sensor elements 20 in the seventh to ninth columns have sensed the fluorescence (step S18: Yes), the processing by the controller 78 shifts to the check step SC2. On the other hand, if the sample DNA fragments have not spread to the probe electrode 35 in the seventh or ninth column, then the controller 78 determines in step S18 that the photo sensor element 20 in the ninth column has not sensed the fluorescence (step S18: No). Then, the processing by the controller 78 shifts to step S16. The processing by the controller 78 is repeated in order of step S18: No, step S16, and step S17 to cause the shaker 83 to continue the agitating operation until the sample DNA fragments spread to the probe electrodes 35 in the seventh and ninth columns.

In the check step SC2, the controller 78 checks whether the fluorescence was sensed close to the probe electrode 35 in the fourth column in step S8 or to the probe electrode 35 in the fifth column in step S10. If the fluorescence is confirmed to have been sensed, the process shifts to step S19. If the fluorescence is confirmed not to have been sensed, the process shifts to a check step SC3.

In step S19, the controller 78 activates the shaker 83. The shaker 83 thus agitates the electrophoresis medium 82 in the bath 71 with an optimum intensity for the probe DNA fragments 61 in the fourth to sixth columns. On this occasion, in accordance with an instruction from the controller 78, the voltage control circuit 73 applies voltages so that the potentials of the probe electrodes 35 in the seventh to ninth columns are higher than those of the other probe electrodes 35, first electrode 74, and second electrode 75. In particular, the probe electrodes 35 other than those in the seventh to ninth columns, the first electrode, and the second electrode 75 are set to have the ground potential.

Then, in accordance with an instruction from the controller 78, the driver circuit 76 drives the light sensing device 2 so that the light sensing device 2 acquires an image representing the distribution of fluorescence intensities while the ultraviolet irradiator 77 is emitting light. The driver circuit 76 then outputs the image data to the controller 78 (step S20). Then, on the basis of the image data, the controller 78 determines whether or not the photo sensor elements 20 in the fourth to sixth columns have sensed the fluorescence (step S21).

Figure 26:
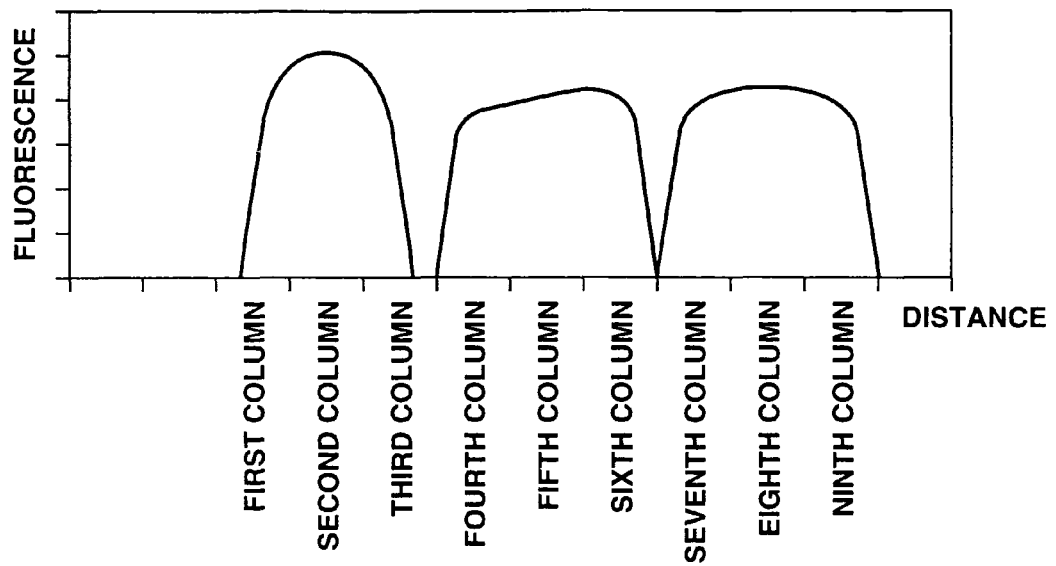
FIG. 26 is a graph showing the distribution of fluorescence intensities based on the distribution of the sample DNA fragments after a second agitation.

In this case, if the electrophoresis medium 82 is agitated in the above step S19, the sample DNA fragments migrated to the probe electrodes 35 in the fifth column spread to the probe electrodes 35 in the fourth and sixth columns. When the sample DNA fragments spread to the probe electrodes 35 in the fourth and sixth columns, the fluorescence emitted by these sample DNA fragments is incident on the semiconductor films 23 of the photo sensor elements 20 in the fourth to sixth columns with a high intensity as shown in FIG. 26. Thus, in the above step S21, the controller 78 determines that the photo sensor elements 20 in the fourth to sixth columns have sensed the fluorescence (step S21: Yes), the processing by the controller 78 shifts to the check step SC3. On the other hand, if the sample DNA fragments have not spread to the probe electrode 35 in the fourth or sixth column, then the controller 78 determines in step S21 that the photo sensor elements 20 in the fourth and sixth columns have not sensed the fluorescence (step S21: No). Then, the processing by the controller 78 shifts to step S19. The processing by the controller 78 is repeated in order of step S21: No, step S19, and step S20 to cause the shaker 83 to continue the agitating operation until the sample DNA fragments spread to the probe electrodes 35 in the fourth and sixth columns. While the shaker 83 is performing a shaking operation, a higher voltage is applied to the probe electrodes 35 in the seventh to ninth columns than to the first electrode 74. Consequently, the sample DNA fragments migrated and spread to the probe electrodes 35 in the seventh to ninth columns do not spread far from the probe electrodes 35 in the seventh to ninth columns.

In the check step SC3, the controller 78 checks whether the fluorescence was sensed close to the probe electrode 35 in the first column in step S13 or to the probe electrode 35 in the second column in step S15. If the fluorescence is confirmed to have been sensed, the process shifts to step S22. If the fluorescence is confirmed not to have been sensed, the process shifts to a check step SC4.

In step S22, the controller 78 activates the shaker 83. The shaker 83 thus agitates the electrophoresis medium 82 in the bath 71 with an optimum intensity for the sample DNA fragment having almost the same number of bases as that in each of the probe DNA fragments 61 in the first to third columns and having the relatively large volume. On this occasion, in accordance with an instruction from the controller 78, the voltage control circuit 73 applies voltages so that the potentials of the probe electrodes 35 in the fourth to ninth columns are higher than those of the probe electrodes 35 in the first to third columns, first electrode 74, and second electrode 75. In particular, the probe electrodes 35 in the first to third columns, the first electrode, and the second electrode 75 are set to have the ground potential.

Then, in accordance with an instruction from the controller 78, the driver circuit 76 drives the light sensing device 2 so that the light sensing device 2 acquires an image representing the distribution of fluorescence intensities while the ultraviolet irradiator 77 is emitting light. The driver circuit 76 then outputs the image data to the controller 78 (step S23). Then, on the basis of the image data, the controller 78 determines whether or not the photo sensor elements 20 in the fourth to sixth columns have sensed the fluorescence (step S24).

Figure 27:
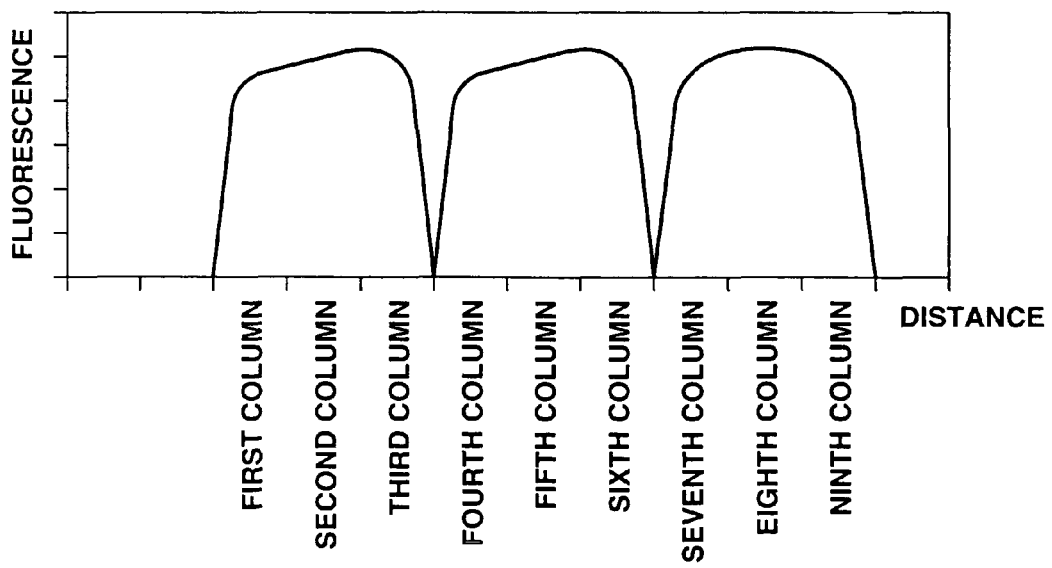
FIG. 27 is a graph showing the distribution of fluorescence intensities based on the distribution of the sample DNA fragments after a third agitation.

In this case, if the electrophoresis medium 82 is agitated in the above step S22, the sample DNA fragments migrated to the probe electrode 35 in the second column spread to the probe electrodes 35 in the first and third columns. When the sample DNA fragments spread to the probe electrodes 35 in the first and third columns, the fluorescence emitted by these sample DNA fragments is incident on the semiconductor films 23 of the photo sensor elements 20 in the first to third columns with a high intensity as shown in FIG. 27. Thus, in the above step S24, the controller 78 determines that the photo sensor elements 20 in the first to third columns have sensed the fluorescence (step S24: Yes), the processing by the controller 78 shifts to step S25. On the other hand, if the sample DNA fragments have not spread to the probe electrode 35 in the first or third column, then the controller 78 determines in step S24 that the photo sensor element 20 in the third column has not sensed the fluorescence (step S24: No). Then, the processing by the controller 78 shifts to step S22. The processing by the controller 78 is repeated in order of step S24: No, step S22, and step S23 to cause the shaker 83 to continue the agitating operation until the sample DNA fragments spread to the probe electrodes 35 in the first and third columns. While the shaker 83 is performing a shaking operation, a higher voltage is applied to the probe electrodes 35 in the fourth to ninth columns than to the first electrode 74. Consequently, the sample DNA fragments migrated and spread to the probe electrodes 35 in the fourth to ninth columns do not spread far from the probe electrodes 35 in the fourth to ninth columns.

In the check step SC4, the controller 78 checks whether or not it has been confirmed in at least one of the check steps SC1 to SC3 that the fluorescence has been sensed. If it is ascertained that the fluorescence has been confirmed to have been sensed, the process shifts to step S25. If it is ascertained that the fluorescence has not been confirmed to have been sensed, the operation is ended.

Figure 28:
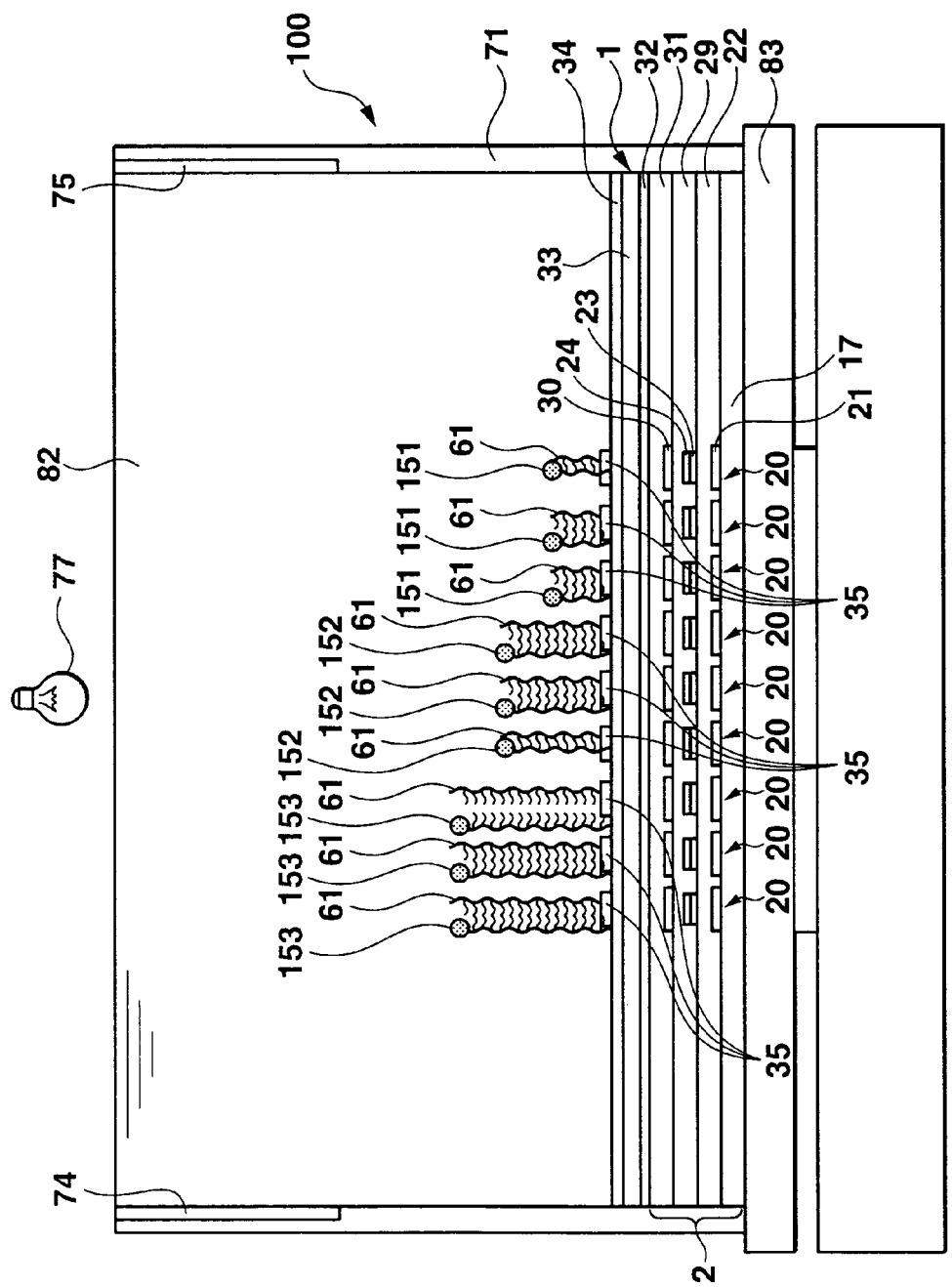
FIG. 28 is a diagram showing the distribution of the sample DNA fragments after the third agitation, together with the DNA identifying apparatus.

When the processing by the controller 78 shifts to step S25 as described above, a high density of sample DNA fragment having almost the same number of bases as that in the corresponding probe DNA fragment 61 has reached the corresponding spot 60. The plural types of sample DNA fragments have been classified according to the number of bases. Specifically, as shown in, for example, FIG. 28, if the sample DNA fragment 151 has the same number of bases as that in each of the probe DNA fragments 61 in the spots 60 in the seventh to ninth columns, a high density of sample DNA fragments 151 reach the spots 60 in the seventh to ninth columns. If the sample DNA fragment 152 has the same number of bases as that in each of the probe DNA fragments 61 in the spots 60 in the fourth to sixth columns, a high density of sample DNA fragments 152 reach the spots 60 in the fourth to sixth columns. If the sample DNA fragment 153 has the same number of bases as that in each of the probe DNA fragments 61 in the spots 60 in the first to third columns, a high density of sample DNA fragments 153 reach the spots 60 in the first to third columns.

In step S25, the agitation by the shaker 83 is ended. In accordance with an instruction from the controller 78, the voltage control circuit 73 sets all the probe electrodes 35, the first electrode 74, and the second electrode 75 to have an equal voltage. In particular, the voltage control circuit 73 preferably sets the probe electrodes 35, the first electrode 74, and the second electrode 75 to have the ground potential. Then, in accordance with an instruction from the controller 78, the temperature control circuit 80 drives the temperature regulating elements 72 to perform a cooling operation. This causes the temperature regulating elements 72 to absorb heat. The heat is thus transmitted from the probe electrodes 35 to the temperature regulating elements 72 to cool the electrophoresis medium 82 in the bath 71 down to about 45° C. If the temperature regulating elements 72 are only capable of heating, the temperature control circuit 80 stops causing the temperature regulating elements 72 to generate heat. This allows the electrophoresis medium 82 to be naturally cooled.

When the electrophoresis medium 82 in the bath 71 is cooled, if the probe DNA fragment 61 in the spot 60 at which a sample DNA fragment has arrived is complementary to this sample DNA fragment, the sample DNA fragment is hybridized to this probe DNA fragment 61. On the other hand, if the probe DNA fragment 61 in the spot 60 at which the sample DNA fragment has arrived is not complementary to this sample DNA fragment, the sample DNA fragment is not hybridized to this probe DNA fragment 61.

After a predetermined time has passed, the voltage control circuit 73 applies predetermined voltages in accordance with an instruction from the controller 78 so that the potentials of the first and second electrodes 74 and 75 are higher than those of all the probe electrodes 35 (step S26). In particular, the voltage control circuit 73 preferably sets the first and second electrodes 74 and 75 at the ground potential and sets each probe electrode 35 to have a negative voltage with respect to the first and second electrodes 74 and 75. In this case, the voltage of each probe electrode 35 with respect to the first electrode 74 is equal to or higher than a voltage required to separate a sample DNA fragment mis-hybridized to a probe DNA fragment from this probe DNA fragment and is equal to or lower than a voltage at which a sample DNA fragment hybridized to the corresponding probe DNA fragment is not separated from this probe DNA fragment.

If a negative voltage is applied to the probe electrode 35, then in the above step S25, those of the plural types of sample DNA fragments which have been mis-hybridized to the probe DNA fragments in certain spots 60 or which have not been hybridized to these probe DNA fragments are not complementary to these probe DNA fragments 61. Consequently, the sample DNA fragments are separated from these probe DNA fragments 61 and migrate to the first and second electrodes 74 and 75. On the other hand, those of the plural types of sample DNA fragments which have bee hybridized to the probe DNA fragments in certain spots 60 are complementary to these probe DNA fragments. Consequently, the sample DNA fragments remain bonded to these probe DNA fragments without being separated.

Figure 29:
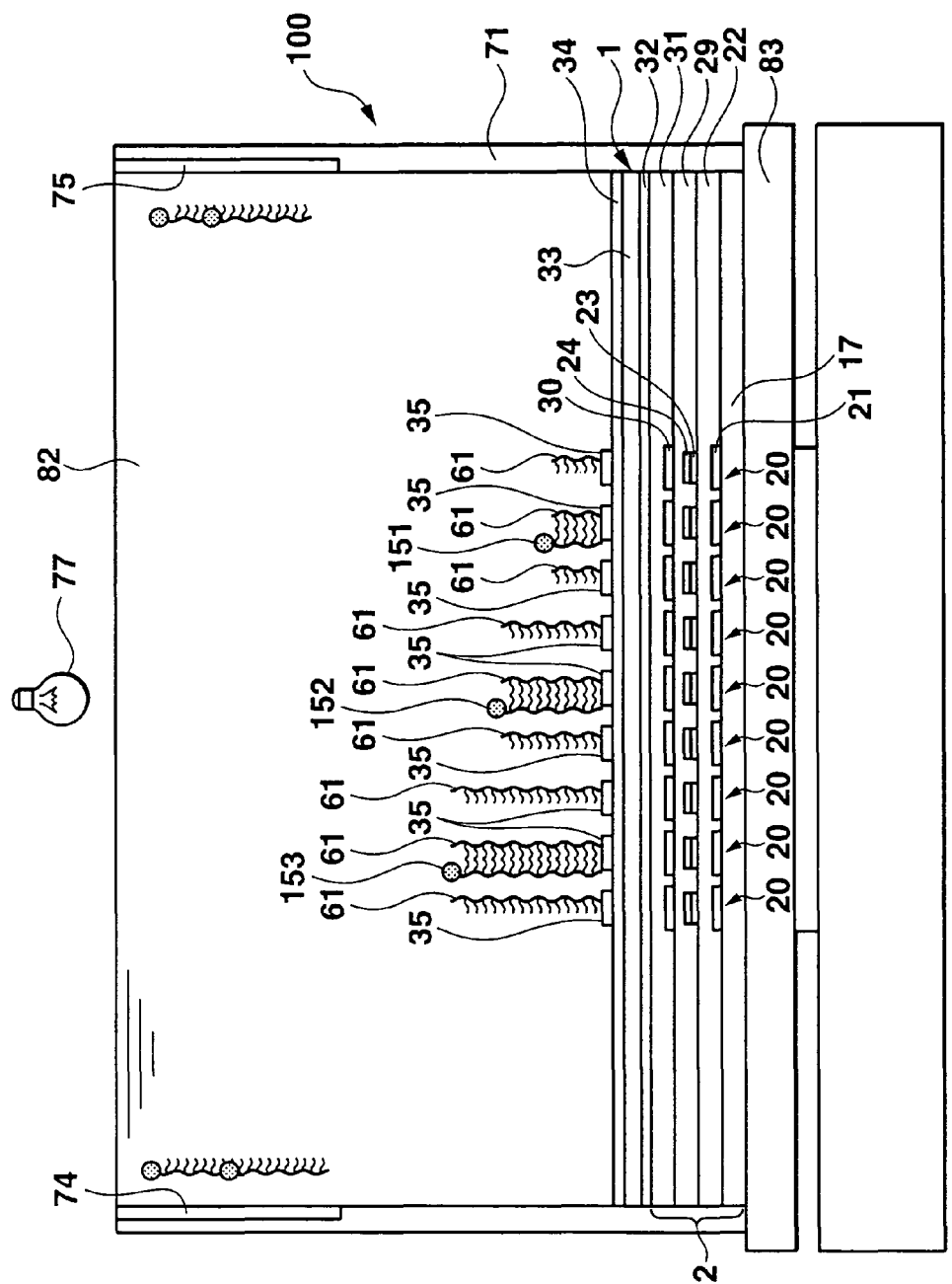
FIG. 29 is a diagram showing the distribution of the sample DNA fragments after non-hybridized sample DNA fragments have been attracted to a first electrode and a second electrode, together with the DNA identifying apparatus.
Figure 30:
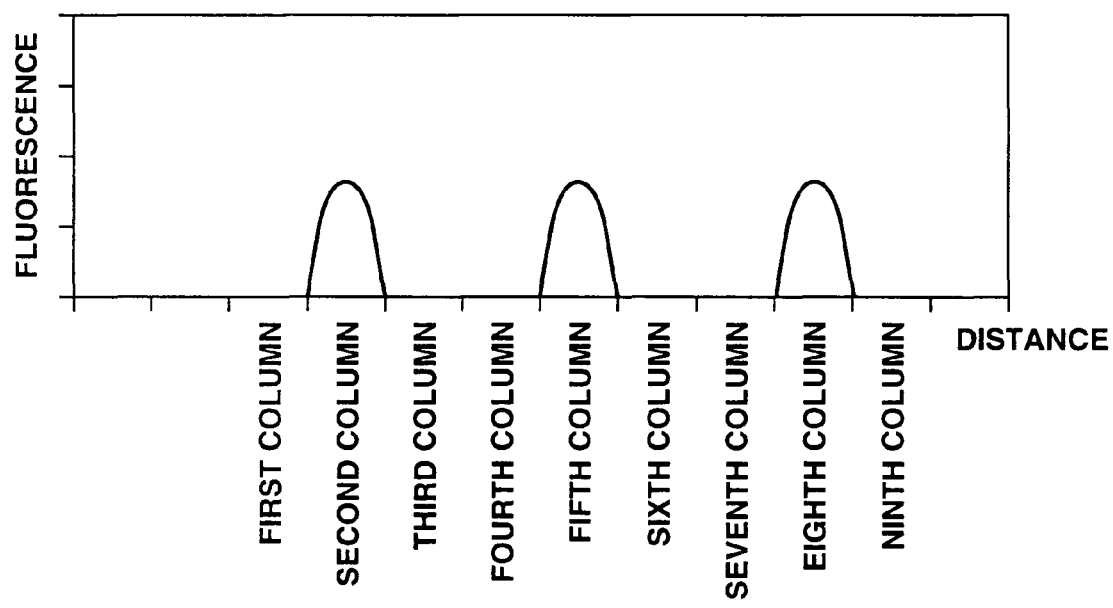
FIG. 30 is a graph showing the distribution of fluorescence intensities based on the distribution of the sample DNA fragments in FIG. 29.

Consequently, after step S26, the plural types of sample DNA fragments each remain only in the corresponding spot 60 including the complementary probe DNA fragment 61. The plural types of sample DNA fragments each do not remain in the spot 60 including a probe DNA fragment which has a different number of bases or which is not complementary to the sample DNA fragment. If the sample DNA fragment 151 has the same number of bases as that in the probe DNA fragment 61 in one of the spots 60 in the eighth column and is complementary to this probe DNA fragment as shown in, for example, FIG. 29, the sample DNA fragment 151 remains in one of the spots 60 in the eighth column. Likewise, if the sample DNA fragment 152 has the same number of bases as that in the probe DNA fragment 61 in one of the spots 60 in the fifth column and is complementary to this probe DNA fragment, the sample DNA fragment 152 remains in one of the spots 60 in the fifth column. If the sample DNA fragment 153 has the same number of bases as that in the probe DNA fragment 61 in one of the spots 60 in the second column and is complementary to this probe DNA fragment, the sample DNA fragment 152 remains in one of the spots 60 in the second column. If the sample DNA fragments 151, 152, and 153 are distributed as shown in FIG. 29, the distribution of fluorescence intensities along the row direction of the image is as shown in FIG. 30.

After a predetermined time has passed, the voltage control circuit 73 applies voltages in accordance with an instruction from the controller 78 so as to set the first electrode 74, the second electrodes 75, and all the probe DNA fragments 35 to have an equal voltage, for example, the ground potential. Then, in accordance with an instruction from the controller 78, for example, if the fluorescence is confirmed in step S3 or S5, the driver circuit 76 drives the photo sensor elements 20 in the corresponding columns, that is, the seventh to ninth columns. If the fluorescence is confirmed in step S3 or S5, step S8 or S10, and step S13 or S15, the driver circuit 76 drives the photo sensor elements 20 in the first to ninth columns. Then, the light sensing device 2 acquires an image representing the distribution of fluorescence intensities while the ultraviolet irradiator 77 is emitting light. The driver circuit 76 then outputs the image data to the controller 78 (step S27). Furthermore, the temperature control circuit 80 continuously drives the temperature regulating elements 72 from the above step S25 to step S27 to perform a cooling operation. Then, when the operation of the light sensing device 2 driven by the driver circuit 76 is finished, the temperature control circuit 80 ends the cooling operation performed by the temperature regulating elements 72. Moreover, a temperature detector may be provided inside the bath 71 to detect the temperature of the electrophoresis medium 82. The temperature detected by the temperature detector may be fed back to the controller 78, which then controls the temperature control circuit 80 in accordance with the detected temperature. Then, the temperature control circuit 80 may control the temperature regulating elements 72 so that the electrophoresis medium 82 is maintained at 45° C. or higher from step S25 to step S27.

Once the process is decided to shift to step S25, the photo sensor elements 20 in the first to ninth columns may be driven without confirming in which columns the fluorescence has been sensed.

The controller 78 outputs image data to the display device 81 to check which probe DNA fragments 61 have been completely hybridized, on the basis of image data optically detected by the photo sensor elements. The controller 78 thus identifies the base sequences of hybridized sample DNA fragments from the base sequences of the probe DNA fragments 61 on the basis of already known base sequence data on the probe DNA fragments 61 (step S28). The operation of the DNA identifying apparatus is finished. In step S28, the display device 81 may display the base sequences of the hybridized sample DNA fragments in accordance with the controller 78.

As described above, in the present embodiment, the spots 60 are divided into the electrode set composed of the probe electrodes 35 in the first to third columns, the electrode set composed of the probe electrodes 35 in the fourth to sixth columns, and the electrode set composed of the probe electrodes 35 in the seventh to ninth columns. The spots 60 arranged in the same electrode set have the same number of bases but different base sequences. Moreover, the number of bases in each spot 60 decreases as the corresponding electrode set is closer to the second electrode 75.

With the above configuration, when sample DNA fragments are injected into the first electrode 74 side and voltages are applied between the second electrode 75 and the first electrode 74, the sample DNA fragments start to migrate. However, sample DNA fragments having smaller numbers of bases have smaller volumes and thus lower fluid resistances. These sample DNA fragments migrate closer to the second electrode 75. Accordingly, the plural types of sample DNA fragments are classified according to the number of bases. In step S1, those of the plural types of sample DNA fragments which have almost the same number of bases as that in each of the probe DNA fragments in the seventh to ninth columns are separated from the other sample DNA fragments. Then in step S4, the sample DNA fragments are migrated in the depth direction toward the probe electrode 35 in the eighth column. Thus, the density of sample DNA fragments having almost the same number of bases increases around the probe electrode 35 in the eighth column. Step 9 is similarly executed after step S6, and step S14 is executed after step S11.

Subsequently, the optimum agitation for each of the numbers of bases is carried out. Consequently, the sample DNA fragments having almost the same number of bases are uniformly and densely distributed. Thus, in step S25, the sample DNA fragments can be hybridized only to the complementary probe DNA fragments having almost the same number of bases. Therefore, the base sequences of the plural types of sample DNA fragments can be almost simultaneously identified. Thus, the use of the present DNA identifying apparatus eliminates the need to execute a process of extracting sample DNA fragments having the same number of bases from all the sample DNA fragments obtained from a specimen.

When the process shifts to step S25, sample DNA fragments having the same number of bases are densely distributed at the respective spots 60. Accordingly, in the subsequent step S25, more sample DNA fragments are bonded to the complementary probe DNA fragments. Thus in the subsequent step S27, fluorescence of an increased intensity is emitted from the spots 60 complementary to the sample DNA fragments. As a result, the light sensing device 2 can efficiently detect the distribution of fluorescence.

In step S26, voltages lower than those applied to the electrodes 74 and 75 are applied to the probe electrodes 35. Accordingly, sample DNA fragments reaching non-complementary spots 60 have a negative polarity and thus leave the spots 60 and move to the first electrode 74 and the second electrode 75. In the subsequent step S27, no fluorescence is emitted from the spots 60 that are not complementary to the sample DNA fragments. Fluorescence is emitted from the spots 60 that are complementary to the sample DNA fragments. The fluorescence intensity can be clearly perceived. Therefore, an image obtained by the light sensing device 2 has such a high contrast as to make it possible to easily determine which parts of the image are brighter.

In step S26, the sample DNA fragments leave the non-complementary spots 60. This eliminates the need to clean the surface of the DNA sensor 1 after hybridization. Therefore, operational efficiency is improved. In step S26, voltages higher than those applied to the probe electrodes 35 are applied between the first electrode 74 and second electrode 75. However, a voltage higher than those applied to the probe electrodes 35 may be applied to only one of the first electrode 74 and second electrode 75.

Between step S1 and step S24, the temperature control circuit 80 controls the temperature regulating elements 72 to set the temperature of the electrophoresis medium 82 at about 95° C. The sample DNA fragments are not hybridized to one another but maintain their denatured state. Therefore, the sample DNA fragments migrate more easily.

The temperature control circuit 80 controls the temperature regulating elements 72 to set the temperature of the electrophoresis medium 82 at about 45° C. in step S25. This allows the sample DNA fragments to be easily hybridized to the complementary probe DNA fragments.

The plural types of spots 60 are arranged on the surface of the light sensing device 2. Accordingly, the light sensing device 2 can pick up clear images without any lenses or microscopes. Moreover, two-dimensional images can be picked up without any scanning mechanisms. This makes it unnecessary to provide the DNA identifying apparatus 100 with a lens, a microscope, or a scanning mechanism. The size of the DNA identifying apparatus 100 can thus be reduced.

Furthermore, the spots 60 are arranged on the surface of the light sensing device 2. Fluorescence emitted from the complementary spots 60 is incident on the corresponding photo sensor elements 20 of the light sensing device 2 without being substantially attenuated. Therefore, the light sensing device 2 need not be very sensitive.

The present invention is not limited to the above embodiment. Various improvements may be made or the design may be changed without departing from the spirit of the present invention.

For example, in the above embodiment, the probe electrodes 35 are divided into the electrode sets each composed of three adjacent probe electrodes 35. However, the probe electrode 35 may be divided into the electrode sets each composed of one, two, or four or more probe electrodes 35. Furthermore, the number of probe electrodes 35 may vary with the electrode sets. Moreover, in the above embodiment, one probe electrode 35 is provided for each vertical column of the photo sensor elements 20. However, one probe electrode 35 may be provided for every two or more vertical columns of the photo sensor elements 20. Moreover, in the above embodiment, one photo sensor element 20 corresponds to each spot 60. However, one spot 60 may correspond to two or more adjacent photo sensor elements 20. In either case, the spots 60 arranged in the same column has almost the same number of bases in the probe DNA fragment 61, and the base sequence of the probe DNA fragment 61 varies with the spots 60.

In step S4, only the probe electrode 35 in the eighth column is set to have a potential higher than those of the other probe electrodes 35. However, the present invention is not limited to this aspect. The same electrode set, that is, the probe electrodes 35 in the seventh to ninth columns may be set to have potentials higher than those of the other probe electrodes 35. In step S9, only the probe electrode 35 in the fifth column is set to have a potential higher than those of the other probe electrodes 35. However, the present invention is not limited to this aspect. The same electrode set, that is, the probe electrodes 35 in the fourth to sixth columns may be set to have potentials higher than those of the other probe electrodes 35. In step S14, only the probe electrode 35 in the second column is set to have a potential higher than those of the other probe electrodes 35. However, the present invention is not limited to this aspect. The same electrode set, that is, the probe electrodes 35 in the first to third columns may be set to have potentials higher than those of the other probe electrodes 35.

In the above embodiment, a single stranded sample DNA fragment with a smaller number of bases is electrically migrated and located in a part of the electrophoresis medium 82 located above the probe electrode 35 on which a probe DNA fragment 61 with a smaller number of bases is provided, and then a single stranded sample DNA fragment with a larger number of bases is electrically migrated and located in a part of the electrophoresis medium 82 located above the probe electrode 35 on which a probe DNA fragment 61 with the larger number of bases is provided. However, the position into which the plural types of sample DNA fragments are injected in their initial state and the positions of the probe electrodes 35 may be adjusted so as to execute the following process. A single stranded sample DNA fragment with a larger number of bases is electrically migrated and located in a part of the electrophoresis medium 82 located above the probe electrode 35 on which a probe DNA fragment 61 with the larger number of bases is provided, and then a single stranded sample DNA fragment with a smaller number of bases is electrically migrated and located in a part of the electrophoresis medium 82 located above the probe electrode 35 on which a probe DNA fragment 61 with a smaller number of bases is provided. In this case, settings are made so that steps S3 to S5 are executed when steps S13 to S15 are otherwise executed, while steps S13 to S15 are executed when steps S3 to S5 are otherwise executed and so that steps S16 to S18 are executed when steps S22 to S24 are otherwise executed, while steps S22 to S24 are executed when steps S16 to S18 are otherwise executed. Alternatively, sample DNA fragments may be almost simultaneously migrated to respective parts of the electrophoresis medium 82 located above the respective probe electrodes 35 on which probe DNA fragments 61 with almost the same number of bases as that in the corresponding sample DNA fragments are provided. In this case, the controller 78 may substantially synchronize steps S3, S8, and S13 to one another, steps S4, S9, and S14 to one another, and steps S5, S10, and S15 to one another.

In the above embodiment, the light sensing device 2 using the photo sensor elements 20 has been described as an example of a photoelectric converting element for pixels. The photoelectric converting element may be a light sensing device (image pickup device) using photo diodes. Light sensing devices using photo diodes may include CCD image sensors and CMOS image sensors other than double gate transistors provided that the temperature required for hybridization is within an operative temperature range.

The CCD image sensor includes photo diodes arranged on a substrate in an n×m matrix. A vertical CCD and a horizontal CCD are formed around each photo diode to transfer electric signals photoelectrically converted by the photo diode. The CMOS image sensor includes photo diodes arranged on a substrate in an n×m matrix. A pixel circuit is provided around each photo diode to amplify electric signals photoelectrically converted by the photo diode.

In the above embodiment, after the DNA analyzing apparatus 100 has been activated and before step S25 is started, the temperature control circuit 80 drives the temperature regulating elements 72 to maintain the electrophoresis medium 82 at a temperature of 95° C. or higher. However, the temperature regulating elements 72 may be controlled as described below in (a) to (d).

(a) In the case of "Yes" in the above step S3, from the above step S4 until the above step S16 is started, in accordance with an instruction from the controller 78, the temperature control circuit 80 drives the temperature regulating element 72 in the eighth column to perform a cooling operation. Thus, the temperature regulating element 72 in the eighth column absorbs heat to cool the probe electrode 35 in the eighth column to locally cool the spot 60 in the eighth column to about 45° C. This enables the probe DNA fragments 61 in the spot 60 in the eighth column to be hybridized. Moreover, in the case of "Yes" in the above step S3, from the above step S19 until the above step S27 is started, in accordance with an instruction from the controller 78, the temperature control circuit 80 drives the temperature regulating elements 72 in the seventh to ninth column to perform a cooling operation.

(b) In the case of "Yes" in the above step S8, from the above step S9 until the above step S19 is started, in accordance with an instruction from the controller 78, the temperature control circuit 80 drives the temperature regulating element 72 in the fifth column to perform a cooling operation. Thus, the temperature regulating element 72 in the fifth column absorbs heat to cool the probe electrode 35 in the eighth column to locally cool the spot 60 in the fifth column to about 45° C.

This enables the probe DNA fragments 61 in the spot 60 in the fifth column to be hybridized. Moreover, in the case of "Yes" in the above step S8, from the above step S22 until the above step S27 is started, in accordance with an instruction from the controller 78, the temperature control circuit 80 drives the temperature regulating elements 72 in the fourth to sixth column to perform a cooling operation.

(b) In the case of "Yes" in the above step S13, from the above step S14 until the above step S22 is started, in accordance with an instruction from the controller 78, the temperature control circuit 80 drives the temperature regulating element 72 in the second column to perform a cooling operation. Thus, the temperature regulating element 72 in the second column absorbs heat to cool the probe electrode 35 in the second column to locally cool the spot 60 in the fifth column to about 45° C. This enables the probe DNA fragments 61 in the spot 60 in the second column to be hybridized. Moreover, in the case of "Yes" in the above step S13, from the above step S25 until the above step S27 is started, in accordance with an instruction from the controller 78, the temperature control circuit 80 drives the temperature regulating elements 72 in the first to third column to perform a cooling operation.

(d) The temperature regulating elements 72 not subjected to the cooling operations in (a) to (c) are driven by the temperature control circuit 70 to perform a heating operation.

According to the present invention, the temperature regulating elements adjust the temperatures of the plurality of spots via the probe electrodes. Therefore, the vicinities of the spots in which hybridization occur can be locally and efficiently cooled.

What is claimed is:

1. A DNA analyzing apparatus comprising:
a bath containing an electrophoresis medium;
a first electrode and a second electrode arranged in the bath opposite each other in a width direction of the bath;
a light sensing device located in the bath at a height different from the heights of the first and second electrodes and at a position between the first electrode and the second electrode in the width direction of the bath;
a plurality of probe electrodes arranged along the width direction of the bath and above a surface of the light sensing device;
a plurality of different spots arranged on the probe electrodes, each of the spots including probe DNA fragments having known base sequences; and
a voltage control circuit which controls voltages applied to the first electrode, the second electrode, and the plurality of probe electrodes;
wherein the plurality of probe electrodes are divided into plural sets of the probe electrodes, each of the sets of the probe electrodes comprising a number of probe electrodes that are adjacent to each other along the width direction of the bath,
wherein the probe DNA fragments that are close to the second electrode have a smaller number of bases than the probe DNA fragments that are close to the first electrode, the number of bases in one of the probe DNA fragments on one of the probe electrodes that is closest to the first electrode is the largest among the probe DNA fragments that are close to the first electrode, and the number of bases in one of the probe DNA fragments on another of the probe electrodes that is closest to the second electrode is the smallest among the probe DNA fragments that are close to the second electrode; and
wherein, when the potential of the first electrode is lower than the potential of the second electrode, a plurality of types of sample DNA fragments injected in the electrophoresis medium migrates from the first electrode towards the second electrode in the electrophoresis medium, and, after a predetermined time, a sample DNA fragment having a predetermined number of bases among the sample DNA fragments reaches a location of the electrophoresis medium directly above one of the probe electrodes and the voltage control circuit sets an equal voltage in the first electrode, the second electrode, and the plurality of the probe electrodes, and each of the probe DNA fragments on the one of the probe electrodes and the sample DNA fragment are complementary each other and have almost identical number of bases.

2. The DNA analyzing apparatus according to claim 1, wherein the light sensing device comprises a planar light sensing device having a plurality of pixels arranged in an n×m matrix, where both n and m are integers equal to or larger than 2, and the probe electrodes are arranged such that one of the probe electrodes corresponds to one column of the pixels of the light sensing device.

3. The DNA analyzing apparatus according to claim 2, wherein the spots are arranged such that one of the spots corresponds to one of the pixels of the light sensing device.

4. The DNA analyzing apparatus according to claim 1, further comprising an ultraviolet irradiator located above the bath to irradiate the electrophoresis medium in the bath with ultraviolet rays emitted by the ultraviolet irradiator.

5. The DNA analyzing apparatus according to claim 1, further comprising a shaker which shakes the bath.

6. The DNA analyzing apparatus according to claim 1, wherein the plurality of probe electrodes are formed on a transparent substrate.

7. The DNA analyzing apparatus according to claim 1, further comprising an ultraviolet blocking layer between the plurality of probe electrodes and the surface of the light sensing device.

8. The DNA analyzing apparatus according to claim 1, wherein the light sensing device is removably attached to the bath.

9. The DNA analyzing apparatus according to claim 1, wherein the voltage control circuit repeats a voltage applying step by applying voltages to the first electrode and the second electrode so that the potential of the first electrode is lower than the potential of the second electrode.

10. The DNA analyzing apparatus according to claim 9, wherein the voltage control circuit sequentially selects, after each voltage applying step, one of the sets of the probe electrodes which is close to the second electrode, starting with one of the sets of the probe electrodes closest to the second electrode, and applies voltages to the selected set of the probe electrodes and the first and second electrodes so that the potentials of one or more probe electrodes in the selected set of the probe electrodes are higher than the potentials of the first and second electrodes or equivalent to the higher potential of the potentials of the first and second electrodes.

11. The DNA analyzing apparatus according to claim 9, wherein the voltage control circuit carries out a process of sequentially selecting, after each voltage applying step, one of the sets of the probe electrodes which is close to the second electrode, starting with one of the sets of the probe electrodes closest to the second electrode, and applying voltages to the selected set of the probe electrodes so that the potentials of one or more probe electrodes in the selected set of the probe electrodes are higher than the potentials of the first and second electrodes or equivalent to the higher potential of the potentials of the first and second electrodes, and repeats the process until all of the sets of the probe electrodes have been selected; and after all the sets of the probe electrodes have been selected, the voltage control circuit applies voltages to the first and second electrodes and the plurality of probe electrodes so that the potential of at least one of the first and second electrodes is higher than the potentials of the plurality of probe electrodes.

12. The DNA analyzing apparatus according to claim 11, further comprising a driver circuit which drives the light sensing device.

13. The DNA analyzing apparatus according to claim 1, wherein the probe DNA fragments within one of the plurality of spots have exactly the same base sequence and exactly the same number of bases.

14. The DNA analyzing apparatus according to claim 1, wherein the numbers of bases of the probe DNA fragments arranged in the same set of the probe electrodes are the same or are more similar to each other than the numbers of bases of the probe DNA fragments of the plurality of spots arranged in any other set of the probe electrodes.

15. The DNA analyzing apparatus according to claim 1, wherein the probe DNA fragments on the different spots arranged within each set of the probe electrodes have different base sequences.

16. The DNA analyzing apparatus according to claim 1, wherein the plural of types of sample DNA fragments are hybridized to the probe DNA fragments, when the plural of types of sample DNA fragments are injected in the electrophoresis medium.

17. The DNA analyzing apparatus according to claim 1, further comprising a plurality of temperature regulating elements which adjust temperatures of the plurality of different spots arranged on the probe electrodes.

* * * * *